(12) United States Patent
Moaseri

(10) Patent No.: US 11,964,049 B2
(45) Date of Patent: *Apr. 23, 2024

(54) WATER SOLUBLE COMPOSITIONS AND METHODS OF MAKING THE SAME

(71) Applicant: Nulixir Inc., Cedar Park, TX (US)

(72) Inventor: Ehsan Moaseri, Cedar Park, TX (US)

(73) Assignee: Nulixir Inc., Cedar Park, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/698,896

(22) Filed: Mar. 18, 2022

(65) Prior Publication Data

US 2022/0211619 A1 Jul. 7, 2022

Related U.S. Application Data

(63) Continuation of application No. 17/020,729, filed on Sep. 14, 2020, now Pat. No. 11,351,117.

(Continued)

(51) Int. Cl.

| | |
|---|---|
| *A61K 9/10* | (2006.01) |
| *A23L 29/10* | (2016.01) |
| *A23L 29/30* | (2016.01) |
| *A23L 33/155* | (2016.01) |
| *A61K 9/00* | (2006.01) |
| *A61K 9/08* | (2006.01) |
| *A61K 9/107* | (2006.01) |
| *A61K 9/16* | (2006.01) |
| *A61K 9/48* | (2006.01) |
| *A61K 9/50* | (2006.01) |
| *A61K 9/51* | (2006.01) |

(Continued)

(52) U.S. Cl.
CPC ............... *A61K 9/10* (2013.01); *A23L 29/10* (2016.08); *A23L 29/30* (2016.08); *A23L 33/155* (2016.08); *A61K 9/0053* (2013.01); *A61K 9/08* (2013.01); *A61K 9/107* (2013.01); *A61K 9/1075* (2013.01); *A61K 9/1652* (2013.01); *A61K 9/1664* (2013.01); *A61K 9/167* (2013.01); *A61K 9/4816* (2013.01); *A61K 9/4833* (2013.01); *A61K 9/4858* (2013.01); *A61K 9/4866* (2013.01); *A61K 9/4875* (2013.01); *A61K 9/4891* (2013.01); *A61K 9/5042* (2013.01); *A61K 9/5089* (2013.01); *A61K 9/513* (2013.01); *A61K 9/5161* (2013.01); *A61K 31/05* (2013.01); *A61K 31/192* (2013.01); *A61K 31/198* (2013.01); *A61K 31/352* (2013.01); *A61K 31/353* (2013.01); *A61K 31/375* (2013.01); *A61K 31/522* (2013.01); *A61K 31/525* (2013.01); *A61K 31/593* (2013.01); *A61K 35/741* (2013.01); *A61K 36/00* (2013.01); *A61K 36/06* (2013.01); *A61K 36/062* (2013.01); *A61K 36/16* (2013.01); *A61K 36/185* (2013.01); *A61K 36/28* (2013.01); *A61K 36/41* (2013.01); *A61K 36/53* (2013.01); *A61K 36/54* (2013.01); *A61K 36/61* (2013.01); *A61K 36/67* (2013.01); *A61K 36/68* (2013.01); *A61K 47/44* (2013.01); *A61K 45/06* (2013.01); *B82Y 5/00* (2013.01)

(58) Field of Classification Search
CPC . B82Y 5/00; A23L 29/30; A23L 29/10; A23L 33/155; A61K 9/10; A61K 9/08; A61K 9/167; A61K 9/1652; A61K 31/375; A61K 31/593; A61K 31/522; A61K 9/4833; A61K 9/4866; A61K 9/107; A61K 9/5161; A61K 9/0053; A61K 9/1075; A61K 9/513; A61K 47/44; A61K 9/1664; A61K 9/5042; A61K 9/5089; A61K 31/525; A61K 35/741; A61K 36/062; A61K 36/16; A61K 36/185; A61K 36/28; A61K 36/53; A61K 36/54; A61K 36/68; A61K 9/4816; A61K 9/4858; A61K 9/4875; A61K 9/4891; A61K 31/05; A61K 31/192; A61K 31/198; A61K 31/352; A61K 31/353; A61K 36/00; A61K 36/06; A61K 36/41; A61K 36/61; A61K 36/67; A61K 45/06
See application file for complete search history.

(56) References Cited

U.S. PATENT DOCUMENTS

| | | |
|---|---|---|
| 5,827,531 A | 10/1998 | Morrison |
| 6,423,363 B1 | 7/2002 | Traska et al. |

(Continued)

FOREIGN PATENT DOCUMENTS

| | | |
|---|---|---|
| CA | 2266518 A1 | 4/1998 |
| CN | 101001882 A | 7/2007 |

(Continued)

OTHER PUBLICATIONS

Nicholas Anton, et al, Aqueous-Core Lipid Nanocapsules for Encapsulating Fragile Hydrophilic and/or Lipophilic Molecules, 25 Langmuir 11413 (Year: 2009).*

(Continued)

*Primary Examiner* — Sean M Basquill
(74) *Attorney, Agent, or Firm* — Pillsbury Winthrop Shaw Pittman, LLP

(57) ABSTRACT

Provided is a composition for oral administration, the composition including: a dispersion medium including: an aqueous solution; and a dispersed phase including: a population of particles, each particle including: a core including: a first active ingredient; and an aqueous solution; a shell, substantially surrounding the core, the shell including: a lipophilic carrier; and a plurality of emulsifying agents; wherein the particle retards the release of the first active ingredient after consumption.

17 Claims, 13 Drawing Sheets

Related U.S. Application Data

(60) Provisional application No. 63/012,058, filed on Apr. 17, 2020, provisional application No. 62/968,591, filed on Jan. 31, 2020, provisional application No. 62/944,912, filed on Dec. 6, 2019, provisional application No. 62/899,595, filed on Sep. 12, 2019.

(51) Int. Cl.

| | |
|---|---|
| A61K 31/05 | (2006.01) |
| A61K 31/192 | (2006.01) |
| A61K 31/198 | (2006.01) |
| A61K 31/352 | (2006.01) |
| A61K 31/353 | (2006.01) |
| A61K 31/375 | (2006.01) |
| A61K 31/522 | (2006.01) |
| A61K 31/525 | (2006.01) |
| A61K 31/593 | (2006.01) |
| A61K 35/741 | (2015.01) |
| A61K 36/00 | (2006.01) |
| A61K 36/06 | (2006.01) |
| A61K 36/062 | (2006.01) |
| A61K 36/16 | (2006.01) |
| A61K 36/185 | (2006.01) |
| A61K 36/28 | (2006.01) |
| A61K 36/41 | (2006.01) |
| A61K 36/53 | (2006.01) |
| A61K 36/54 | (2006.01) |
| A61K 36/61 | (2006.01) |
| A61K 36/67 | (2006.01) |
| A61K 36/68 | (2006.01) |
| A61K 47/44 | (2017.01) |
| A61K 45/06 | (2006.01) |
| B82Y 5/00 | (2011.01) |

(56) References Cited

U.S. PATENT DOCUMENTS

| | | | |
|---|---|---|---|
| 6,720,007 | B2 | 4/2004 | Walt et al. |
| 9,427,007 | B2 | 8/2016 | Mason et al. |
| 10,028,919 | B2 | 7/2018 | Kaufman |
| 10,738,268 | B2 | 8/2020 | Leo |
| 11,351,117 | B2* | 6/2022 | Moaseri ............... A61K 31/593 |
| 11,497,809 | B2 | 11/2022 | Wu et al. |
| 2004/0014821 | A1 | 1/2004 | Varadaraj |
| 2005/0084472 | A1* | 4/2005 | Gedouin ............... A61K 8/066 |
| | | | 424/195.17 |
| 2008/0226772 | A1 | 9/2008 | Condeca Brinca et al. |
| 2010/0068290 | A1 | 3/2010 | Ziegler et al. |
| 2010/0330189 | A1 | 12/2010 | Niichel |
| 2011/0081451 | A1 | 4/2011 | Siegel et al. |
| 2011/0111020 | A1 | 5/2011 | Yan et al. |
| 2011/0182998 | A1 | 7/2011 | Reb et al. |
| 2011/0189298 | A1* | 8/2011 | Vos ........................ A23P 10/30 |
| | | | 264/4.1 |
| 2011/0195157 | A1 | 8/2011 | Niichel |
| 2012/0003288 | A1 | 1/2012 | Mori |
| 2012/0177730 | A1 | 7/2012 | Baron |
| 2014/0037744 | A1 | 2/2014 | Buisson et al. |
| 2015/0150822 | A1 | 6/2015 | Perumal et al. |
| 2015/0158004 | A1 | 6/2015 | Meiners et al. |
| 2015/0209298 | A1 | 7/2015 | Haksar et al. |
| 2016/0008237 | A1 | 1/2016 | Goldstein et al. |
| 2016/0128943 | A1 | 5/2016 | Vepuri et al. |
| 2016/0199378 | A1 | 7/2016 | Niichel |
| 2017/0157049 | A1 | 6/2017 | Dandl et al. |
| 2017/0281558 | A1 | 10/2017 | Castan et al. |
| 2019/0298683 | A1 | 10/2019 | Friedman |
| 2023/0157964 | A1 | 5/2023 | Kvitnitsky et al. |

FOREIGN PATENT DOCUMENTS

| | | |
|---|---|---|
| CN | 101252845 A | 8/2008 |
| CN | 104473161 A | 4/2015 |
| CN | 104684540 A | 6/2015 |
| CN | 104812777 A | 7/2015 |
| CN | 105146540 A | 12/2015 |
| CN | 107362154 A | 11/2017 |
| EP | 2201937 A1 | 6/2010 |
| RU | 2634904 C1 | 11/2017 |
| WO | 2014151364 A1 | 9/2014 |
| WO | 2018183115 A1 | 10/2018 |
| WO | 2019071213 A1 | 4/2019 |

OTHER PUBLICATIONS

N. Jager-Lezer, et al, Influence of Lipophilic Surfactant on the Release Kinetics of Water-Soluble Molecules Entrapped in a W/O/W Multiple Emulsion, 45 J Control. Rel. 1 (Year: 1997).*

Raynala, et al, A Topical W/O/W Multiple Emulsion Containing Several Active Substances: Formulation, Characterization and Study of Release, 26 J Control. Rel. 129 (Year: 1993).*

O. Doucet, et al, O/W Emulsion and W/O/W Multiple Emulsion: Physical Characterization and Skin Pharmacokinetic Comparison in the Delivery Process of Caffeine, 20 Int'l. J Cosm. Sci. 283 (Year: 1998).*

Non-Final Office Action for related U.S. Appl. No. 17/020,690 dated Apr. 11, 2023, 91 pages.

Non-Final Office Action for related U.S. Appl. No. 17/854,297 dated Apr. 11, 2023, 32 pages.

Final Office Action for related U.S. Appl. No. 17/470,994 dated Aug. 10, 2023, 15 pages.

Notice of Allowance in related U.S. Appl. No. 17/020,729 dated Mar. 18, 2022, pp. 1-11.

International Preliminary Report on Patentability in related international application PCT/US2020/050772 dated Mar. 18, 2022, pp. 1-5.

Jager-Lezer et al., "A Topical W/O/W Multiple Emulsion Containing Several Active Substances: Formulation, Characterization and Study of Release," 26 J Control. Rel. 129, 1993, pp. 1-13.

Doucet et al., O/W emulsion and W/O/W multiple emulsion: physical characterization and skin pharmacokinetic comparison in the delivery process of caffeine., International Journal of Cosmetic Science, 1998, pp. 283-295.

Anton et al., "Aqueous-Core Lipid Nanocapsules for Encapsulating Fragile Hydrophilic and/or Lipophilic Molecules," Langmuir Article, 25 (19) Jul. 16, 2009, pp. 11413-11419.

Raynal et al., "A topical W/O/W multiple emulsion containing several active substances: formulation, characterization and study of release.," Journal of Controlled Release, 26, 1993 Elsevier Science Publishers B.V., pp. 129-140.

Moaseri, Ehsan, "Long-Term Colloidal Stability of Polymer-Grafted Silica Nanoparticles in Concentrated Brine at Elevated Temperatures," Thesis, the University of Texas at Austin, May 2017, pp. 1-65.

Nanovex Biotechnologies, "How to Choose the Appropriate Nanovesicle," https://www.nanovexbiotech.com/choose-appropriate-nanovesicle/, Mar. 15, 2017, pp. 1-6.

Guar et al., Nanovesicles of nitrendipine with lipid complex for transdermal delivery: pharmacokinetic and pharmacodynamic studies, Artificial Cells, Nanomedicine, and Biotechnology, https://www.tandfonline.com/doi/full/10.3109/21691401.2015.108017044:7, Sep. 16, 2015, 1684-1693, DOI: 10.3109/21691401.2015.1080170.

Non-Final Office Action in related U.S. Appl. No. 17/162,916 dated Jun. 10, 2022, pp. 1-16.

Notice of Allowance in related U.S. Appl. No. 17/162,916 dated Jul. 20, 2022, 1-8 pages.

Non-Final Office Action for related U.S. Appl. No. 17/470,994 dated Nov. 22, 2022, pp. 1 to 25.

Examination Report for related Chinese Patent Application 202080071670.6 dated Jan. 28, 2023, 12 pages with English Translation on pp. 1 to 5.

(56) References Cited

OTHER PUBLICATIONS

Muschiolik, et al., "Double Emulsions Relevant to Food Systems: Preparation, Stability, and Applications, Comprehensive Reviews in Food Science and Food Safety," from Comprehensive Reviews in Food Science and Food Saftey, 2017, vol. 16, https://doi.org/10.1111/1541-4337.12261, Mar. 23, 2017, pp. 1 to 24.
Non-Final Office Action for related U.S. Appl. No. 17/020,731 dated May 8, 2023, 109 pages.
Extended Search Report for related European Patent Application 20862499.9 dated Aug. 4, 2023, 15 pages.
Office Action for Canadian Patent Application 3150979 issued on Nov. 10, 2023, 3 pages.
Non-Final Office Action for related U.S. Appl. No. 17/020,692 issued on Nov. 20, 2023, 65 pages.
Final Office Action for related U.S. Appl. No. 17/854,297 issued on Jan. 11, 2024, 36 pages.
Final Office Action for related U.S. Appl. No. 17/020,731 issued on Jan. 30, 2024, 32 pages.

\* cited by examiner

WATER SOLUBLE COMPOSITIONS AND METHODS OF MAKING THE SAME

CROSS-REFERENCE TO RELATED APPLICATIONS

This patent application is a continuation of U.S. Non-Provisional patent application Ser. No. 17/020,729, filed 14 Sep. 2020. U.S. Non-Provisional patent application Ser. No. 17/020,729 claims the benefit of U.S. Provisional Patent Applications 62/899,595, filed 12 Sep. 2019, titled ALIMENTARY-RELATED PARTICLES, PRODUCTION METHODS, AND PRODUCTION APPARATUS; 62/944,912, filed 6 Dec. 2019, titled ALIMENTARY-RELATED PARTICLES, PRODUCTION METHODS, AND PRODUCTION APPARATUS; 62/968,591, filed 31 Jan. 2020, titled ALIMENTARY-RELATED PARTICLES, PRODUCTION METHODS, AND PRODUCTION APPARATUS, and 63/012,058, filed 17 Apr. 2020, titled ALIMENTARY-PRODUCT RELATED PARTICLES, PRODUCTION METHODS, AND PRODUCTION APPARATUS. The entire content of each afore-listed earlier-filed application is hereby incorporated by reference for all purposes.

BACKGROUND

1. Field

The present disclosure relates generally to alimentary products and, more specifically, to alimentary products encapsulating nutrients or other payloads.

2. Description of the Related Art

Encapsulation of one substance in another may take a variety of forms. Often, encapsulation involves entrapping or otherwise enveloping a liquid, solid, or gas (referred to as the core material, internal phase, first phase, or payload, interchangeably) in an enclosing material commonly referred to as the carrier, particle, shell, wall, capsule or membrane interchangeably. Historically, certain types of encapsulation, and particularly those with limited or no mouthfeel imparted by capsules, were regarded as commercially infeasible in the food and beverage industry for many use cases due to cost, shelf stability, and various other challenges.

SUMMARY

The following is a non-exhaustive listing of some aspects of the present techniques. These and other aspects are described in the following disclosure.

Some aspects include a composition for oral administration, the composition including: a dispersion medium including: an aqueous solution; and a dispersed phase including: a population of particles, each particle including: a core including: a first active ingredient; and an aqueous solution; a shell, substantially surrounding the core, the shell including: a lipophilic carrier; and a plurality of emulsifying agents; wherein the particle retards the release of the first active ingredient after consumption.

BRIEF DESCRIPTION OF THE DRAWINGS

The above-mentioned aspects and other aspects of the present techniques will be better understood when the present application is read in view of the following figures in which like numbers indicate similar or identical elements.

Figure 1:
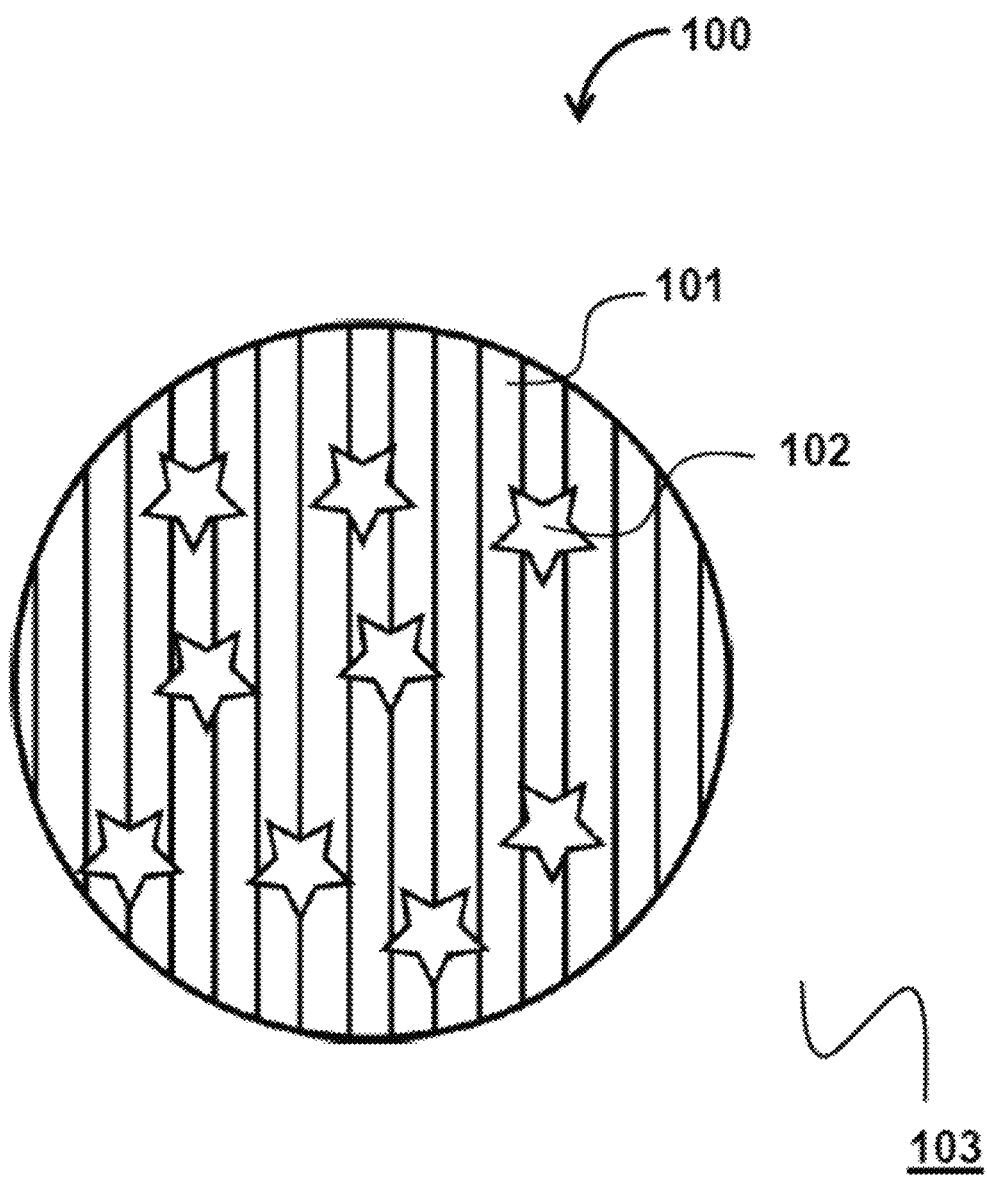
FIG. 1 is a schematic diagram that illustrates a miscible single-phase particle, in accordance with some embodiments of the present disclosure.

While the present techniques are susceptible to various modifications and alternative forms, specific embodiments thereof are shown by way of example in the drawings and will herein be described in detail. The drawings may not be to scale. It should be understood, however, that the drawings and detailed description thereto are not intended to limit the present techniques to the particular form disclosed, but to the contrary, the intention is to cover all modifications, equivalents, and alternatives falling within the spirit and scope of the present techniques as defined by the appended claims.

DETAILED DESCRIPTION OF CERTAIN EMBODIMENTS

To mitigate the problems described herein, the inventors had to both invent solutions and, in some cases just as importantly, recognize problems overlooked (or not yet foreseen) by others in the field of the food and beverage industry or the flavoring industry. Indeed, the inventors wish to emphasize the difficulty of recognizing those problems that are nascent and will become much more apparent in the future should trends in industry continue as the inventors expect. Further, because multiple problems are addressed, it should be understood that some embodiments are problem-specific, and not all embodiments address every problem with traditional systems described herein or provide every benefit described herein. That said, improvements that solve various permutations of these problems are described below.

Headings are used below to orient the reader. The introduction in section 1 generally describes issues addressed by embodiments in each of the sections that follow. Section 2, labeled particles, discusses particles surrounded by a liquid medium, and section 3 discusses solid-state particles, like powders. Section 4 discusses materials with which the particles in sections 2 and 3 may be made, and sections 5 and 6 discuss size and stability properties of those particles. Section 7 explains the theory underlying these embodiments, and section 8 discusses mixing techniques by which the particles in sections 2 and 3 may be manufactured. Sections 9, 10, 11, and 12 describe taste, permeability, release time profiles, and bio-availability of alimentary products with the particles of sections 2 and 3. Section 13 describes examples of alimentary and non-alimentary products in which the previously described compositions may be used, and finally, section 14 describes various ways of characterizing the particles, how to use the particles of sections 2 and 3, and how the particles of sections 2 and 3 operate, in some embodiments.

1. Introduction

Some forms of encapsulation are used in pharmaceuticals for various purposes. For example, particles with controlled-release mechanisms are used to provide a steady delivery of drugs to the body. Other examples include using smart particles, containing cancer drugs. These techniques, however, are generally not suitable for use in the food and beverage industry due to the high cost of manufacturing or expensive materials required for encapsulation.

To the extent encapsulation technology is used in food and beverage industry, the particles are either too large (e.g., may be felt in the mouth of the user, often with particles so large as to lead to be unpleasant) or are only capable of encapsulating a limited number of ingredients. An example is microencapsulation of fish oils to fortify bread. Encapsulation mitigates or eliminates the fishy aroma and taste of such oils, with an added benefit of less susceptibility to oxidation and less development of rancidity. However, techniques to manufacture such particles are capable of encapsulating only water-insoluble cargoes. Another example is cannabidiol (CBD)-infused beverages wherein an emulsion of CBD particles are stabilized in water via various types of surfactants. Emulsification techniques, used to manufacture CBD-infused beverages, may produce stable emulsions with particles only in the size range of tens of nanometers. Bigger particles often may not be stabilized with this technique because the stabilizer agent used in these techniques are small molecule surfactants that cannot stabilize particles in the size range of hundreds of microns. This is believed to limit the amount of cargo that may be encapsulated and added into a beverage. In addition, many of these techniques are also limited to encapsulation of water-insoluble cargoes. (None of which is to suggest that any subject matter is disclosed here or anywhere else in this document where tradeoffs are discussed.)

Thus, existing approaches to encapsulate ingredients with food-grade encapsulants are either too expensive, have short shelf-life, or produce particles that are too large to remain un-noticed by the consumer. A need exists for a technique to manufacturing small particles, capable of encapsulating a variety of water-insoluble and water-miscible ingredients, which may be dispersed in a variety of mediums, is cost-compatible with margins in the food and beverage industry, and produces a smaller or no change in the mouth-feel and quality of the host material.

Some embodiments mitigate the above described issues with traditional encapsulation processes. Some embodiments incorporate a variety of nutrients, nootropics, functional ingredients, flavoring agents, intoxicants, stimulants, or other payloads in particles that may be added to various food and beverage products without detrimentally affecting the mouth-feel of the host material.

Some embodiments produce particles containing a variety of ingredients. In some embodiments, particles may mask the flavor of the encapsulated ingredients, control the release kinetics of the encapsulated ingredients after consumption, control the delivery location of the encapsulated ingredients, stabilize the encapsulated ingredients in the host material, prolong the shelf life of the encapsulated ingredients, or enhance the bioavailability of the encapsulated ingredients.

In some embodiments, particles may mask the flavor of the encapsulated ingredients, in some cases making the taste of those ingredients almost unnoticeable for the consumer. For example, some embodiments are expected to mask the bitter taste of vodka (or tequila, gin, rum, grain alcohol, or the like) in a beverage (e.g., water, juice, soda, or other mixers) by encapsulating the vodka in the particles, dispersed in a host beverage, by maintaining a barrier between the vodka and the consumer's taste buds, until the particles rupture or dissolve in the digestive tract to release their encapsulants. In some embodiments, only some of the vodka may be encapsulated to mitigate the effect of the taste of vodka. In some embodiments, the taste of vodka is expected to be reduced for a given concentration of vodka in a beverage. For instance, when tested by a panel of adult subjects given a blind taste test, it is expected that more than half will report a lower-concentration of vodka in a beverage subject to the present treatment relative to a control beverage with substantially the same concentration of vodka (e.g., within 5%)—a test protocol that applies to other assertions of change in taste where unless another protocol is specified.

In some embodiments, particles may delay the release of encapsulated ingredients into the host medium in which the particles are dispersed. In some embodiments, delayed release is used to mask the flavor of the encapsulated components. In some embodiments, the delayed release is used to slow down the digestion and absorption of the encapsulated ingredients inside the body. In some embodiments, the particles are made of pH triggered materials, whereby the particles release the encapsulated ingredients in media with specific pH ranges. In some embodiments, the particles are tuned to release the encapsulated ingredients in acidic environment of the stomach or the intestine. In some embodiments, the particles are made of enzyme-digestible materials, whereby the particles release the encapsulated ingredients in presence of enzymes. In some cases, such enzymes are available enzymes in the digestive tract. In some embodiments, the particles are made of materials that dissolve in presence of digestive juices from the pancreas, liver, and intestine, whereby releasing the encapsulated ingredients.

In some embodiments, the particles protect an encapsulated ingredient from structural damage before or after consumption. For example, probiotics may be damaged and deactivated in acidic environment of the digestive tract before reaching the small intestine. By encapsulating probiotics, a particle can deliver probiotics without any damage to the small intestine by preventing a direct interaction between the probiotics and the digestive tract until the particle reaches the small intestine and starts releasing the encapsulated probiotics. In some embodiments, particles may be made of (full particle or only some of the layers of the particle) a polymer which degrades in the presence of bacterial enzymes with a pH-independent polymer. Such polymers can control the release of the encapsulants in a pre-determined site of the digestive tract (e.g. in the distal large intestine, beginning at the cecum, and continuing through the ascending, transverse, and descending colon, and ending in the sigmoid colon.)

In some embodiments, the particles keep an immiscible component dispersed in a host solution. For example, cannabidiol (CBD) oil is immiscible in a variety of water-based beverages, like water, sodas, beer, wine, liquor, fruit juice, seltzer, smoothies, kombucha, and the like. By encapsulating CBD oil, a stable emulsion of CBD oil droplets, encapsulated inside a polymeric shell, in a water-based beverage is expected to be obtainable (e.g., with less than half of the CBD oil separating out at a 1% concentration by mass over one week at room temperature). In some embodiments, the particles have a hydrophilic exterior that makes them soluble (e.g., component is regarded as soluble if more than a 0.1% concentration by mass is stable at room temperature, unless another criteria for solubility is specified by industry standards for a particular host beverage at issue, in which case the industry practice governs) and dispersible in water-based solutions.

In some embodiments, the particles prolong the shelf life of encapsulants by protecting the encapsulants from direct interaction with the surrounding medium. For example, particle may hinder exposure of the encapsulants to moisture or oxygen and prolong the shelf life.

In some embodiments, the particles increase the bioavailability of the encapsulants. For example, bioavailability of cannabidiol (CBD) oil is increased by encapsulating the CBD oil in water soluble small particles (e.g. 50 nm, 100 nm, or 200 nm). In some embodiments, a bioavailability of an ingredient may be increased by encapsulating the ingredient in a particle that has bioavailability enhancer compounds.

The particles may be added to, formed within, or contain, various host food or beverage products or other alimentary products. In some embodiments, these particles may be added to, formed within, or contain various drugs and other pharmaceutical products.

2. Particles

In some embodiments, a particle is referred to as globular if the length-width ratio (meaning the ratio of the length (largest dimension) of the particle divided by the width (smallest dimension) which is fixed at an angle of 90° in relation to the length) is less than about 4. The length-width ratio of a globular particle may be less than about 3, 2, 1.8, 1.5, 1.2, or 1.1. Some embodiments have globular particles.

In some embodiments, a particle may be a capsule having a boundary wall (e.g. shell) that defines (and separates) an interior and exterior of the respective capsule. In some embodiments, the boundary shell may have multiple layers.

In some embodiments, a particle may be made of droplets. In some embodiments, a particle may be formed of a droplet with a stabilizing layer covering the droplet. In some embodiments, the stabilizing layer is a polymeric shell. In some embodiments, the stabilizing layer may be formed of stabilizing agents, such as a surfactant, coated on the droplet. In some embodiments, the stabilizing layer may be made of an impermeable material. For example, a droplet of aqueous solution may be covered by a layer of oil acting as the boundary wall. In some embodiments, the stabilizing layer may be formed of a plurality of above-mentioned embodiments.

In some embodiments, some of the layers may be separating layers (e.g. seal coat) between the layer (or core) containing the encapsulant and another layer (e.g. the delayed release layer). The functions of a separating layer may be to provide a smooth base for the application of the delayed release layer, to prolong the core's (or internal layers) resistance to various conditions (e.g. acidic, neutral, enzymes), and to improve stability by inhibiting any interaction between the encapsulants and the delayed release layer. In some embodiments, a seal layer may be used to separate any two layer of a multi-layer particle or to provide a seal between the particle and the surrounding medium. In some embodiments, a seal layer (e.g. a water-permeable diffusion barrier) may contain a water insoluble material such as a wax, a fatty alcohol, shellac, zein, polyvinylpyrrolidone, a water insoluble cellulose derivative, ethyl cellulose, a polymethacrylate, or methyl cellulose.

In some embodiments, a particle may contain some active ingredients, referred to as the encapsulants, and some non-active ingredients, referred to as fillers.

In some embodiments, particles may have a boundary wall that defines (and separates) an interior and exterior of the respective particle. The interior may contain an "encapsulant," which is the material inside the particle's boundary, as distinct from the boundary wall itself.

In some embodiments, a boundary wall that defines (and separates) an interior and exterior of the respective particle is made of encapsulant. In some embodiments, a boundary wall that defines (and separates) an interior and exterior of the respective particle is partially made of encapsulant. For example, droplets of CBD oil may be formed in an aqueous solution through emulsification process and the droplet may be stabilized by stabilizing agents. In this example, the boundary may be include (e.g., consist of) a stabilizing agent and CBD oil.

In some embodiments, a boundary wall that defines (and separates) an interior and exterior of the respective particle may be made of, at least in part, a polymeric shell. In some embodiments, there may be a concentration gradient of the encapsulants in the boundary wall. In some embodiments, the concentration of the encapsulants decreases across the boundary wall with higher concentration in regions of the boundary wall closer to the interior and lower concentrations in the regions of the boundary wall closer to the exterior of the particle.

In some embodiments, a particle may not have a defined boundary wall and the encapsulants might be evenly distributed throughout the particle. A particle may be made of filler that serve to retain the shape of the particle while maintaining the encapsulants inside the particle. In some embodiments, there are no chemical or electrical (e.g., ion sharing) reactions between the fillers and the encapsulants. In some embodiments, the particles are held together and the encapsulants are retained within the particles by the structural framework provided by the fillers.

2.1. Miscible Single-Phase Particles

FIG. 1 illustrates a particle 100 containing fillers 101 and encapsulants 102. In some embodiments, fillers 101 may include a solvent that is miscible in the medium surrounding the particle 100, within the particle 100. Fillers 101 may further include a polymer that can inhibit the diffusion and dispersion of the encapsulants 102 in the medium surrounding 103 the particle, like a host beverage in which the particle 100 has been dispersed.

In some embodiments, the permeability of the encapsulants 102 to the surrounding medium depends on many factors including size of the encapsulants 102, pore size of the particle 100, the temperature, viscosity of the fillers 101 and the surrounding medium, and size of the particle 100.

In some embodiments, a particle 100 may be formed by dispersing the encapsulants 102 in a polymer, forming droplets of this mixture and then curing the polymer. For example, a droplet of sodium alginate solution, containing the encapsulants 102, may be added to a solution containing calcium ions. Upon entry of the droplet, alginate chains start crosslinking as the calcium ions diffuse toward the droplet. After sufficient time, the whole droplet with transform to a particle 100 and the encapsulants may be trapped inside a gel of calcium alginate. In another example, an encapsulant 102 may be mixed with a temperature curable polymer and a particle 100 may be formed upon elevating the temperature.

Figure 2:
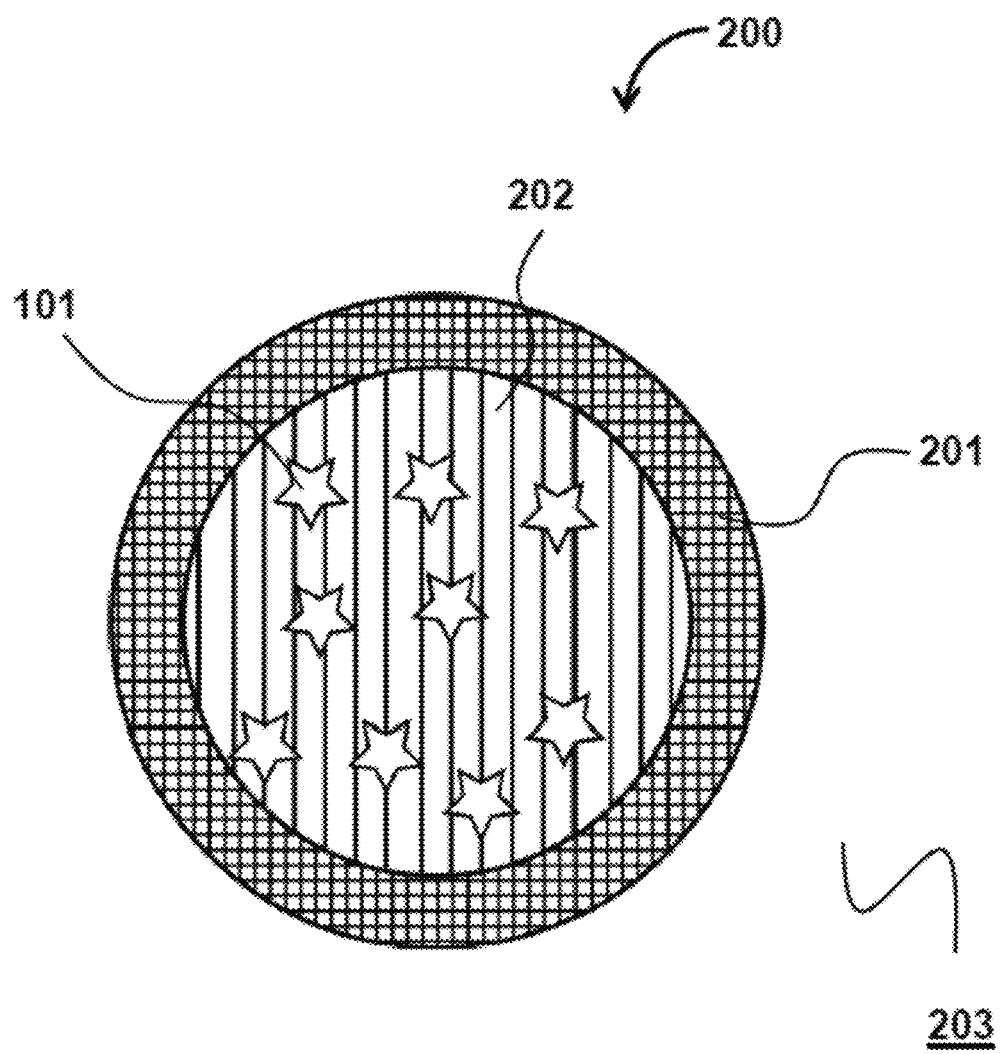
FIG. 2 is a schematic diagram that illustrates a miscible single-phase particle with core-shell structure, in accordance with some embodiments of the present disclosure.

FIG. 2 illustrates a particle 200, having a shell 201 and a core 202, containing encapsulants 102. In some embodiments, both the shell 201 and the core 202 may include a solvent that is miscible in the medium surrounding the particle 200. Each the shell 201 and the core 202 may further included a polymer that can inhibit the diffusion and dispersion of the encapsulants 102 in the medium 203 surrounding the particle. In some embodiments, the shell 201 is configured to have a lower diffusivity coefficient to inhibit the diffusion and dispersion of the encapsulants 102 in the surrounding medium. In particles structurally similar to particle 200, both the shell 201 and the core 202 may be considered fillers.

In some embodiments, particle 200 may be formed by dispersing the encapsulants 102 in a solution, forming droplets of this mixture and then adding these droplets into a polymer solution. For example, a droplet of a solution containing calcium ions and encapsulants 102 (referred to as the first solution) may be added to a second solution containing sodium alginate chains. Upon entry of the droplet to the second solution, the alginate chains in the vicinity of the droplet with start to crosslink as they interact with the calcium ions diffusing from the droplet. Over time, a shell of cross-linked alginate chains may be formed around the droplet. The formed alginate shell may produce a particle 200 containing the encapsulants 102 that are entrapped by the shell 201. The thickness of the shell may depend on many parameters including the concentration of calcium ions, the concertation of sodium alginate in the second solution, temperature, pH, size of the droplet, presence of any other chemical that may affect discussion of calcium ions and alginate chains, and presence of any other chemical that may react with ios or alginate chains.

In some embodiments, a droplet may be formed by various techniques. Droplet formation, in some use cases, is expected to affect encapsulation efficiency and final product stability. Some types of droplet formation are achieved by drop-wise addition of a first solution to a second solution. Drop-wise addition is expected to form big droplets in the size range of a few centimeters (again, discussion of which is not to be read as a disclaimer of any subject matter). In some cases, the drops may have the size properties of the particle discussed above.

Some embodiments are expected to mitigate these issues with drop-wise addition by using a tube with an orifice, like pipettes, needles, or micro needles (which may be generally referred to as pipettes) to form the droplets in the size range of a millimeter or less (or the other size ranges discussed above). In some embodiments, food-grade pressure pumps (such as syringe pumps, and peristaltic pumps) fluidically couple a reservoir of the first solution to an orifice disposed within or above a second reservoir of the second solution. The orifice may have a diameter in the range of hundreds of micrometers, and the orifice may generally have a circular or oval shape. The pressure pump may be coupled to an actuator configured to pump the first solution into the second solution at a volumetric flow rate of 1-1000 ml per minute per orifice. In operation, the pump may push the first solution from the first reservoir and introduce it to the second solution in the second reservoir in the form of droplets.

In some embodiments, a particle 200 may be formed by a reverse spherification process. Reverse spherification is best understood with contrast to direct spherification. In direct spherification, a drop of the encapsulants by a film of non-calcium alginate is dropped into a bath containing a source of calcium ions. On the other hand, in reverse spherification, the encapsulants may be first mixed with a source of calcium or magnesium ions, for example, calcium chloride. This phase is referred to as first phase or interior phase. If the encapsulants is a liquid food product, the calcium or magnesium salt may be used to avoid affecting the flavor of the liquid food product. Next, a drop or other quantity of a monolithic body of the first phase may be formed with the mixture including the encapsulants and the calcium or magnesium ions. The drop may then be introduced (e.g., as a drop falling through air down into a volume of liquid, or formed immersed within such a receiving volume of liquid) into a solution containing a non-calcium alginate, for example, sodium alginate. This solution is referred to as the second phase or exterior phase. When a surface of the formed drop containing calcium ions comes into contact with the solution containing alginate, a semi-solid and gelatinous film may be formed almost instantaneously, which contains in its interior the encapsulants.

In some embodiments, sodium alginate (e.g., in the range of 0.01 to 1 wt %) may added to the first phase immediately before addition to the second phase. Presence of alginate chains inside the particle may help with structural stability and delayed release kinetics. In some other embodiments, other types of polymers, instead of alginate chains are added to the first phase.

2.2. Immiscible Single-Phase Particles

In some embodiments, manufacturing a particle may include obtaining an oil-in-water (O/W) emulsion. O/W emulsions may include liquid oil droplets dispersed in a continuous liquid water phase. O/W emulsions may be formed from two immiscible or nearly immiscible water and oil phases. The oil phase may include a lipophilic solvent or a suspension carrier. The oil phase may further include water-immiscible or nearly water-immiscible encapsulants. The oil phase may further include surfactants and emulsifiers that may facilitate the formation of O/W emulsions by decreasing the interfacial tension between the water and oil phases and further decreasing the energy input required to form O/W droplets. The surfactants may further stabilize the O/W emulsions. The surfactants may include hydrophobic segments that orient in the oil phase and a hydrophilic segment that orient in the water phase. The surfactants or emulsifiers may enhance the stability of the O/W emulsions. The water phase may also contain surfactants or emulsifiers that may facilitate the formation of O/W emulsions by decreasing the interfacial tension between the water and oil phases and further decreasing the energy input required to form O/W droplets.

O/W emulsions may be made by pre-processing the oil phase and water phase with a variety of techniques prior to combination. In some embodiments, the oil phase may be heated to 50° C., 70° C., 90° C., 110° C., 130° C., 150° C., 200° C., or 250° C. prior to emulsification. This may be done to dissolve various types of fillers (e.g. surfactants, polymers, and waxes) and encapsulants. In some embodiments, the water phase may be heated to heated to 50° C., 60° C., 70° C., 80° C., 90° C., or 95° C. prior to emulsification. In some embodiments, the heating process may be done to dissolve various types of fillers (e.g., surfactants). In some embodiments, the heating process may be performed at ambient pressure. In some embodiments, the heating process may be performed at pressurized containers (e.g. 1.5 atm, 2 atm, 5 atm, or 10 atm). In some embodiments, the heating process may be done to control the viscosity of the oil phase. Temperature ranges may be selected based on the type and amount of chemicals being added to the oil phase or to the water phase. For instance, for some of the types and amounts of surfactant described below, temperatures outside these ranges are expected to cause either incomplete solubility (or miscibility) below the low end of the temperature range, or degradation of the chemical structure of the surfactant molecule above the high end, none of which is to suggest that any subject matter is disclaimed, either here or elsewhere in this document.

In some embodiments, emulsification may be carried out at room temperature (herein defined as 25° C.).

In some embodiments, emulsification may be carried out at temperatures above room temperature, e.g., between 26 to 100° C. In some embodiments, the emulsification temperature (of the combined input phases) may be between 30 to 80° C. In some embodiments, the emulsification temperature may be between 40 to 60° C. Emulsification in temperatures above room temperature may be done to reduce the viscosity of oil and water phases. This may be done to reduce the interfacial viscosity between the oil and water phases. In some embodiments, emulsification in temperatures above room temperature may be done to provide better mixing of the oil and water phases by tuning the viscosity or density of the phases.

In some embodiments, emulsification may be carried out in temperatures at or below room temperature. In some embodiments, the emulsification temperature may be between 1 to 24° C. In some embodiments, the emulsification temperature may be between 5 to 20° C. In some embodiments, the emulsification temperature may be between 10 to 15° C. This may be done to reduce the collision rate of formed droplets, which may produce a more stable emulsion than higher-temperature processes. Emulsification in temperatures below room temperature may be done to avoid overheating and subsequent destabilization of the emulsion.

In some embodiments, the oil phase (e.g., prior to introduction to the water phase) comprises a lipophilic solvent or suspension carrier. In embodiments where the immiscibility of the water and oil phases is of importance, lipophilic solvents may be selected. In embodiments where the oil-soluble encapsulants' stability in the oil phase may be affected, a compatible suspension carrier may be selected.

In some embodiments, the volume ratio of the oil phase to water phase may be between 1:1 to 1:20. In some embodiments, the volume ratio of the oil phase to water phase may be between 1:2 to 1:15. In some embodiments, the volume ratio of the oil phase to water phase may be between 1:3 and 1:4. In some embodiments, the volume fraction of the dispersed phase (e.g., oil) is reduced to achieve smaller droplet size. This reduction may be done so as to decrease emulsion viscosity. This reduction may be done so as to increase emulsifier availability per droplet. This reduction may also be done so as to protect the O/W emulsions against coalescence due to reduced rate of collision frequency.

In some embodiments, where *cannabis* extract or isolate is among the encapsulants, the amount of carrier oil in the formulation may exceed that of the *cannabis* extract or isolate. In some embodiments, the oil phase may include 50-60 w/w % long chain triglycerides (LCT) to prevent or impede Ostwald ripening as well as to help achieve smaller droplet size.

In some embodiments, cannabidiol (CBD) may be dispersed in the carrier oil of the oil phase, as an encapsulant. The concentration of CBD in the oil phase may range between 1 to 40 w/w % (percentage weight of CBD to weight of oil phase). In some embodiments, the concentration of CBD in oil phase may range between 5 to 50 w/w %. In some embodiments, the concentration of CBD in oil phase may range between 10 to 25 w/w %. Higher CBD concentrations may result in higher CBD loading per oil droplet.

An example procedure for producing CBD-containing emulsions may include the following steps: first, an oil phase and an aqueous phase may be prepared separately under continuous magnetic stirring at about 80 and 50° C. respectively. The oil phase may consist of medium-chain triglyceride (MCT) oil or other biocompatible oils and various types of surfactants. The aqueous phase may contain additives, such as hydrophilic surfactants (e.g., tween 20) or glycerol. All components may be completely dissolved. Subsequently, the two phases may be combined and mixed with a mechanical mixer. This pre-homogenization can be performed by employing a high-shear rotor-stator device such as an Ultra-Turrax available from IKA®-Werke GmbH & CO. KG of Staufen, Germany. Thus, a homogenous, but coarse emulsion with droplet sizes of a few microns may be produced. This pre-emulsion may be further stirred and re-heated to around 50° C. Although higher temperatures of over 90° C. have been used for this production step, moderate heating may be used to avoid degradation of phospholipids. The emulsion may then be processed with a high-pressure homogenization device, such as a high-energy ultrasonicator.

In some embodiments, the emulsions may be stabilized by surfactants. Surfactants may include a lipophilic segment and a hydrophilic segment, which may facilitate the formation of oil droplets dispersed in the continuous water phase. In some embodiments, the emulsions are stabilized by stabilizers. The stabilizers may be non-surface-active macromolecules that are added to increase the viscosity of the continuous phase and that reduce the mobility of the droplets in order to prevent the droplets from coalescing. In some embodiments, the continuous phase is the phase in which the particles are dispersed in after purification and rinsing. In some other embodiments, the continuous phase is the exterior phase in the emulsification.

In some embodiments, a single surfactant system is used to form oil-in-water particles. In some embodiments, the surfactants are dispersed in the oil phase. Soybean lecithin is an example of an ingredient suitable for such a system. In some embodiments, the surfactants are dispersed in the water phase. In some embodiments, the surfactants are dispersed in both oil and water phases.

In some embodiments, the viscosity of the dispersed phase (internal phase) is expected to influence droplet disruption. In some embodiments, the viscosity of the continuous phase (external phase) is expected to not influence droplet disruption, provided energy density is constant and coalescence is avoided.

In some embodiments, a weighting agent is added to the oil phase. In some embodiments, the addition of the weighting agent is to match the density of the oil phase with the density of the water phase. Examples of such weighting agents are sucrose acetate isobutyrate ester gum, brominated vegetable oil, or any other oil soluble ingredient with densities higher than water.

In some embodiments, the oil phase is an oil that is water-immiscible or has very low water solubility (e.g., less than 1 gram in 100 grams of water, or less than 5 grams in 100 grams of water, or less than 10 grams in 100 grams of water). Examples of such oils include cannabidiol (CBD) oil, hemp oil, soybean oil, safflower oil, sunflower oil, castor oil, corn oil, olive oil, palm oil, peanut oil, almond oil, sesame oil, rapeseed oil, peppermint oil, poppy seed oil, canola oil, hydrogenated vegetable oils, fish oil, borage oil, palm kernel oil, hydrogenated soybean oil, coconut oil, cottonseed oil, glyceryl esters of saturated fatty acids, glyceryl behenate, glyceryl distearate, glyceryl monolinoleate, glyceryl palminate, glyceryl palmitostearate, glyceryl ricinoleate, glyceryl stearate, polyglyceryl 10-oleate, polyglyceryl 3-oleate, polyglyceryl 4-oleate, glyceryl isostearate, glyceryl laurate, glyceryl monooleate, polyglyceryl 10-tetralinoleate, behenic acid, caprylyic/capric glycerides, and any combinations thereof.

In some embodiments, the oil and water phases are heated to 70-250° C. and 40-90° C. prior to emulsification, respectively. In some embodiments, the oil and water phases are cooled to lower temperatures (e.g. room temperature or 50° C.) prior to emulsification.

In some embodiments, a rotor stator mixer is used to prepare the emulsions. The rotation of the impeller may impart high-shear force to the immiscible phases and causes the formation of oil droplets in a continuous water phase.

The carrier oil may be selected from a group of food-grade medium-chain triglycerides (MCTs, e.g., coconut oil) or long-chain triglycerides (LCTs, e.g. olive oil). The oil phase may contain the encapsulants (e.g., CBD), and the encapsulants content may range between 5-50 wt % of the particle. In some embodiments, the amount of carrier oil in the formulation may somewhat exceed that of the encapsulants.

In some embodiments, the volume fraction of the dispersed phase (e.g., oil) is minimized to achieve smaller droplet size. This may be due to decrease in emulsion viscosity, increased emulsifier availability per droplet (e.g. particle), and protection against coalescence due to reduced rate of collision frequency.

In some embodiments, the phases are added to a working volume of a high-shear rotor-stator device that is used to create O/W emulsions. A variety of stirrers, blenders and homogenizers may be used for the purpose of creating emulsions. The final size and distribution of particles may be directly influenced by the size and polydispersity index (PDI) of emulsion droplets.

In some embodiments, the mechanical mixer is a rotor-stator device with a speed that is set to between 6,000 to 12,000 RPM. In some embodiments, the dispersed (e.g., oil) phase may be added in a drop-wise fashion to the continuous phase (e.g., aqueous phase).

In some embodiments, the emulsification is performed in an ice bath so that the agitation is carried at a temperature below room temperature. In some embodiments, the emulsification is performed in an oil bath with a temperature above room temperature.

Figure 3:
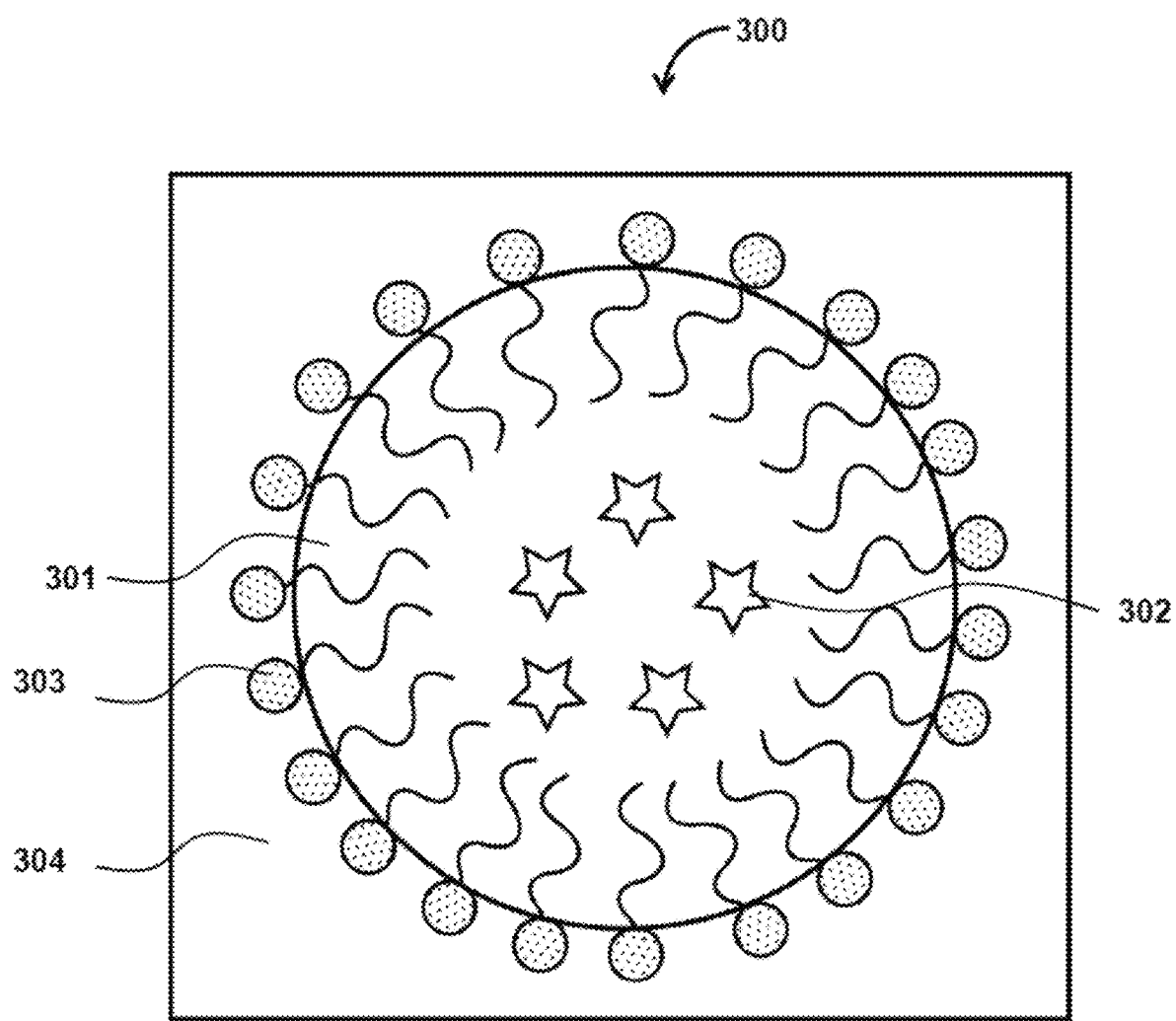
FIG. 3 is a cross section view of an immiscible single-phase particle, in accordance with some embodiments of the present disclosure.

FIG. 3 illustrates an example cross-section of a particle 300 formed by oil-in-water emulsification. The O/W droplets consists of an oil phase 301 which contains encapsulants 102. The hydrophobic part of the surfactants 303 may be positioned in the oil phase 301, while the hydrophilic segment of the surfactant 304 may be positioned in the water phase 304.

In some embodiments, a particle formed from a droplet with some stabilizing agent (e.g., surfactant) placed in the interphase of the droplet and the surrounding medium.

In some embodiments, the oil phase may be the continuous phase and the water phase may be the dispersed phase.

2.3. Immiscible Double-Phase Particles

Figure 4:
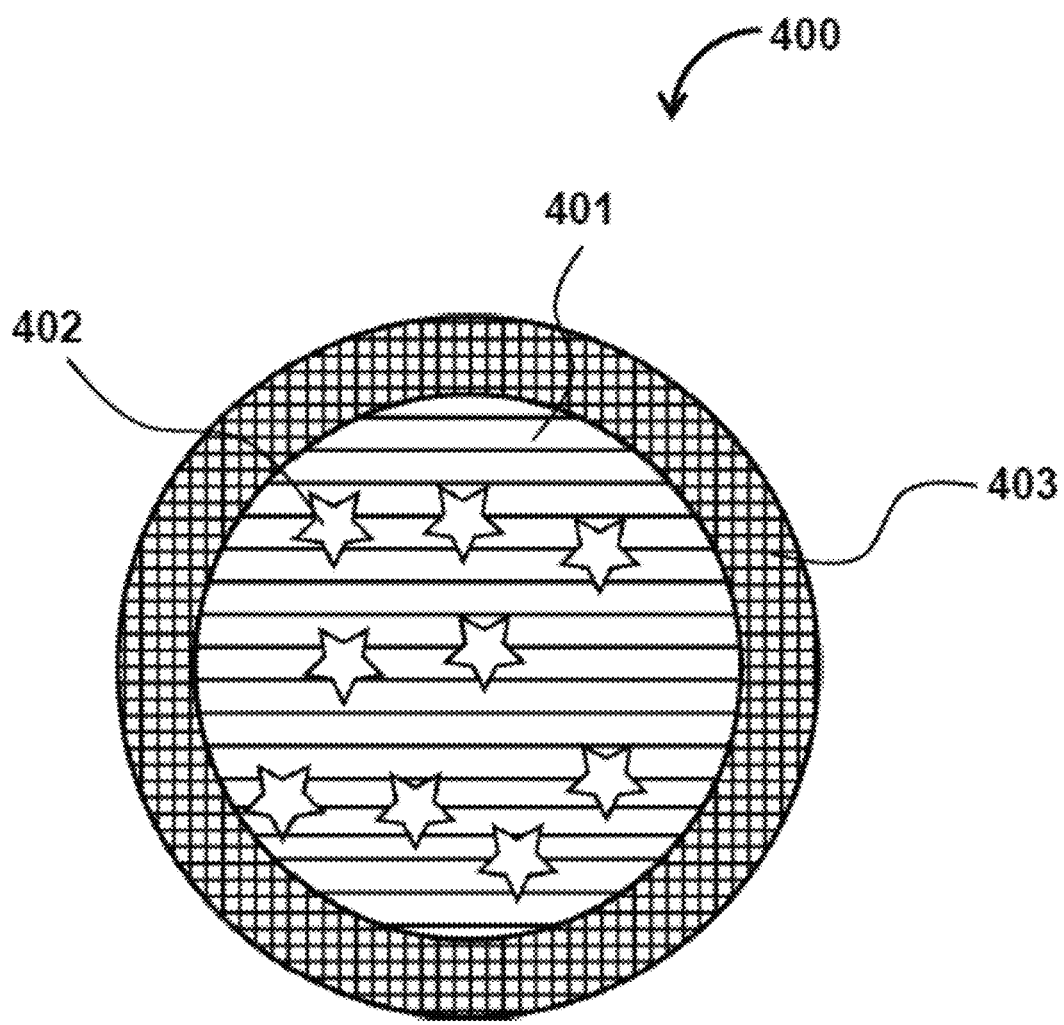
FIG. 4 is a cross section view of an immiscible double-phase particle with core-shell structure, in accordance with some embodiments of the present disclosure.

FIG. 4 illustrates an example cross-section of a particle 400 with two layers. Such particles 400 may include a core 401, which may contain encapsulants (e.g., a payload) 402, and a shell 403. In some embodiments, the shell 403 does not contain any encapsulants. In some embodiments, the shell 403 also contain encapsulants.

Figure 5:
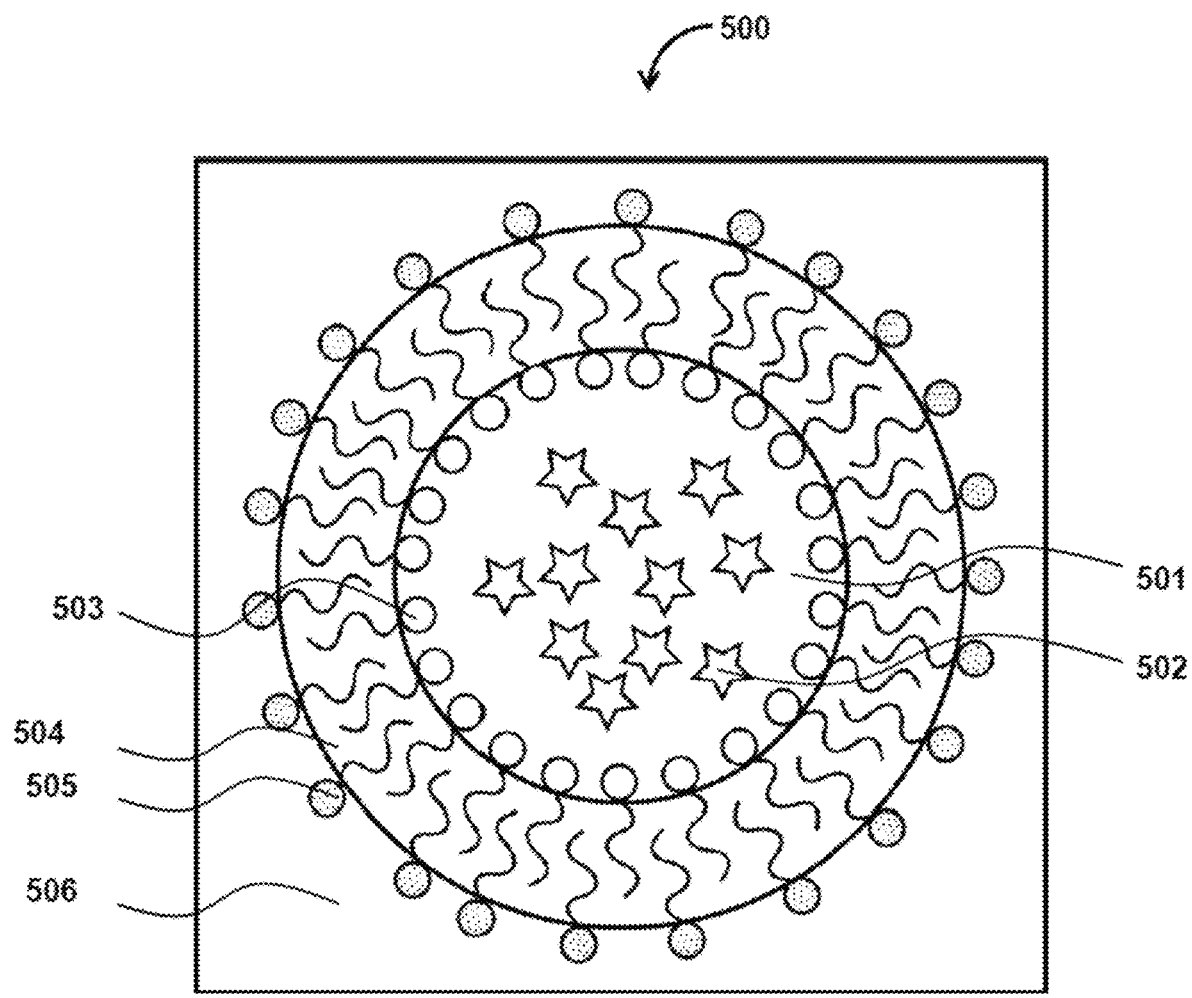
FIG. 5 is a cross section view of a W/O/W droplet, in accordance with some embodiments of the present disclosure.

In some embodiments, a particle 400 may be formed by a double emulsion process. FIG. 5 illustrates an example cross-section of W/O/W droplets 500. The W/O/W droplets may include an inner water phase 501 that contains encapsulants (e.g., payload or active ingredients) 502. The hydrophobic part of a first type of surfactant 503, stabilizing the W/O emulsion, may be positioned in the oil phase 3104, while the hydrophilic segment of the surfactant 3103 may be positioned in the inner water phase 501. The hydrophobic part of a second type of surfactant 505 stabilizing the W/O/W droplets may be positioned in the oil phase 504, while the hydrophilic part of the surfactant 505 may be positioned in the outer water phase 506.

In some embodiments, particles 400 may be packaged or added to additional alimentary products before packaging. In some cases, flavoring agents are added. In some cases, the packages are liquid containers of less than 50, 10, 5, 1, or 0.5 liters in size made of plastic, aluminum, glass, or cardboard. In some cases, the container may have an interior lining. In some cases, the resulting beverage is shelf stable for more than 2 days, 7 days, 14 days, 1 month, 2 months, 6 months, or 12 months in these containers at room temperature or cold chain (e.g. below 15° C., 10° C., or 5° C.). In some cases, the filled containers may be distributed to retail stores, placed on shelves, and sold, or distributed directly to other businesses or consumers.

In some embodiments, the particles similar to the particle shown in FIG. 4 are packaged in 2 oz. (or 1 oz.) format to deliver 20 mg ionic zinc, 1000 mg vitamin C, 600 IU and vitamin D3. In some embodiments, the 2 oz. format contain 20 mg CBD as well.

In some embodiments, particles are added to a beverage and packaged in 1 ml, 1.2 ml, 1 oz., 8 oz., 16 oz. or 24 oz.

In some embodiments related to water/oil/water (W/O/W) emulsions, a lipophilic emulsifier 503 may be used to prepare the primary W/O emulsion and a hydrophilic emulsifier 505 to prepare the secondary emulsion. The fundamental molecular and colloidal factors influencing the coalescence stability of the inner and outer droplets, when considered separately and in isolation, are similar to those for simple W/O (water in oil, having oil as the continuous phase) and O/W (oil in water, having water as the continuous phase) emulsions, respectively. However, there is the additional aspect involved with in the W/O/W emulsion that the emulsifiers of different hydrophile-lipophile balance tend to have a destabilizing effect on each another. Ideally, the lipophilic emulsifier would remain located entirely at the inner oil-water interface. But, in practice, in order to be able to make the primary emulsion droplets sufficiently small, it is often helpful for the lipophilic emulsifier to be present at rather high concentrations in the oil phase. In the self-assembled form of aggregates and reverse micelles, this excess lipophilic emulsifier may enhance the solubilization and mass transport of water-soluble compounds (including ions) through the oil phase. In addition, some of the excess lipophilic emulsifier inevitably migrates to the outer oil-water interface, thereby undermining the stabilizing ability of the hydrophilic secondary emulsifier.

Relevant to some embodiments, a stability parameter characterizing the effectiveness of any double emulsion formulation is the 'yield.' This is the percentage of primary emulsion aqueous phase that is retained as internal aqueous phase in the W/O/W emulsion following the second-stage emulsification. The yield may be determined by measuring the extent of accumulation in the outer continuous phase of a marker compound originally present in the aqueous phase of the primary W/O emulsion.

An initial yield of 100% would mean that all the dispersed aqueous phase of the original primary emulsion remained undisturbed during the second emulsification stage. In practice, the initial yield value typically lies below this ideal theoretical limit. This is because of the disruption of some inner droplets induced by the hydrodynamic conditions present during the secondary emulsification stage, in many embodiments. During storage of a double emulsion, there may be then a gradual fall in the value of the percentage yield as the internal aqueous phase is released into the external continuous phase.

Some embodiments include W/O/W emulsions containing an inner water phase. The inner water phase may be aqueous or gelled. The inner water phase may contain encapsulants. The inner water phase may contain surfactants. The inner water phase may contain various type of macromolecules and polymers. The oil phase may contain surfactants, encapsulants, and various type of macromolecules and polymers. The outer water phase may contain surfactants, stabilizers and various type of macromolecules and polymers. W/O/W particles may mask the flavor of the encapsulated components and make the taste of those components almost unnoticeable for a consumer in an alimentary product containing the W/O/W emulsions.

In some embodiments, the particles may be used to mask the flavor of the encapsulated components during consumption by a consumer. For example, the bitter taste of vodka can be masked in a beverage by encapsulating the vodka in the particles and dispersing them in a beverage. As a consumer is drinking the beverage, the taste of vodka is significantly masked, and the consumer mainly tastes the flavor of the beverage. In contrast, in the absence of such particles, the taste of vodka would be much stronger at the same concentration. In some embodiments, the particles have a polymer shell that can delay the release of encapsulated components to the solution in which the capsules are dispersed. This provides a timeframe for a consumer to drink such a solution without tasting the flavor of the encapsulated components.

In some embodiments, the inner water phase may contain proteins as encapsulants. The concentration of proteins may range between 1-80 wt %.

In some embodiments, the solvent for the aqueous phase in the primary W/O emulsion may include water, a mixture of ethanol and water, or pure ethanol.

In some embodiments, to stabilize the primary W/O emulsion, polyglycerol polyricinoleate (PGPR) may be used. This particular lipophilic emulsifier may be used in the formulation of W/O/W emulsions for food-based applications. This synthetic emulsifier is polyglycerol ester of polyricinoleic acid. PGPR is expected to be effective for stabilizing fine W/O emulsions made with triglyceride oils.

In some embodiments, to stabilize the primary W/O emulsion, PGPR concentration of 0.1-10 wt % may be used in the lipophilic part of the emulsion. In some embodiments, PGPR concentration may range between 2-8 wt %. In some embodiments, PGPR concentration may range between 4-6 wt %.

In some embodiments, to stabilize the W/O emulsions, phosphatidylcholine-depleted lecithin may be used as an alternative to addition to to PGPR (which is not to suggest that other described features are not also amenable to variation).

In some embodiments, polymers may be used to stabilize the double emulsions. Three expected benefits of using polymers as stabilizing ingredients in double emulsions are:

a. Compared with small-molecule emulsifiers, polymers are much less susceptible to diffusion and migration from internal to external aqueous phases, or vice versa;

b. Polymers may readily form stabilizing network structures in the dispersed and continuous aqueous phases, e.g., viscoelastic solutions and gels; and c. Surface-active biopolymers may be used as effective stabilizers of the outer oil-water interface of W/O/W emulsion droplets.

In addition to the technical benefits (mention of which is not intended to suggest that embodiments not affording these benefits or other benefits discussed herein are disclaimed), the incorporation of polymers (e.g., biopolymers) as functional ingredients in double emulsions may allow for the reduced use of synthetic emulsifiers in such formulations and possibly even for their complete elimination from food-and-beverage based applications.

Various food biopolymers may be used in W/O/W. Examples include gelatin, casein, whey protein, bean protein, acacia gum, and xanthan. These biopolymers may increase the yield of encapsulation and also improve both quiescent and shear-induced coalescence stability, though again, embodiments exhibiting lower yield and not using this technique are also contemplated, which is not to suggest that any other aspect of this disclosure is limiting.

In some embodiments, polylactide, polyglycolide, and their copolymers poly(lactide-coglycolide), polycaprolactones, polyacrylates, or nonbiodegradable such as: polyacrylics, poly(vinyl chloride-co-acetate) and polystyrene are used. For instance, polyesters may be used for drug delivery due to their biocompatibility and biodegradability.

In some embodiments, a combination of PGPR and biopolymers may be used to stabilize the primary W/O emulsions.

In embodiments where a combination of PGPR and biopolymers may be used to stabilize the primary W/O emulsion, the same encapsulation yield may be achieved even at a lower concentration of PGPR. For instance, in W/O emulsions prepared with PGPR as lipophilic emulsifier, the incorporation of 0.5 wt % of sodium caseinate in the internal aqueous phase is expected to allow a reduction in the PGPR content from 6 to 3 wt % without affecting the yield or stability.

In some embodiments where biopolymers are used as additional stabilizers, the initial yield may increase with increasing biopolymer concentration. The combination of caseinate+PGPR may produce a more viscoelastic adsorbed layer which resists the release of the encapsulants from the inner droplets. Another functional role of sodium caseinate in W/O/W emulsions may be as a chelating agent which may reduce the rate of release of encapsulated multivalent cations (e.g. ionic zinc, ionic magnesium, ionic iron, etc.).

In some embodiments, a polymer shell may be coated on the particle to control the release kinetics of the encapsulated ingredients. The release kinetics may be controlled by tuning the thickness of the polymeric shell, the dissolution rate of the polymer in the digestive tract, or the pore sizes of the polymeric shell. Examples of such polymers are sodium alginate and polyethylene glycol.

In some embodiments, the inner aqueous phase may be converted into soft solid-like phase to provide long-term stability to the inner emulsion W/O droplets. This may be achieved using a biopolymer that is readily converted to the gel state (e.g. by thermal processing). Adopting this approach, a W/O/W emulsion containing a heat-set gel of whey protein in the inner droplets can be successfully prepared by incorporating whey protein isolate (e.g. WPI; 15 wt %) in the primary W/O emulsion and then subjecting the W/O emulsion to thermal treatment (80° C. for 20 min) prior to secondary emulsification. Another example of polymer may be agar to be incorporated in the inner aqueous phase.

In some embodiments, the gelation of a solution of gelatin (5 wt %) encapsulated in the internal aqueous phase is exploited in order to control stability and encapsulation efficiency. Double emulsions with gelled starch within the inner droplets generally show improved stability. The emulsification of the aqueous phase in the oil may be performed at a temperature (e.g., 85° C.) above the melting temperature of the starch gel, and subsequent gelation may be induced by cooling. In some embodiments, cooling may be performed quickly (e.g., more than 10° C. drop in temperature per minute). In some other embodiments, the cooling rate may be slower (e.g., less than 5° C. drop in temperature per minute). A benefit of starch incorporation is expected in terms encapsulation efficiency: The measured release rate of a hydrophilic compound (e.g., alcohol or protein) from the internally gelled W/O/W emulsions expected to be slower than for the equivalent non-gelled emulsions. However, it should be noted that the presence of the starch may lead to some complications in the formulation of the double emulsion. The high viscosity of the aqueous phase increases the amount of surfactant needed for the emulsification and stabilization of the W/O droplets. An additional factor contributing to greater surfactant demand is some complexation between the starch and the non-ionic surfactants (span 80 and tween 20).

In some embodiments, another biopolymer-based material that may be incorporated in the internal aqueous phase of a W/O/W emulsion is microcrystalline cellulose.

In some embodiments, emulsification of the primary W/O emulsion may be carried out in room temperature. In some cases where heat-sensitive components (e.g., ethanol) are present in some embodiments, the emulsification temperature may be kept close to room temperature (e.g., ±5° C. of room temperature as defined above) to avoid or reduce potential loss of the aqueous phase.

In some embodiments, where alcohol is present in the aqueous phase, LCTs (e.g., olive oil) may be used as the oil phase solvent, for instance, to avoid or reduce the solubility of the aqueous and oil phases.

In some embodiments, the carrier oil may be food-grade. In some embodiments, the carrier oil may be selected to not adversely affect product quality (such as appearance, taste, texture, or stability). In some embodiments, the carrier oil may protect from chemical degradation during storage. In some embodiments, the carrier oil increases bioavailability after ingestion. Carrier oils are expected to be beneficial in stabilizing the emulsion from Ostwald ripening, which is a major de-stabilization mechanism in nano- and micro-emulsions (again, which is not to suggest that embodiments without such carrier oils are not also contemplated). Ostwald ripening is a process in which very finer droplets of emulsion dissolved into continuous phase, diffuse and redeposit upon larger droplets, thus increasing the average size of emulsion droplets. Ostwald ripening occurs because of the increased solubility of the dispersed phase (e.g., oil) into the aqueous phase. This challenge can be addressed (e.g., mitigated or eliminated) by the introduction of hydrophobic properties into the dispersed phase.

In some embodiments, hydrophobicity of the oils may be improved by introducing a mixture of oils to produce micro- and nano-emulsions. Such mixtures are expected to be suitable to tune the hydrophobicity to the point where a desired size or stability is reached for the dispersed droplets.

In some embodiments, the oil-to-water ratio by volume is between 1:1 to 1:9. In addition to volume ratio, dispersed-to-continuous (e.g., oil-to-water) phase viscosity ratio may be considered for preparing stable emulsions.

In some embodiments, a high-shear rotor-stator device may be used to create coarse W/O emulsions. A variety of stirrers, blenders and homogenizers may be used for the purpose of creating emulsions (e.g. nano emulsions or micro emulsions). The size of coarse emulsion droplets is generally in the range of 1-25 µm, depending on the type of device and external energy input. The final size and distribution of particles may be directly influenced by the size and polydispersity index (PDI) of coarse emulsion droplets.

In some embodiments, proteins may be used as emulsifiers for the secondary emulsions. Proteins are expected to be highly effective as secondary emulsifying agents and as stabilizers of the outer droplets of W/O/W emulsions. The underlying principles of the steric and electrostatic stabilization of double emulsion droplets by protein are the same as those relating to a simple protein-stabilized emulsion. A further advantage of protein as emulsifying agent is expected to be that it is insoluble in the oil phase, and so it has little or no tendency (unlike small-molecule emulsifiers) to migrate to the internal oil-water interface or to interfere with the stabilization of the inner droplets. In the case of O/W emulsions, some embodiments may add polysaccharides at low concentrations as thickening and gelling agents in order to achieve rheological control of the aqueous continuous phase; the same approach may be applicable to double emulsions.

Various different types of food protein emulsifiers may be employed in the stabilization of double emulsions, including sodium caseinate, gelatin, BSA and whey protein isolate and also some hydrocolloid emulsifiers such as gum Arabic and hydrophobically modified starch. To stabilize the outer droplets of double emulsions, various soluble polysaccharides may be utilized acting as thickening/gelling agents; pectin, carrageenan, alginate, xanthan, gellan, locust bean gum and carboxymethylcellulose—and also using colloidal particles of microcrystalline cellulose. The presence of a hydrocolloid such as maltodextrin or gum Arabic in the external aqueous phase may be helpful for a W/O/W emulsion that is to be converted into microcapsules by spray drying. With sodium caseinate as the secondary emulsifying agent, high-pressure homogenization may produce fine W/O/W emulsions and a relatively high yield.

The protein component of gum Arabic (*Acacia senegal*) is expected to confers upon this food hydrocolloid a distinctive surface activity and emulsifying properties. This same functionality can be exploited in the stabilization of the outer droplets of W/O/W emulsions. But, in contrast to a protein emulsifier such as sodium caseinate, concentrations of around 10 wt % of the gum are helpful in order to achieve the preparation of fine double emulsions with good long-term stability.

In some embodiments, the combined advantages of proteins and hydrocolloids as functional ingredients may be used through the preparation of protein—polysaccharide complexes for use as emulsifying and stabilizing agents. In these mixed biopolymer complexes, the constituent protein and polysaccharide molecules may be joined together permanently (via covalent bonding) or reversibly (involving electrostatic interactions). The formation of protein-polysaccharide hybrids by controlled dry heating may be particularly convenient and beneficial for making covalent conjugates for use in food-related applications. This Maillard-type conjugation induced by the dry-heat treatment is expected to lead to improvement in protein solubility and emulsion stability under unfavorable solution conditions of low pH and high ionic strength. This improved functionality is believed to be due to the increased hydrophilicity of the conjugate and its better steric stabilizing ability as compared with the protein alone.

In some embodiments, combinations of proteins and polysaccharides that form soluble electrostatic complexes are expected to provide improved stability properties of O/W emulsions over a wide range of environmental conditions. Depending on the biopolymers involved and the methods used to prepare the emulsions, the oil droplets may be coated by composite layers or multilayers having enhanced electrosteric stabilizing properties as compared with pure protein-stabilized emulsions. It is expected that the same approach is also applicable to the stabilization of W/O/W emulsions.

Various mixtures of protein+polysaccharide may be used with a purpose of generating outer droplets of W/O/W emulsions that are stabilized by protein-polysaccharide complexes. In particular, for instance, the stabilization of the external oil-water interface of double emulsions by complexes of WPI+xanthan gum and WPI+galactomannans (locust bean gum, guar gum and fenugreek gum) may be achieved.

In some embodiments, the nature of the composition of the emulsion may be altered in order to minimize or reduce an amount of the composition's calories. The reduction in size or number of oil droplets may result in loss of physical consistency and sensory properties. To mitigate this effect, in some embodiments, the same oil droplet size and number may be retained, but their inner part may be substituted with water. In some embodiments, the encapsulation efficiency may be sacrificed to reduce the calorie content of a particle.

In some embodiments, low-intensity homogenization is used to prepare the secondary emulsion in order to avoid emulsion breakdown. In the initial stage of double emulsion preparation, a homogenizer of the rotor-stator type may be used to prepare the W/O (or O/W) primary emulsion. The emulsion premix may then be subjected to high-pressure homogenization in order to accomplish a further substantial reduction in the mean droplet size of the inner W1 (or O1) phase. Rotor-stator equipment may be used also for the secondary emulsification step, but in this case under more moderate dispersing conditions so as to try to avoid hydrodynamic conditions of intense shearing or turbulence, which may cause destabilization of the previously formed primary emulsion. Other emulsification devices that may be used during the second stage include sonicators (operating at moderate ultrasound intensity) and high-pressure homogenizers (operating in a reduced pressure range).

For reliable processing during secondary emulsification, it may be helpful in some embodiments to inhibit any flow-induced coalescence of internal droplets with the external phase by avoiding the application of intense hydrodynamic forces. In some implementations, this may involve setting the applied pressures in 1-stage and 2-stage valve homogenizers well below the values typically employed in the preparation of a micron-sized food O/W emulsion like homogenized milk.

In some embodiments, shell thickness of a particle may be 50%, 20%, 10%, or 5% of the radius of the particle.

In some embodiments, particles may have an inner volume and a boundary wall surrounding the inner volume. In some embodiments, the particles may have a spherical shape. In some embodiments, the particles may have a non-spherical shape. For example, the particles may have a teardrop or double teardrop shape.

In some embodiments, the particles may have a double shell. In some embodiments, the interior shell is an oil phase surrounding a droplet (e.g., aqueous droplet or gelled phase) in which the components to be encapsulated are dispersed. In some embodiments, the exterior shell is a polymeric shell. Such polymeric shell may be used to control the release kinetics of the encapsulants, stabilize the particle in the surrounding medium, or reduce the permeation of the encapsulants.

In some embodiments, the particles may have multiple shells. In some embodiments, shells may each contain similar or different types of encapsulants. Incorporation of encapsulants at different shell may be performed to control the release kinetics, prevent interaction of the different types of encapsulants, or load different types of encapsulant, with different solubility properties (e.g., oil soluble and water soluble), in a single particle.

In some embodiments, the encapsulants are immiscible in water. In such instances, in some embodiments, the encapsulants are first mixed with an organic solvent or an oil phase; this phase may act as the interior phase or one of the shells of a particle.

In some embodiments, a combination of polymers may be used as fillers in the interior phase or one of the shells of a particle. For example, a secondary polymer such as chitosan may be used in addition to alginate, resulting in a polyelectrolyte complex between alginate and chitosan that may improve the stability of the particles and reduces the porosity of them.

In some embodiments, a polymeric shell is formed around the droplet of the oil phase after the second emulsification. In some embodiments, the polymeric shell may be alginate chains. Cross linking and polymerization of a polymer are terms used interchangeably throughout this disclosure. In some embodiments, the alginate is expected to form a shell and cross link around the droplet of the oil phase because of the diffusion of the divalent salts such as calcium from the droplet of the oil phase. In some embodiments, the divalent salt is dissolved in the oil phase before the first emulsification. In some embodiments, the divalent salt is dissolved in the oil phase after the first emulsification. In some embodiments, both the first and the second water phases comprise polymer chains and, therefore, the particle may have an interior in gelled phase and a shell with an oil layer and then a polymer on the exterior. In some embodiments, the polymer chains may be polymerized after the second emulsification process. In some embodiments, the polymer chains are alginate chains. In some embodiments, the alginate may be polymerized by the diffusion of the calcium ions, dissolved in the oil phase, to the first and second water phases.

In some embodiments, a polymer may be dissolved in the oil phase before or after the first emulsification. In some embodiments, the polymer dissolved in the oil phase may be polymerized before or after the first emulsification to form a polymeric shell surrounding a droplet of the first water phase. In some embodiments, the emulsification processes may be performed at temperatures higher than the melting temperature of dissolved polymer in the oil phase. Once the particles are formed, the temperature may be reduced to solidify the dissolved polymer and consequently solidify the oil phase. Similar strategy may be used to incorporate a polymer in the inner aqueous phase (e.g., agar) and solidify the inner aqueous phase by reducing the temperature after the emulsification steps.

In some embodiments, the oil phase may be partially removed after the second emulsification. In some other embodiments, the oil phase may be almost completely removed after the second emulsification. Removal of the oil phase may be done to reduce the calory content of the particle.

In some embodiments, the oil phase may be kept in the shell of the particle to reduce the mass transfer of the encapsulated components to the outside of the capsules. In some embodiments, the oil phase is edible. Examples of such oils are linseed oil, chia oil, coconut oil, butter, soybean, corn, orange, sunflower, olive, and *perilla* oil.

In some embodiments, the emulsions are stabilized by surfactants. In some other embodiments, the emulsions are stabilized by stabilizers. The stabilizers may be non-surface active macromolecules, which may be added to increase the viscosity of the continuous phase and reduce the mobility of droplets in order to prevent them from coalescing.

In some embodiments, electrolytes may be added to the external aqueous phase to increase adsorption density of the stabilizing agent at the oil/water interface and reduce interfacial tension in emulsions.

In some embodiments, the droplets are formed by ultrasound via oscillations of the liquid-liquid interface during emulsification process. In some embodiments, the formation of droplets is believed to be as a consequence of unstable oscillations of the liquid-liquid interface. These capillary waves may occur and contribute to dispersion if the diameter of droplets to be disrupted is sufficiently larger than the wavelength of the capillary waves (e.g., twice the length of the wavelength).

In some embodiments, the droplets are formed by ultrasound via cavitation during emulsification process. In some embodiment, some parameters positively influencing cavitation in liquids improve emulsification in terms of smaller droplet size of dispersed phase right after disruption. In some embodiments, imploding cavitation bubbles cause intensive shock waves in the surrounding liquid and the formation of liquid jets of high liquid velocity. This may cause droplet disruption in the vicinity of a collapsing bubble. In some embodiments, the higher the viscosity, the higher the attractive forces between the molecules and therefore, the higher the threshold intensity of ultrasound for onset of cavitation. In some embodiments, addition of stabilizer possibly modifies and partly suppresses cavitation in the bulk of the liquid.

In some embodiments, the oil phase is an organic solvent that is immiscible in water or has very low solubility in water (e.g., less than 1 gram in 100 grams of water, or less than 5 gram in 100 grams of water, or less than 10 gram in 100 grams of water). In some other embodiments, the oil phase is includes (e.g., consists of) an organic solvent and an oil. Examples of such oils include CBD, hemp oil, fish oil, borage oil, coconut oil, cottonseed oil, soybean oil, safflower oil, sunflower oil, castor oil, corn oil, olive oil, palm oil, peanut oil, almond oil, sesame oil, rapeseed oil, peppermint oil, poppy seed oil, canola oil, palm kernel oil, hydrogenated soybean oil, hydrogenated vegetable oils, glyceryl esters of saturated fatty acids, glyceryl behenate, glyceryl distearate, glyceryl isostearate, glyceryl laurate, glyceryl monooleate, glyceryl, monolinoleate, glyceryl palmitate, glyceryl palmitostearate, glyceryl ricinoleate, glyceryl stearate, polyglyceryl 10-oleate, polyglyceryl 3-oleate, polyglyceryl 4-oleate, polyglyceryl 10-tetralinoleate, behenic acid, caprylyic/capric glycerides and any combination thereof. In some other embodiments, the oil phase may also contain Glycerol, Heptane, Isobutyl acetate, Anisole, Isopropyl acetate, Methyl acetate, Isoamyl alcohol, Methyl tert-butyl ether, Pentane, Ethyl acetate and any combination thereof.

In some embodiments, alginate-based particles may be generated by channeled emulsification. The two immiscible phases may be emulsified into a co-flowing stream of immiscible liquid in a micro-channel in which the flow rates of both liquids are controlled. The alginate droplets formed may be gelled inside or outside the channel. The mean size of the microcapsules formed may be varied over a wide range from 40 to 2000 um. Owing to the micrometer-sized capillary, liquid flows in microfluidic devices are expected to be completely laminar, and the resulting droplets or microcapsules are expected to have very narrow size distributions with coefficients of variance of less than 5%. In some embodiments, the inner oil phase of the microcapsules could be removed by extraction with propanol to prepare hollow microcapsules or aqueous-core microcapsules.

In some embodiments, capsule-shaped particles are generated by microemulsions preparation techniques. Calcium alginate nanoparticles may also be produced from microemulsions without large inputs of mechanical energy. Unlike other emulsification techniques that involve shear force, droplet formation in microemulsions is expected to spontaneous through self-assembly. Gelation of the alginate nano-droplets may be achieved by injecting a calcium-containing solution into the nano emulsion. Alginate nanoparticles 100-200 nm in diameter with a PDI of less than 0.25 are expected to be obtained.

In some embodiments, capsule-shaped particles are generated by Pickering emulsions. Alginate capsules containing oil cores may be prepared from Pickering emulsion templates. In some embodiments, pre-gelled Ca-alginate nanoparticles may be first formed and used as a solid emulsifier to deposit onto the oil droplets to stabilize the oil in water (O/W) emulsion. The solvent (which may serve as a second phase) may then be removed to shrink the oil droplets and interlock the Ca-alginate nanoparticles present at the interface to form a continuous shell. This technique is expected to produce alginate microcapsules with diameters of less than 5 micrometers to more than 100 micrometers, depending on the emulsification tool used. A variety of emulsifiers may be used instead of alginate chains. Another example of such emulsifier is polyglycerol polyricinoleate (PGPR). In some embodiments, a plurality of emulsifiers may be used. For example, the PGPR and lecithin may be used. In some embodiments, the lecithin and PGPR are used together to reduce the amount of PGPR.

2.4. Immiscible Multi-Phase Particles

Figure 6:
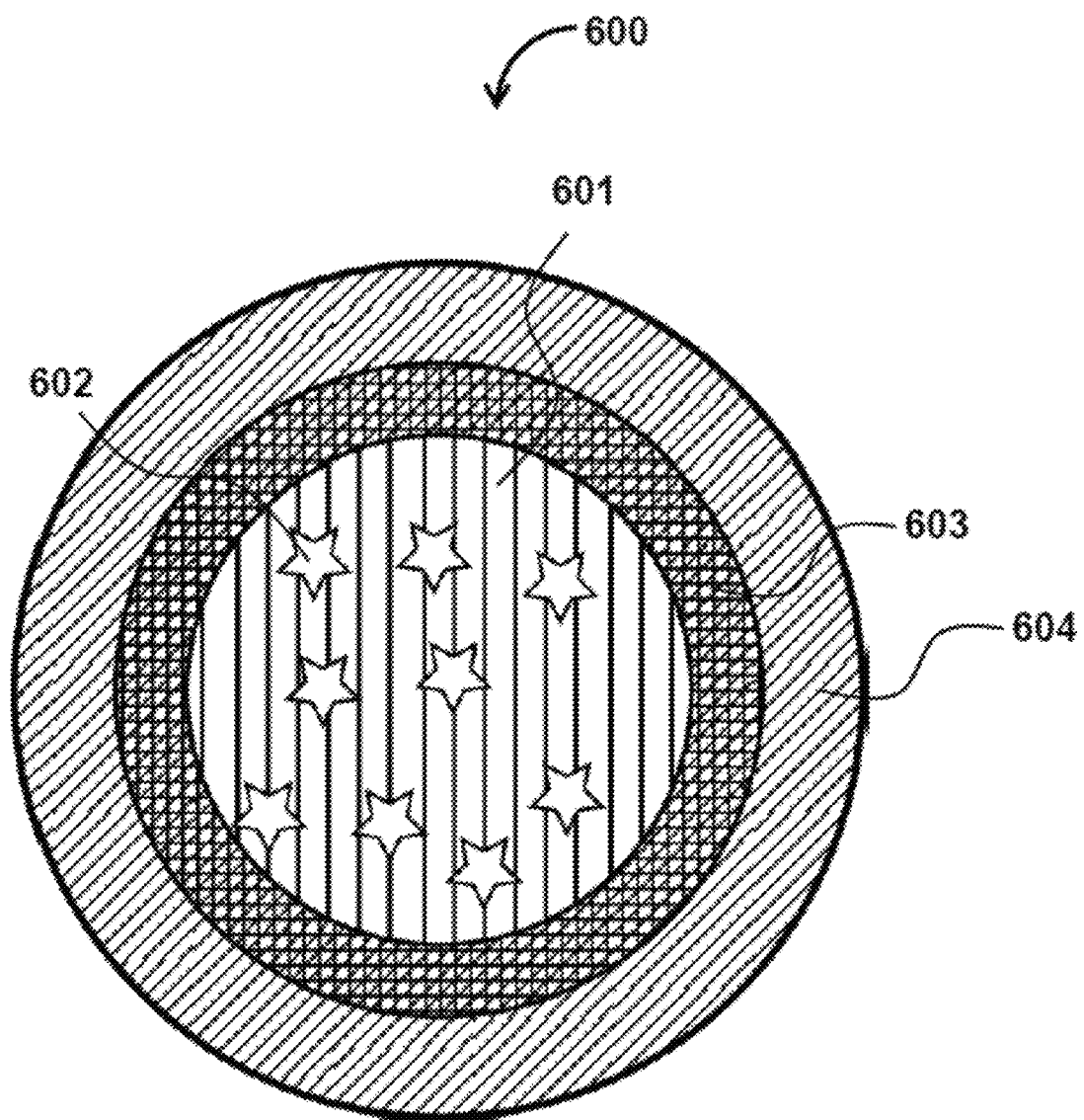
FIG. 6 is a cross section view of a particle with a core and two layers, in accordance with some embodiments of the present disclosure.

FIG. 6 illustrates an example cross-section of a particle 600 with three layers. Such particles 600 may include a core 601, which contains encapsulants 602, and an interior shell 603, and an exterior shell 604. In some embodiments, the shells 603-4 do not contain any encapsulants. In some embodiments, the shells 603-4 may also contain encapsulants.

In some embodiments, a particle 600 may be formed by O/W/O/W process. The inner oil phase may comprise a first polymer, a first encapsulant (e.g. CBD), and a first surfactant. The inner water phase may comprise a second polymer, a second surfactant, and a second encapsulant. In some embodiments, the first O/W emulsion may be carried out above the glass transition temperature of the first and the second polymers.

The outer oil phase may include a third polymer, a third surfactant, and a third encapsulant. In some embodiments, the third polymer may have a glass transition temperature lower than the first and the second polymer.

Figure 7:
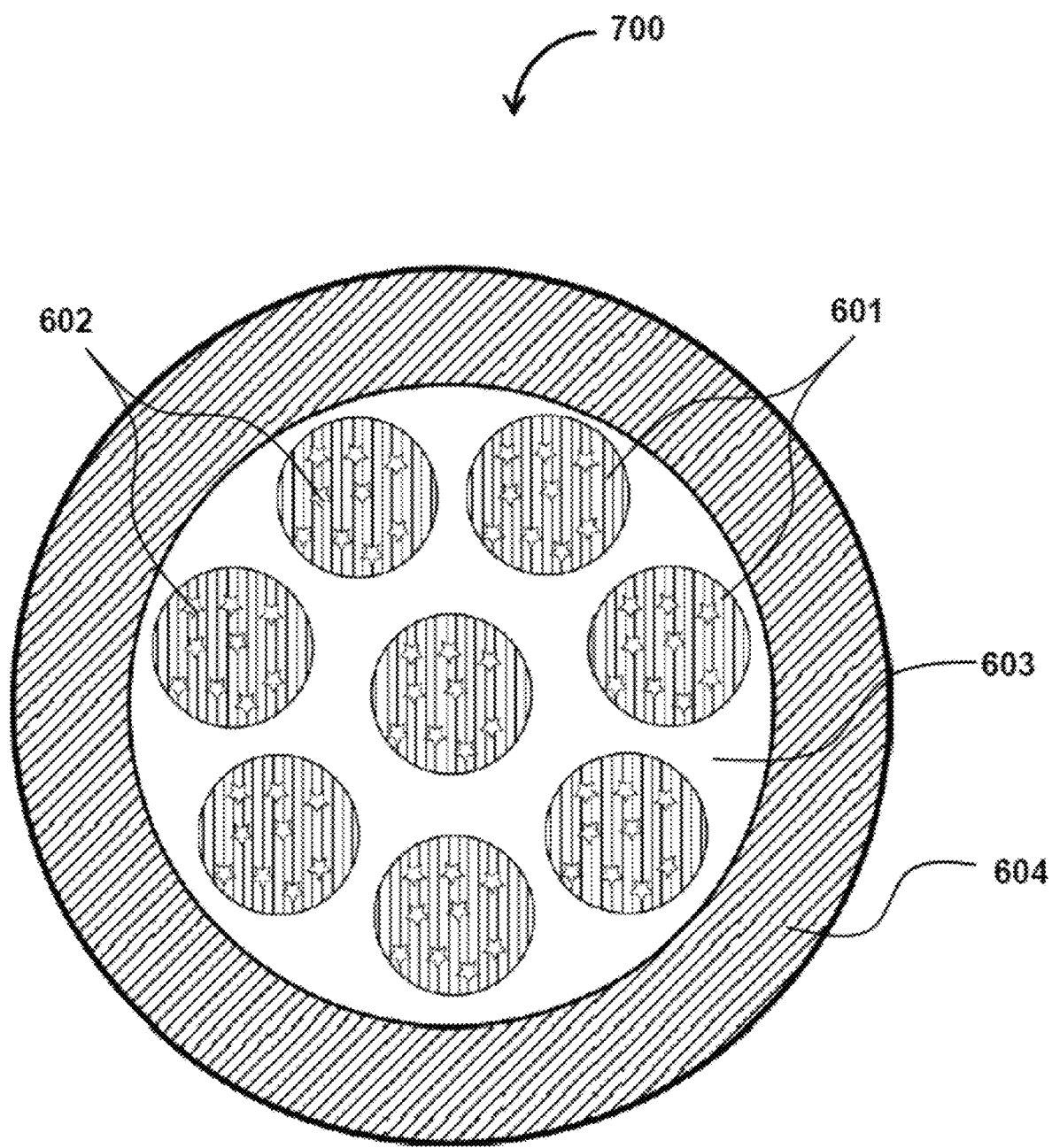
FIG. 7 is a schematic diagram that illustrates a particle with a dispersed phase, containing an encapsulant, a continuous phase, and a layer surrounding the continuous phase, in accordance with some embodiments of the present disclosure.

In some embodiments, there is only one droplet of the inner oil phase inside the inner water phase, similar to particle 600. In some embodiments, multiple droplets of inner oil phase may be inside the inner water phase, similar to particle 700 shown in FIG. 7.

In some embodiments, manufacturing particles may include multiple layers, such as 2, 3, 4, or 5 layers surrounding the core. In some embodiments, some of these layers may contain a different or similar active ingredients.

In some embodiments, some of these layers may contain no active ingredients. Such layers may be added to tune the release kinetics or provide stability for the particle in the surrounding environment (e.g. moisture, fat, pH, temperature, etc.)

In some embodiments, manufacturing particles may include obtaining other types of multiple emulsions such as water-in-oil-in-water-in-oil-in-water (W/O/W/O/W). O/W may include liquid oil droplets dispersed in a continuous liquid water phase. O/W may be formed from two immiscible or nearly immiscible water and oil phases.

Figure 8:
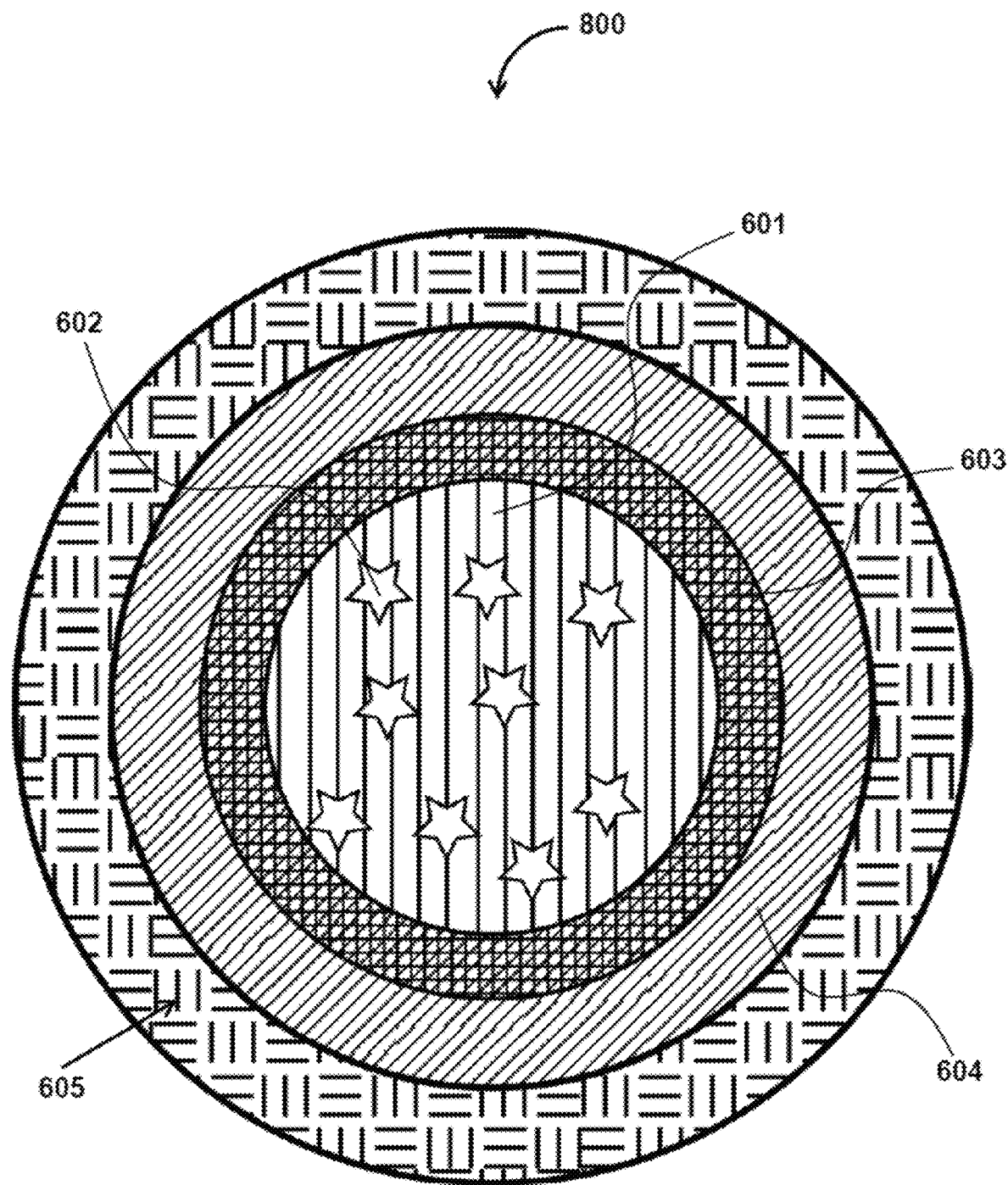
FIG. 8 is a schematic diagram that illustrates a multi-layer particle with a core and three layers surrounding the core, in accordance with some embodiments of the present disclosure.

FIG. 8 shows a particle with a core 601 and three layers surrounding the core (603, 604, and 605.) In some embodiments, all the layers of a particle shown in FIG. 8 may be prepared by emulsification (e.g. a W/O/W/O/W emulsion) in some embodiments, some of the layers of a particle shown in FIG. 8 may be prepared by emulsification and some of the layers may be prepared by other conventional techniques, e.g., using a conventional coating pan, an airless spray technique, fluidized bed coating equipment, or the like. For example, a particle with 3 layers surrounding a core, similar to FIG. 8, may be manufactured by a O/W/O emulsification followed by coating the third layer (e.g. layer 605 in FIG. 8) in a fluidized bed coater.

In some embodiments, the polymer chains in water or oil phases may be caused to crosslink or otherwise solidify by controlling the temperature. In some embodiments, a crosslinking agent may be added to crosslink the polymer chains. The crosslinking agent may be added directly to the phase containing the polymer chains or indirectly. As an example of indirect addition, to crosslink polymer chains of sodium alginate dispersed in water phase, a calcium-containing chemical, such as calcium stearoyl-2-lactylate (CSL), may be added to the oil phase and during and after the emulsification, the calcium ions may diffuse to the water phase and crosslink the alginate chains.

In some embodiments, O/W emulsions may be made by pre-processing the oil phase and water phase with a variety of techniques prior to combination. In some embodiments, the oil phase may be heated to 250° C. prior to emulsification. In some embodiments, the oil phase may be heated to 200° C. prior to emulsification. In some embodiments, the oil phase may be heated to 150° C. prior to emulsification. This may be done to dissolve surfactants, polymer chains and encapsulants. In some embodiments, the water phase may be heated to 90° C. prior to emulsification. In some embodiments, the water phase may be heated to 70° C. prior to emulsification. In some embodiments, the water phase may be heated to 60° C. prior to emulsification. In some embodiments, the heating process (e.g., to between 60 and 90° C., inclusive) may be done to dissolve surfactants, and polymer chains. In some embodiments, the heating process may be done to control the viscosity of the oil phase. Temperature ranges may be selected based on the type and amount of surfactant, encapsulants, polymer chains, and salts being added to the oil phase and to the water phase. For instance, for some of the types and amounts of surfactant described below, temperatures outside these ranges are expected to cause either incomplete solubility (or miscibility) below the low end of the temperature range, or degradation of the chemical structure of the surfactant molecule above the high end, none of which is to suggest that any subject matter is disclaimed, either here or elsewhere in this document.

In some embodiments, hydrophilic-lipophilic balance (HLB) values of the mediums (e.g., water or oil phases) may be tuned before the next emulsion. For example, to perform a W/O emulsion, polyglycerol polyricinoleate (PGPR) is added to the oil phase in some embodiments. After the W/O emulsion is made, to adjust the HLB value of the continuous phase (here oil phase) for the next emulsion (here O/W), lecithin may be added to the continuous phase to increase the HLB value suitable for an O/W emulsion.

In some embodiments, to hinder the diffusion of the encapsulant to the outer phases, inner phases may be polymerized. In some embodiments, a polymer is dissolved at a temperature above its glass transition temperature and after the emulsion, the temperature may be kept below the glass transition temperature to keep that phase solidified. For example, ethylcellulose may be dissolved in the oil phase by increasing the temperature of the oil phase above the glass transition temperature of ethylcellulose. After the emulsion, the temperature may be kept below the glass transition temperature of the ethylcellulose to keep the oil phase in gelled form, in some embodiments.

In some embodiments, a phase may be partially (e.g. 2%, 5%, 10%, 20%, 50%, or 80%) polymerized to keep the viscosity low or minimize the amount of polymer being used. For example, in a W/O emulsion, the oil phase may contain ethylcellulose and the temperature may be kept above the glass transition temperature during the emulsification. After the W/O emulsification and before the next emulsification (here O/W) the temperature may be dropped below the glass transition temperature to keep the W/O in gelled form. Then, the gelled W/O may be mixed with more oil before the next emulsion to reduce the viscosity in order to achieve a proper mixing in the next emulsification step, in accordance with some embodiments.

In some embodiments, different polymers with different glass transition temperatures, crosslinking temperatures, or crosslinking agents may be used. For example, for inner oil phases, ethylcellulose with higher glass transition may be used compared to ethylcellulose used for outer oil phases. In this manner, the inner phases may be kept solidified while the outer oil phases are in a liquid state, which in some embodiments is helpful for proper emulsification.

In some embodiments, the oil phase may be gelled. Gelling agents may be low-molecular-weight organogelators such as 12-hydroxystearic, or polymeric gelators such as ethylcellulose. Ethylcellulose may gel the oil phase, by first being dissolved in the edible oil at temperatures between 120 and 190° C., which is approximately where the glass transition temperature of ethylcellulose lies. To facilitate dissolution, a plasticizer, such as a food surfactant molecule, may be added. The type of plasticizer used in the formulation may impact the storage modulus of the gel formed. Surfactants with small hydrophilic head groups may form stronger gels, which may be due to their more prominent plasticizing effect. The cooling of the mixture is expected to promote the interaction between the ethylcellulose polymers, inducing the formation of inter-polymer hydrogen bonds. These interactions may create a three-dimensional polymer network that will behave as a trap of the liquid oil. The physical gel may be supported by hydrogen bonds formed between the unsubstituted hydroxyl groups of the ethoxylated glucose units.

In some embodiments, the gel strength is controlled by tuning the cooling rates. Different cooling rates may affect gel strength, high cooling rates being related to a weaker network structure.

In some embodiments, a lipophilic surface active agent, which may include a metal cation, may be used to cause gelation of an aqueous soluble/gellable polysaccharide, such as sodium alginate. Lipophilic surface active agents may include $C_6$-$C_{20}$ fatty acids including an appropriate metal cation, for example, calcium stearate, calcium palmitate or other calcium, copper, zinc, potassium (kappa carrageenan) or other metal cation salt of a $C_6$-$C_{20}$ fatty acid. The rate of polysaccharide gel formation (e.g., complexation with polyvalent metal cations) may be increased by acidifying the polysaccharide containing aqueous solution with vinegar, hydrochloric acid, phosphoric acid, and the like.

In some embodiments, the external aqueous solution used to form the multiple emulsions may include between about 0.1% and about 5% by weight of a hydrophilic emulsifier. A hydrophilic emulsifier may have an HLB of at least about 8 or higher.

In some embodiments, the release kinetics of the encapsulant in a product (before consumption) or in human or animal digestive tracts (after consumption) may be controlled by the number of water and oil layers encapsulating the encapsulant, the viscosity of these layers, the porosity of the layers, the type of polymers in each layer, and the level of crosslinking of polymers at each layer.

In some embodiments, the release of the encapsulant is delayed by increasing the viscosity of the oil and water phases. In some embodiments, a polymer is added to the oil or water phases to increase the viscosity. Oil layers may act as barriers for oil-immiscible encapsulants and water layers may act as barriers for water-immiscible encapsulants.

In some embodiments, the release kinetics are tuned by controlling the polymerization degree, crosslinking degree, concentration of the polymer, viscosity of the polymer, porosity of the polymerized structure, and number of water and oil layers encapsulating the encapsulants.

In such embodiments, multi-layered particles may be used for a variety of reasons, such as prolonging the diffusion of the encapsulants to the surrounding medium or having different release kinetics for a single or multiple different types of encapsulants.

In some embodiments, particles may include two or more encapsulants, wherein at least one of the encapsulants increase or complement the effect of the one of the encapsulants. Such complementary encapsulants may be released during the same duration, two separate but overlapping durations, two non-overlapping durations, or any combination thereof.

In some embodiments, particles may include two or more encapsulants, wherein at least one of the encapsulants counteracts or reduces the effect of the one of the encapsulants. In some embodiments, the encapsulant without the counteracting or reducing effect may be located in one or more inner layers or in the core. In this way, a particle may release a first encapsulant from one or more outer layers, followed by the release of a second encapsulant in the inner layers or core which counteracts or reduces the effect of the first encapsulant.

Any combination of encapsulants where the some of the encapsulants counteracts or reduces the effect of other encapsulants may be controlled and tuned by using multi-layered particles. Exemplary combinations include a sleep aid (to induce sleep) and a stimulant such as caffeine (to wake up a consumer), both being payloads in particles with staggered release times. For example, 90 wt % a first active ingredient may be released (e.g. in 0.5, 1, 2, 4, or 12 hours) before more than 10 wt % a second payload is released.

3. Solid Particles

Some embodiments may be implemented as solid particles that, when manufacturing is complete, are not (or are not yet) dispersed in a liquid medium, e.g., as a powder or small beads (mean diameter of 0.4, 0.8, 1, 2, 3, 5, 10, 100, 1000, or 2000 microns). In some embodiments, particles may be allowed to rest on an absorbent surface for a period of time to remove any surface residue therefrom.

In some embodiments, an impermeable shell is coated on the particles to seal the pores and thereafter the particles are dried to have a solid dry outer shell surrounding the encapsulants in the core. In some embodiments, the core is an oil phase. In some embodiments, the core is a solid phase. In some embodiments, the core is a combination of components mentioned above.

In some embodiments, spray drying devices may be used to dry the particles and transfer them from liquids state into solid state. In some embodiments, spray drying may include a high-pressure nozzle and a centrifugal force (e.g. an atomizer.) A gas or air may be used for the spray drying, including heated air or hot air at a temperature sufficient to dry the powder having the desired moisture content (e.g. 0.1, 0.5, 1, 2, 5, 10% water content). In some embodiments, the gas is an inert gas such as nitrogen or nitrogen-enriched air.

In some embodiments, a hydrocolloid, such as maltodextrin or gum Arabic, may be added to the external aqueous phase before the spray drying process.

In some embodiments, a fluidized bed may be used to control the moisture content of the particles. In some embodiments, a fluidized bed may be coupled with a spray drier to coat a layer (e.g., shellac) on the particles.

Figure 9:
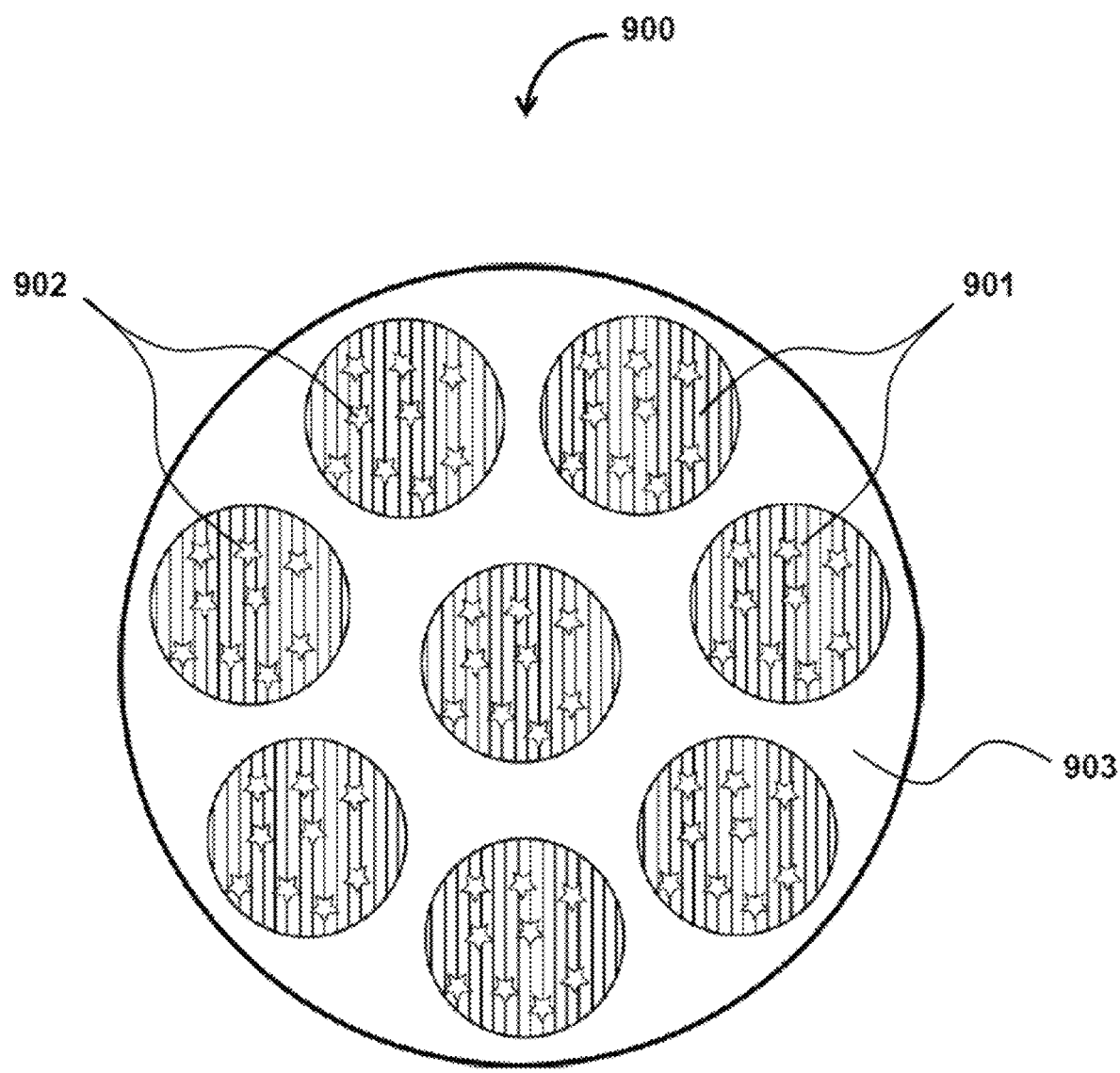
FIG. 9 is a schematic diagram that illustrates a solid particle having a dispersed phase, containing an encapsulant, and a continuous phase, in accordance with some embodiments of the present disclosure.

FIG. 9 illustrates an example cross-section of a solid particle 900 having a dispersed phase 901, containing an encapsulant 902, and a continuous phase 903. Such particle may be manufactured using various techniques, including emulsification and spray coating. For example, a bead 900 may be manufactured using a W/O emulsification, wherein the aqueous phase contains an encapsulant and the oil phase have a polymer or wax. In some embodiments, the polymer has a glass transition temperature above room temperature and the emulsification is carried out at elevated temperatures (e.g. 50, 80, or 90° C.). After the emulsification, the temperature is lowered below the glass transition temperature of the polymer to immobilize (e.g. solidify) the continuous phase. In some embodiments, the continuous phase may be immobilized by drying (e.g. fully or partially) a solvent in the continuous phase (e.g. water or organic solvent) or chemical methods (e.g. crosslinking the polymer in the continuous phase.) In some embodiments, the solid continuous phase may be grinded into small beads or a powder.

In some embodiments, an emulsion (e.g. W/O, W/O/W, or O/W/O) may be transformed to a solid phase (e.g. solid chunks or flakes). Thereafter, the solid phase may be grinded into smaller particles (e.g. powder or small beads) using various grinding techniques. Such particles may be used as final products or may undergo further processing such as spherification or layer coating.

In some embodiments, solid particles may have multiple layers. In some embodiments, some of these layers may contain a different or similar active ingredients. In some embodiments, some of these layers may contain no active ingredients. Such layers may be added to tune the release kinetics, mask flavor, or provide stability for the particle in the surrounding environment (e.g. moisture, fat, pH, temperature, etc.)

In some embodiments, a layer is a combination of different materials (e.g. combination of film-forming polymer such as ethyl cellulose, a plasticizer, and a stabilizers) to provide a set of desired properties (e.g. moisture control and controlled release) with a single layer.

In some embodiments, the particle in liquid state (e.g. wet mass) may be passed through an extruder in order to form an extrudate. Any suitable extruder may be used to extrude the wet mass. Suitable extruders include screw extruders, screen extruders, gear extruders, cylinder extruders and radial extruders.

In some embodiments, an extrudate may be unitized in order to form individual solid-state particles. While having an appropriate cross-sectional size, the extrudate may have a length greater than desired for the individual particles. Unitizing includes any process by which the extrudate is broken down into smaller units that fall within the desired size dimensions for the particles. Any unitizing method may be utilized in order to alter the extrudate into the desired shape for the particles. In some embodiment where spherical particles are desired, the extrudate may be sent to a spheronizer. Any suitable spheronizer and any suitable operating conditions for the spheronizer may be used.

In some embodiments, solid-state particles may be formed using rotary granulation techniques, powder layering techniques, spray drying techniques, spray chilling techniques, liquid extrusion/coextrusion, 3-D Printing, concentric nozzles, extrusion/spheronization, and combinations thereof.

In some embodiments, solid-state particles may be formed using spray drying techniques. In some embodiments, a mixture containing an active ingredient may be spray dried to form a core. The mixture may be atomized and sprayed into a chamber through a heated air stream. This causes the liquid component of the mixture to evaporate, resulting in dried, generally spherical shaped cores. Such cores may be used as final product or may be further processed to coat layers on them.

Figure 10:
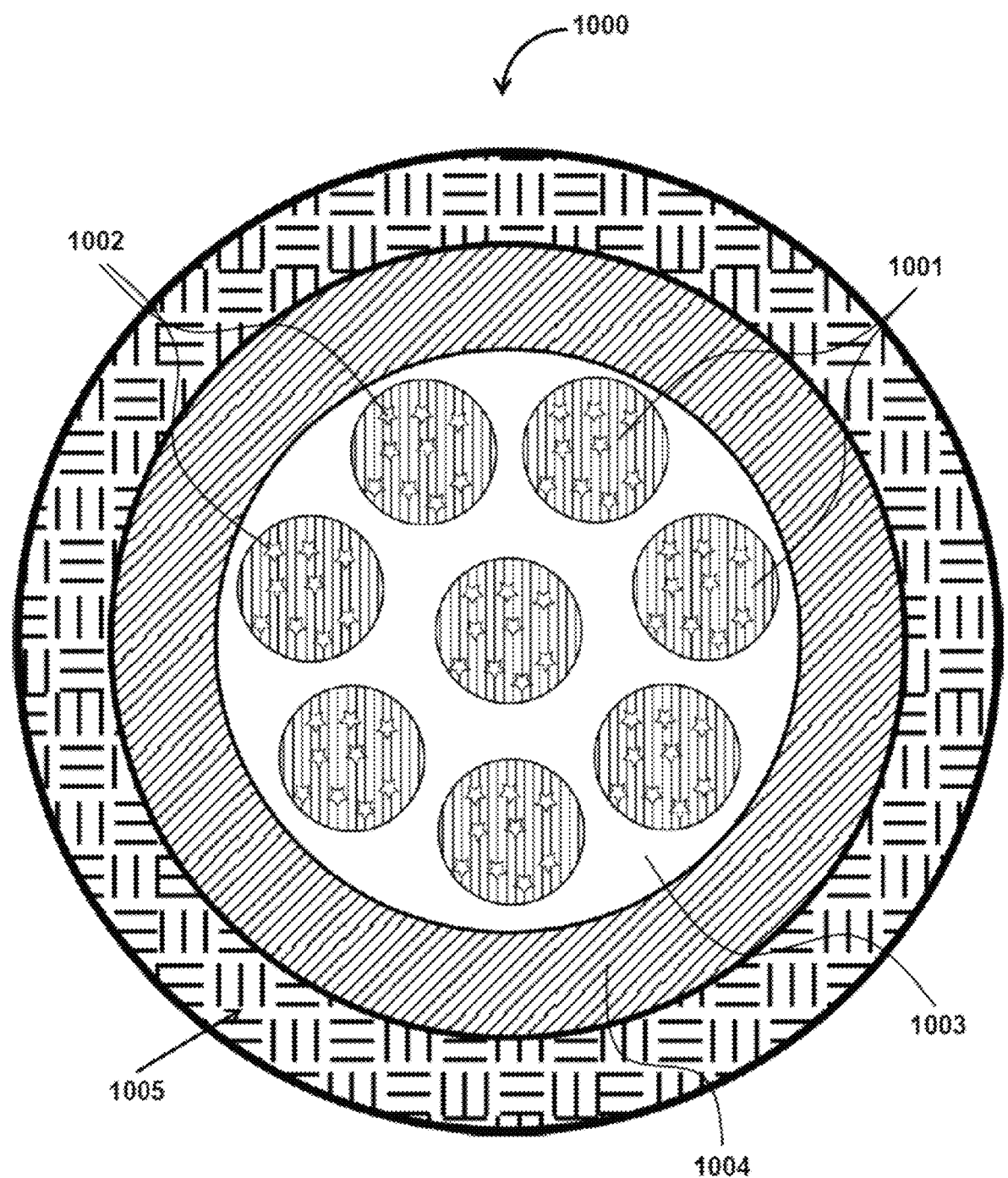
FIG. 10 is a schematic diagram that illustrates a solid particle with a dispersed phase, containing an encapsulant, a continuous phase, and two layers surrounding the continuous phase, in accordance with some embodiments of the present disclosure.

FIG. 10 illustrates an example cross-section of a solid particle 1000 with a dispersed phase 1001, containing an encapsulant 1002, a continuous phase 1003, and two layers (1004 and 1005) surrounding the continuous phase. In some embodiments, all the layers of a particle shown in FIG. 10 may be prepared by emulsification (e.g. a O/W/O/W/O emulsion) in some embodiments, some of the layers of a particle shown in FIG. 10 may be prepared by emulsification and some of the layers may be prepared by other techniques such as spray coating. For example, a particle similar to FIG. 10, may be manufactured by a W/O emulsification followed by coating the two layers layer (1004 and 1005) using conventional techniques, e.g., using a conventional coating pan, an airless spray technique, fluidized bed coating equipment, or the like.

Figure 11:
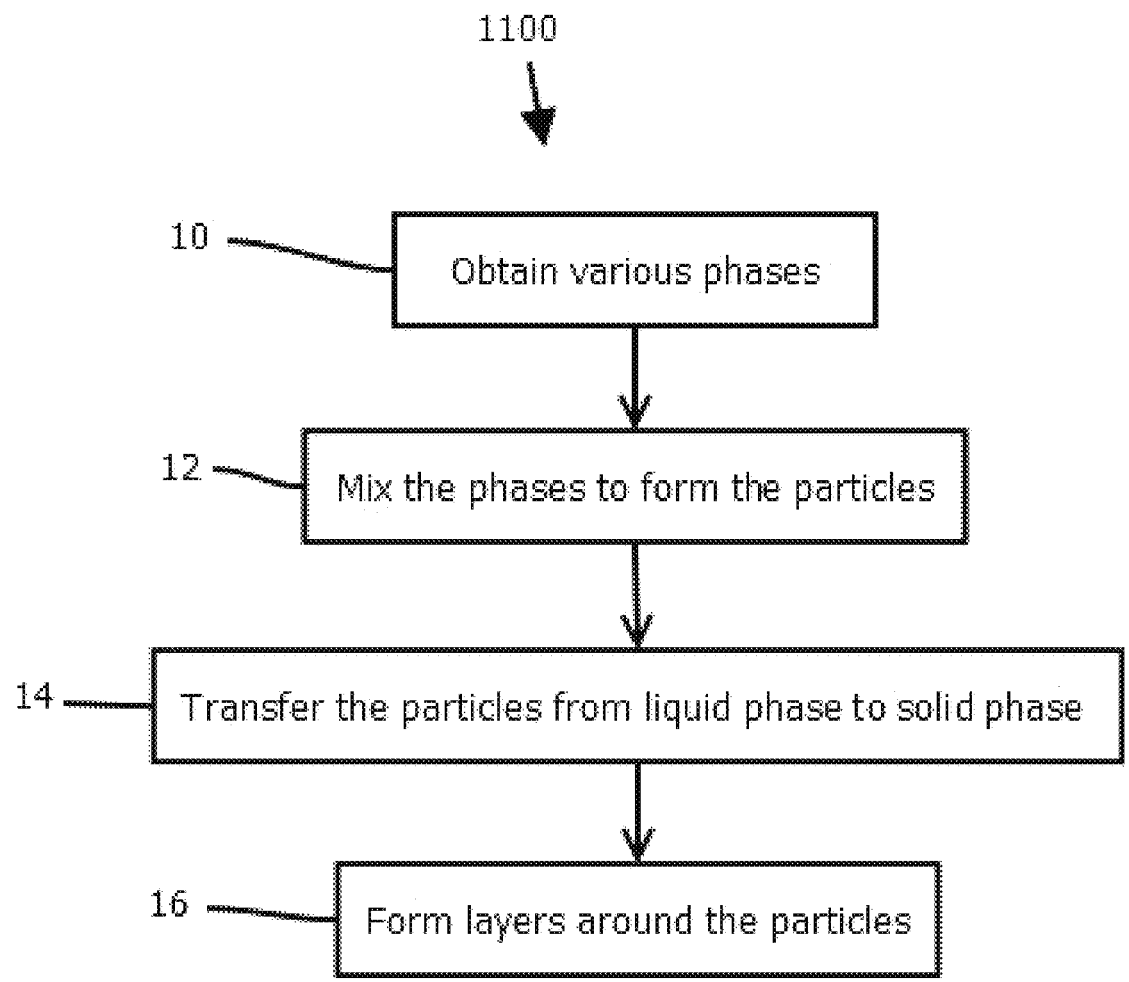
FIG. 11 is a flow diagram showing a method for preparing a particle, in accordance with some embodiments of the present disclosure.

With reference to FIG. 11, a method 1100 of preparing a particle, in accordance with some embodiment, may generally include some of the following steps: a step obtaining various phases as shown in block 10, a step of mixing the phases as shown in block 12, a step of transferring particles from liquid state to solid phase as shown in block 14, and a step of forming layers as shown in block 16.

In some embodiments, various phases, including aqueous and non-aqueous, may be obtained by combining various ingredients as shown in block 10. Each of these phases may contain encapsulants, polymers, carrier solvents, and other types of ingredients, in accordance with some embodiments.

In some embodiments, after the phases are ready, the phases are mixed together, as shown in block 12, to obtain the particles using the mixing techniques disclosed in some of the embodiments. In some embodiments, particles are formed by a phase transfer as shown in block 14. For example, a solid bead may be formed by solidifying a particle dispersed in a solution (e.g. a W/O emulsion.) The liquid state to solid phase transfer may be carried out by various techniques (e.g. spray drying), in accordance with some embodiments.

In some embodiments, multiple layers may be formed around the particles by various layering techniques (e.g. powder layering, rotary granulator, or fluidized bed coater), as shown in block 16.

4. Materials

In some embodiments (e.g., any of the expressly described embodiments, which is not to suggest that other references to "some embodiments" do not also pertain to any of the described embodiments), some or all of the ingredients, including the particles and the encapsulants, are GRAS (generally recognized as safe). GRAS status is an American Food and Drug Administration (FDA) designation that a chemical or substance added to food is considered safe by experts, and so is exempted from the usual Federal Food, Drug, and Cosmetic Act (FFDCA) food additive tolerance requirements. GRAS include any substance that is added to food, subject to approval by FDA, unless the substance is generally recognized, among qualified experts, as having been shown to be safe for its intended use, or unless the use of the substance is excluded from the definition of a food additive. Or the present techniques are also useful in non-food-related use cases, in which case non-food-grade ingredients may be used.

4.1. Particles

In some embodiments (e.g., any of the expressly described embodiments, which is not to suggest that other references to "some embodiments" do not also pertain to any of the described embodiments), a buffering oily interface may be used during a particle formation. It may be formed of any oily substance, such as oils, liquid fats, fatty acids, or any oily solution that has a density lower than that of the first or second phase such as oleic acid, eicosapentaenoic acid (EPA), and docosahexaenoic acid (DHA). It may also take the form of an oily emulsion. In some embodiments, the buffering oily layer is formed of olive oil, butterfat, coconut oil, palm kernel oil, palm oil, animal fats, castor oil, flaxseed oil, grapeseed oil, soya oil, peanut oil, fish oil, rapeseed oil, glycerol, sorbitol, sucrose, propylene glycol, polyglycerol, sunflower oil or mixtures thereof, where such mixtures have any of the foregoing oils as their base.

In some embodiments, an emulsifier may be used to facilitate the emulsification process. Examples of such emulsifiers include alginic acid, sodium alginate, potassium alginate, ammonium alginate, calcium alginate, propane-1,2-diol alginate, agar, carrageenan, locust bean gum (carob gum), guar gum, tragacanth, gum acacia, Xanthan gum, sorbitol, mannitol, glycerol, lecithin, pectin, amidated pectin, sodium and potassium phosphates, sodium and potassium polyphosphates, microcrystal line, methylcellulose, hydroxy propyl cellulose, hydroxypropyl-methylcellulose, ethylmethylcellulose, carboxymethylcellulose, Sodium, potassium, and calcium salts of fatty acids, mono- and di-glycerides of fatty acids, esters of mono- and di-glycerides of fatty acids, Sucrose esters of fatty acids, sucroglycerides, polyglycerolesters of fatty acids, propane-1,2-diol esters of fatty acids, Sodium Stearoyl-2-lactylate, calcium Stearoyl-2-lactylate, and Stearyl tartrate, propylene glycol alginate, polyethylene glycol 400, polysorbates, such as polyoxyethylene sorbitan fatty acid ester (Tween) and Span products, in particular Tween 20, 60, 80, rubbers such as gum arabic, pectins, starches and modified starches, such as Purity Gum, or proteins, such as caseinates from milk and any combination thereof among other emulsifiers. In some other embodiments, other types of emulsifiers such as alginic acid, sodium alginate, potassium alginate, calcium alginate, agar, guar gum, and xanthan gum is used.

In some embodiments, an alginate alkali metal salt may be used. The alginate alkali metal salt may be formed between alginate anions and alkali metal cations. Examples of suitable alginate alkali metal salts include Sodium alginate and potassium alginate.

In some embodiments, a particle may be made of two different types of polymers. A first type of polymer may function as a structural polymer. The particle may further contain at least one secondary polymer that exhibits greater swelling in water than the first polymer. In various embodiments, the greater swelling in water is expressed as a higher value of the Hildebrand solubility parameter. Examples of polymers that may serve as the at least one first polymer include polylactic acid, polyglycolic acid, polylactic-co-glycolic acid, polycaprolactone, polyphosphoester, polyvinyl acetate, polystyrene, polyglucosamine, gelatin, and gum arabic. Examples of swellable materials that may serve as the at least one second polymer include polyethylene oxide, polyacrylic acid, polyvinylpyrrolidone, polyvinyl alcohol, polyglucosamine, polyvinyl methyl ether-co-maleic acid, hyaluronic acid, and polysaccharides. Examples of the polysaccharides include gum arabic, alginate, carboxymethyl cellulose, hydroxypropylmethyl cellulose, hydroxyethyl cellulose, starch, and the like.

In some embodiments, when the first liquid contacts with the second liquid, the multivalent cations of the first liquid will cross-link with polysaccharides in the second liquid thereby forming coordination bonds to create a solid phase. When the first liquid is dispersed in the second liquid, the creation of the solid phase forms capsules with a solid shell encapsulating the first liquid in the core.

In some embodiments, the first liquid may further include a thickening agent. Examples of suitable thickening agents include polysaccharides, such as xanthan gum, guar gum, starch, or agar agar. A thickening agent may be 1,3-butylene glycol, acacia, acetic and fatty acid esters of glycerol, acetone, acetone peroxides, acetylated distarch adipate, acetylated distarch phosphate, acetylated monoglycerides, acid-treated starch, adipic acid, agar, alginic acid, alkaline-treated starch, aluminum ammonium sulfate, aluminum potassium sulfate, aluminum silicate, aluminum sodium sulfate, aluminum sulfate, aluminum ammonium sulfate, ammonium adipate, ammonium alginate, ammonium bicarbonate, ammonium carbonate, ammonium chloride, ammonium dihydrogen phosphate, ammonium hydrogen carbonate, ammonium phosphate, ammonium phosphatides, ammonium salts of phosphatidic acid, ammonium sulfate, anoxomer, ascorbic acid, ascorbyl palmitate, ascorbyl stearate, azodicarbonamide, beeswax, benzoic acid, benzoyl peroxide, beta-cyclodextrin, bleached starch, bone phosphate, brominated vegetable oil, butyl p-hydroxybenzoate, butylated hydroxyanisole, butylated hydroxymethylphenol, butylated hydroxytoluene, calcium acetate, calcium alginate, calcium aluminum silicate, calcium ascorbate, calcium benzoate, calcium bromate, calcium carbonates, calcium chloride, calcium citrate, calcium dihydrogen phosphate, calcium disodium ethylenediamine-tetraacetate, calcium DL-malate, calcium ferrocyanide, calcium gluconate, calcium hydrogen sulfite, calcium hydroxide, calcium iodate, calcium lactate, calcium lactobionate, calcium peroxide, calcium phosphate, calcium polyphosphates, calcium propionate, calcium pyrophosphatecalcium salts of fatty acids, calcium silicate, calcium sorbate, calcium stearate, calcium stearoyl lactylate, calcium sulfate, calcium tartrate, calciumiodiate, candelilla wax, carbamide, carbon dioxide, carnauba wax, carob bean gum, carrageenan, castor oil, cellulose gum, celluloses, chlorine, chlorine dioxide, cholic acid, choline salts and esters, citric acid, citric and fatty acid esters of glycerol, crosslinked sodium carboxymethylcellulose, cupric sulfate, D-alpha-tocopherol, dammar gum, decanoic acid, dedesoxycholic acid, dedextrins, dextrin ethyl cellulose, dehydroacetic acid, dextrose, diacetyltartaric acid esters of mono- and diglycerides of fatty acids, diammonium hydrogen phosphate, dicalcium pyrophosphate, diethyl pyrocarbonate, dilauryl thiodipropionate, dimethyl dicaronate, dimethylpolysiloxane, dioctyl sodium sulfosuccinate, dipotassium hydrogen phosphate, disodium ethylenediamine-tetraacetate, disodium hydrogen phosphate, disodium pyrophosphate, distarch phosphate, DL-alpha-tocopherol, DL-tartaric acid, dodecyl gallate, erythorbic acid, ethoxyquin, ethyl alcohol, ethyl cellulose, ethyl hydroxyethyl cellulose, ethyl p-hydroxybenzoate, ethyl protocatechuate, ethylene dichloride, esters of glycerol and thermally oxidized soy bean fatty acids, ethoxylated mono- and diglycerides, ethyl hydroxyethyl cellulose, ferric ammonium citrate, ferrous ammonium citrate, formic acid, gellan gum, gelatin, genipin, gibberellic acid, glucono delta-lactone, glycerin, glycerol, glycerol ester of wood rosin, guaiac resin, guar gum, gum acacia, gum arabic, gum ghatti, gum guaiac, heptylparaben, peroxide derivatives, hydrogen peroxide, hydroxylated lecithin, hydroxypropyl cellulose, hydroxypropyl distarch phosphate, hydroxypropylmethyl cellulose, amino methacrylate, hydroxypropyl starch, insoluble polyvinylpyrrolidone, iron gluconate, iron lactate, isoamyl gallate, isopropyl alcohol, isopropyl citrate mixture, kaolin, karaya gum, L(+)-tartaric acid, lactated monodiglycerides, lactic and fatty acid esters of glycerol, lactitol, lactylated fatty acid esters of glycerol and propylene glycol, lactylic esters of fatty acids, lauric acid, lecithin, locust bean gum, magnesium carbonate, magnesium DL-lactate, magnesium gluconate, magnesium hydrogen carbonate, magnesium hydroxide, magnesium hydroxide carbonate, magnesium L-lactate, magnesium oxide, magnesium salts of fatty acids, magnesium silicate, magnesium stearate, maltitol, mannitol, methyl alcohol, methyl ethyl cellulose, methylcellulose, methylene chloride, metatartaric acid, methylparaben, microcrystalline cellulose, milk protein, mineral oil, modified cellulose, modified starches, monoglyceride citrate, mono- and diglycerides, monostarch phosphate, myristic acid, nisin, nitrogen, nitrous oxide, nordihydroguaiaretic acid, o-phenylphenol, octanoic acid, octyl gallate, oleic acid, oxidized starch, oxystearin, palmitic acid, paraffin wax, pectin, pentapotassium triphosphate, pentasodium triphosphate, petrolatum, petroleum jelly, petroleum wax, phosphated distarch phosphate, phosphoric acid, pimaricin, poloxamer 33 1, poloxamer 407, polydimethylsiloxane, polydextroses, polyethylene glycols, polyglycerol esters of fatty acids, polyoxyethylenes, polypropylene glycol, polysorbates, polyvinylpolypyrrolidone, polyvinylpyrrolidone, potassium acetate, potassium acid tartrate, potassium adipate, potassium alginate, potassium benzoate, potassium bicarbonate, potassium carbonate, potassium chloride, potassium citrate, potassium dihydrogen citrate, potassium dihydrogen phosphate, potassium ferrocyanide, potassium gibberellate, potassium gluconate, potassium hydroxide, potassium iodate, potassium lactate, potassium metabisulfite, potassium nitrate, potassium nitrite, potassium persulfate, potassium phosphate, potassium polymetaphosphate, potassium polyphosphates, potassium L(+)-tartrate, potassium salts of fatty acids, potassium sorbate, potassium sulfate, potassium sulfite, potassium tripolyphosphate, processed eucheuma seaweed, propane-1,2-diol alginate, propionic acid, propyl gallate, propyl p-hydoxybenzoate, propylene glycol, propylene glycol alginate, propylene glycol esters of fatty acids, propylene glycol mono- and diesters, propylene oxide, propylparaben, *quillaia* extracts, rice bran wax, salts of fatty acids, shellac, silicon dioxide, sodium acetate, sodium acid, sodium acid pyrophosphate, sodium adipate, sodium alginate, sodium aluminosilicate, sodium aluminum phosphate, sodium ascorbate, sodium benzoate, sodium bicarbonate, sodium bisulfate, sodium carbonate, sodium carboxymethylcellulose, sodium caseinate, sodium chloride, sodium citrate, sodium dehydroacetate, sodium diacetate, sodium dihydrogen citrate, sodium dihydrogen phosphate, sodium dioxide, sodium DLmalate, sodium erythorbate, sodium ferrocyanide, sodium fumarate, sodium gluconate, sodium hydrogen carbonate, sodium hydrogem DL-malate, sodium hydrogen sulfite, sodium hydroxide, sodium hypophosphite, sodium L(+)-tartrate, sodium lactate, sodium lauryl sulfate, sodium metabisulfite, sodium metaphosphate, sodium nitrate, sodium nitrite, sodium phosphates, sodium polyacrylate, sodium polyphosphates, sodium potassium tartrate, sodium propionate, sodium pyrophosphate, sodium salts of fatty acids, sodium sesquicarbonate, sodium stearoyl lactylate, sodium stearyl fumarate, sodium sulfite, sodium tartrate, sodium thiosulfate, sodium tripolyphosphate, sorbic acid, sorbitan monolaurate, sorbitan monooleate, sorbitan monopalmitate, sorbitan monostearate, sorbitan tristearate, sorbitol, sorbitol sodium, sulfur dioxide, stannous chloride, starches, starch acetate, starch sodium octenylsuccinate, stearic acid, stearyl citrate, stearyl monoglyceridyl citrate, stearyl tartrate, succinic acid, succinylated monoglycerides, sucroglycerides, sucroses, sucrose acetate isobutyrate, sucrose esters of fatty acids, talc, tannic acid, tannins, tara gum, tartaric acid, tert-butylhydroquinone, tetrapotassium pyrophosphate, tetrasodium pyrophosphate, thiodipropionic acid, tocopherols, tragacanth, tragacanth gum, triacetin, triammonium citrate, tricalcium phosphate, trichloroethylene, triethyl citrate, trimagnesium phosphate, tripolyphosphate, tripotassium citrate, tripotassium phosphate, trisodium citrate, trisodium phosphate, urea, waxes, xanthan gum, xylitol, derivatives thereof, and combinations thereof. The thickening agent may be a polysaccharide. The thickening agent may be selected from xanthan gum and a galactomannan (e.g., locust bean gum, guar gum, combinations thereof, or derivatives thereof).

In some embodiments, the gelatin shells may contain a preservative, such as mixed parabens, for example, methyl or propyl parabens. The parabens are incorporated into the shell formulation in minor proportions (e.g. 0.1, 0.5, 1, 2, 5 wt %) as compared to the total weight of the shell formulation.

In some embodiments, particles may have a gelatin shell. In some embodiments, the addition of partial glycerides of fatty acids enable encapsulating ethanol without damaging the mechanical stability of the gelatin shell. The partial glycerides useful in the fill include monoglycerides or diglycerides as well as mixtures thereof. Suitable commercially available products include, for example, glycerol monocaprylate (Imwitor 308 of Dynamit Nobel), glycerol monodicaprylate (Imwitor 908), mixtures comprising glycerol monodicaprylate and glycerol monodicaprate (Imwitor 742) and partial glycerides of ricinoleic acid (Softigen 701 and Rilanit).

In some embodiments, a particle may be made from capsule forming materials comprising gelatin. Various gelatins may be used for this purpose. Some embodiments may us gelatin having a viscosity of 1 to 30 millipoises and a bloom strength up to 150 grams or gelatin having a bloom value of 160 to 250. Gelatin has the advantage as an encapsulating material in that it is heat-moldable. The gelatin capsule size and shape may vary depending on the amount of fill that will be contained therein. The capsule shell material may be used to form a wide variety of shapes and sizes such as spheres, oblong shapes, disks, squares, cylindrical, and shapes that resemble the appearance of a garnish associated with an alcoholic beverage.

In some embodiments, a lipophilic solvent or suspension carrier may be selected from a group consisting of shortchain triglycerides (SCTs), medium-chain triglycerides (MCTs), long-chain triglycerides (LCTs), medium-chain partial glycerides, polyoxyethylated fatty alcohols, polyoxyethylated fatty acids, polyoxyethylated fatty acid triglycerides or partial glyceride, ester of fatty acids with low molecular weight alcohols, a partial ester of sorbitan with fatty acids, a polyoxyethylated partial ester of sorbitan with fatty acids, a partial ester of sugars or oligomeric sugars with fatty acids, a polyethylene glycol, vegetable oil, and any combination thereof.

In some embodiments, the carrier oil may be selected from the group consisting of *cannabis* oil, borage oil, coconut oil, cottonseed oil, soybean oil, safflower oil, sunflower oil, castor oil, corn oil, olive oil, palm oil, peanut oil, almond oil, sesame oil, rapeseed oil, peppermint oil, poppy seed oil, canola oil, palm kernel oil, hydrogenated soybean oil, hydrogenated vegetable oils, glyceryl esters of fatty acids, glyceryl behenate, glyceryl distearate, glyceryl isostearate, glyceryl laurate, glyceryl monooleate, glyceryl monolinoleate, glyceryl palmitate, glyceryl palmitostearate, glyceryl ricinoleate, glyceryl stearate, polyglyceryl 10-oleate, polyglyceryl 3-oleate, polyglyceryl 4-oleate, polyglyceryl 10-tetralinoleate, behenic acid, caprylic/capric glycerides, and any combination thereof.

In some embodiments, the oil phase may have various components. In some cases, the component (e.g., more than or equal to half by weight or volume) of the oil phase is a carrier oil, which may be food-grade. In some embodiments, the carrier oil may not affect (e.g., adversely) consumer-perceivable dimensions product quality (such as appearance, taste, texture, or stability). In some embodiments the carrier oil may have ingredients that protect the emulsion from chemical degradation during storage or itself serve to protect from chemical degradation during storage. In some embodiments, the carrier oil may increase bioavailability of the emulsion after ingestion. In some embodiments, carrier oils may be beneficial in stabilizing the emulsion from Ostwald ripening, which is a major de-stabilization mechanism in many nano- and micro-emulsions. As mentioned, Ostwald ripening is a process in which very finer droplets of emulsion dissolve into continuous phase and, then, diffuse and redeposit upon larger droplets, thus increasing the average size of emulsion droplets. Ostwald ripening occurs because of the increased solubility of the dispersed phase (e.g., oil) into the aqueous phase. In some embodiments, this issue may be mitigated (or fully solved) by the introduction of hydrophobic properties into the dispersed phase. In some cases, a single carrier oil may be used, or in some cases, multiple carrier oils may be used (e.g., one corresponding to cannabidiol (CBD) oil and another to convey various vitamins).

In some embodiments, MCT-based oils are expected to afford certain advantages, as the rate and extent of lipid digestion is believed to be higher for MCT-based oils than LCT-based oils. This effect may be attributed to differences in the water dispersibility of medium and long chain fatty acids formed during lipolysis. Embodiments are not limited to systems that afford these benefits, though, which is not to suggest that any other description is limiting.

In some embodiments, LCT-based oils are expected to afford certain advantages, as the bio-accessibility of bioactive materials may be higher for LCT-based emulsions. This may be attributed to the greater solubilization capacity of mixed micelles formed from long-chain fatty acids, as these micelles are expected to easily accommodate lipophilic molecules. Bio-accessibility (or interchangeably, bio-accessibility) can be quantified by the fraction of the administered dose of the encapsulant that reaches systematic circulation. In some embodiments, where the nature of the encapsulant is unchanged, bioavailability may be determined by measuring the total amount of encapsulant excreted after a single dose. In some other embodiments, bioavailability may be assessed by determining the area under the plasma concentration-time curve. Embodiments are not limited to systems that afford these benefits, though, which is not to suggest that any other description is limiting.

In some embodiments, where the bioactive is THC (C21H30) or similar, LCT-based oils are expected to afford certain advantages. Highly lipophilic drugs are believed to have higher bio-accessibility when administered with LCTs rather than MCTs. LCTs contain relatively long-chain fatty-acids (between 12-20 carbon atoms), which may form mixed micelles with hydrophobic cores long enough to accommodate bioactives. Embodiments are not limited to systems that afford these benefits, though, which is not to suggest that any other description is limiting.

In some embodiments, LCT-based oils are expected to afford certain advantages, as MCTs contain fatty acid chains that are short (6-12 carbon atoms), resulting in mixed micelles from its digestion products that are too small to accommodate certain bioactives, such as *cannabis*. However, MCTs are expected to have about two orders of magnitude higher solubility than LCTs, as MCTs esterified with glycerol. Embodiments are not limited to systems that afford these benefits, though, which is not to suggest that any other description is limiting.

In some embodiments, medium-long-chain triglycerides (MLCTs) may be used as a resolution in choosing between carrier oils. MLCTs contain both medium- and long-chain fatty acids.

In some embodiments, where oils with high interfacial tension, viscosity, and hydrophobicity are required, MCT- and LCT-based oils may be used. These oils may be used in high-energy emulsification methods. Droplets created by MCT- and LCT-oils are considered to be less efficient for producing droplets with small particle size; however, these oils are expected to produce stable droplets as their large molar volume renders them insoluble in water.

In some embodiments, where emulsion stability is to be increased (e.g., optimized), SCT- and MCT-oils may be used.

In some embodiments, a weighting agent can include ester gum, brominated vegetable oil, sucrose acetate isobutyrate. In some embodiments, the amount of a weighting agent is selected based on the desired target density of the resulting oil phase.

In some embodiments, polyethylene oxide may be used to control the release kinetics by partially or fully melting the polyethylene oxide dispersed in a particle.

In some embodiments, a wax or a combination of different types of waxes may be used to control the release kinetics. The term wax is intended to include, but not be limited to, bees wax, rice bran wax, camauba wax, candelilla wax, carnauba wax, glycerol monostearate, glycerol oleate, spermaceti, and the like.

In some embodiments, a particle may be solidified by cross-linking the alginate polymer chains with divalent cations. Divalent cations are believed to bind to the guluronate blocks of the alginate polymer chains, forming an 'egg-box' structure. Alginate displays varying affinities toward different cations; the degree of affinity of alginate toward the following cations decreases as Pb>Cu>Cd>Ba>Sr>Ca>Co, Ni, Zn>Mn (each being an abbreviation of an element in the periodic table). However, in some embodiments, calcium ($Ca^{2+}$) is used for ionotropic gelation of alginate because of its non-toxicity compared with other cations. Among the available calcium sources, calcium chloride ($CaCl_2$) is often a suitable salt for gelation. $CaCl_2$ is readily soluble in water, and thus calcium ions in solution may cross-link with alginate droplets instantaneously to form hydrogel particles. In some embodiments, insoluble calcium salts, e.g., calcium carbonate ($CaCO_3$), is used when gradual or controlled cross-linking is desired. The cross-linking process may be initiated by reducing the pH to dissociate the insoluble calcium salt. Readily soluble calcium salts, e.g., $CaCl_2$, may cause spontaneous gelation and are therefore used to prepare alginate particles via external, inverse, or multi-step interrupted gelation mechanisms. The use of partially soluble calcium salts, e.g. calcium sulfate ($CaSO_4$), is expected to allow for slow dissociation of $Ca^{2+}$; however, controlling the gelation kinetics is expected to be difficult (which is not to suggest that this approach is disclaimed).

In some embodiments, insoluble calcium salts (e.g., $CaCO_3$) are used to prepare alginate particles through internal gelation mechanism. In some embodiments, the salt is first dispersed in the alginate solution before emulsification. Upon emulsification, the gelation process may be initiated by solubilizing the salt, thus liberating $Ca^{2+}$ for cross-linking with the local alginate polymer chains. Liberation of the salt may be initiated by reducing the pH using a gelling initiator such as the introduction of an acid or UV irradiation in the case of a photo-acid generator. Generally, the pH is reduced by adding acid, such as glacial acetic acid, to an emulsion. A more gradual gelation may be achieved by pre-adding the glucono delta-lactone to the alginate solution containing the insoluble salt, where it slowly dissociates the salt.

In some embodiments, various polyvalent metallic cations may be used to polymerize the sodium alginate chains, including iron, silver, strontium, aluminum, manganese, selenium and, in particular, a calcium, copper or zinc salt (e.g. calcium chloride, calcium lactate, calcium gluconate, calcium carbonate), copper or zinc acetate, sulfate, chloride or gluconate (e.g. zinc sulphate).

In some embodiments, when the sodium alginate is used, it is difficult or impossible to produce small droplets due to high density and viscosity of these solutions, and in some cases a thickener is added with calcium ions to prevent the solution rich in calcium ions from floating.

In some embodiments, a small, soft, solid-walled particle may be used containing within an enclosed cavity mainly ethanol. Alginate may be used as encapsulating material because it is highly water soluble, but is insoluble in ethanol and ethanol/water mixtures. In some embodiments, the ethanol contained within the cavity formed by the gelatin, alginate or like material may be pure, substantially pure, or relatively dilute ethanol, for addition to and dissolution in an aqueous solution, such as a fruit juice, soft drink (e.g. any commercially available mixer, soda, or the like), or in water. In some other embodiments, the alcohol may be mixed with water, syrup, gel, flavoring or the like.

In some embodiments, various excipients may be incorporated in, or added to, the particles to provide structure and form to the particles. These excipients may include, but are not limited to (which is not to suggest that other lists are limiting), carbohydrates including monosaccharides, disaccharides and polysaccharides. For example, monosaccharides such as, dextrose (anhydrous and monohydrate), galactose, mannitol, D-mannose, sorbitol, sorbose and the like; disaccharides such as, lactose, maltose, sucrose, trehalose, and the like; trisaccharides such as, raffinose and the like; and other carbohydrates such as, starches (hydroxyethylstarch), cyclodextrins and maltodextrins.

In some embodiments, a stabilizing agent is added to the exterior water phase to stabilize the particles. Examples of such stabilizers are small-molecule surfactants such as Tween 20, Span 80, dioctyl sodium sulfosuccinate, and lecithin, hydrocolloids such as gum arabic, and gelatin, and milk proteins such as whey protein isolate, and sodium caseinate. In some embodiments, the stabilization of the particles in the exterior water phase may be achieved by the Pickering mechanism using chemicals such as hydrophobically modified starch granules or kafirin protein nanoparticles. In some embodiments, the particles are stabilized in the exterior water phase using mixed biopolymers. For example, the particles can be stabilized using complex coacervates of gelatin with gum arabic, soluble complexes of whey protein with carboxymethylcellulose sodium (CMC), or multilayers of whey protein with pectin or chitosan with CMC. In some embodiments, the retention of the encapsulated components inside the particles are prolonged by chemical complexation of the encapsulated components within the interior water phase. For example, the chelation of zinc or magnesium ions by phosvitin or gluconate may be used in the interior water phase to prolong the retention of the encapsulated components.

In some embodiments, pH adjusting agents, such as those selected from the group consisting of disodium hydrogen phosphate, sodium acetate, sodium bicarbonate, sodium phosphate tribasic, dipotassium hydrogen phosphate, phosphoric acid, acetic acid, lactic acid, fumaric acid, adipic acid, malic acid, tartaric acid, citric acid, hydrochloric acid, sulfuric acid, salts thereof, and any combination thereof may, be used to adjust the pH to a value between 2 and 7.

5.4.2. Encapsulants

In some embodiments, encapsulants (e.g., active ingredients) are selected from those generally used to enhance physical performance, such as nootropics, functional ingredients, stimulants, electrolytes, vitamins (e.g. vitamin D3 from lanolin or lichen), proteins, and minerals. Exemplary encapsulants may include, but are not limited to, nutraceuticals, vitamins, supplements, minerals, enzymes, probiotics, bronchodilators, anabolic steroids, analeptics, analgesics, proteins, peptides, antibodies, vaccines, anesthetics, antacids, antihelmintics, anti-arrthymics, antibiotics, anticoagulants, anticolonergics, anticonvulsants, antidepressants, antidiabetics, antidiarrheals, anti-emetics, anti-epileptics, antihistamines, antihormones, antihypertensives, anti-inflammatories, antimuscarinics, antimycotics, antineoplastics, anti-obesity drugs, antiprotozoals, antipsychotics, antispasmotics, anti-thrombics, antithyroid drugs, antitussives, antivirals, anxiolytics, astringents, beta-adrenergic receptor blocking drugs, bile acids, bronchospasmolytic drugs, calcium channel blockers, cardiac glycosides, contraceptives, corticosteriods, diagnostics, digestives, probiotics, diuretics, dopaminergics, electrolytes, emetics, haemostatic drugs, hormones, hormone replacement therapy drugs, hypnotics, hypoglycemic drugs, immunosuppressants, impotence drugs, laxatives, lipid regulators, muscle relaxants, pain relievers, parasympathicolytics, parasympathicomimetics, prostagladins, psychostimulants, sedatives, sex steroids, spasmolytics, sulfonamides, sympathicolytics, sympathicomimetics, sympathomimetics, thyreomimetics, thyreostatic drugs, vasodialators, and xanthines; drugs or medicaments, breath fresheners, vitamins and other dietary supplements, minerals, caffeine, theacrine, *cannabis*, nicotine, fruit juices, and the like, and mixtures thereof. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocryptine or nicotine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, *cannabis*, THC, CBD, and combinations thereof.

In some embodiments, encapsulants may be a liquid food product selected from cannabidiol (CBD), alcohol, proteins, infusions, vinegars, or any aqueous or non-aqueous substance in liquid state or resulting from the extraction of any type of solid whose juice has a aqueous content. Additionally, medicines, especially medication for children, may be made into micro/nano capsules to make the medicine appear more palatable to a child.

In some other embodiments, other types of oil are used separately or in combination with CBD. Examples of such oils include borage oil, coconut oil, cottonseed oil, soybean oil, safflower oil, sunflower oil, castor oil, corn oil, olive oil, palm oil, peanut oil, almond oil, sesame oil, rapeseed oil, peppermint oil, poppy seed oil, canola oil, palm kernel oil, hydrogenated soybean oil, hydrogenated vegetable oils, glyceryl esters of saturated fatty acids, glyceryl behenate, glyceryl distearate, glyceryl isostearate, glyceryl laurate, glyceryl monooleate, glyceryl, monolinoleate, glyceryl palmitate, glyceryl palmitostearate, glyceryl ricinoleate, glyceryl stearate, polyglyceryl 10-oleate, polyglyceryl 3-oleate, polyglyceryl 4-oleate, polyglyceryl 10-tetralinoleate, behenic acid, caprylyic/capric glycerides and any combination thereof.

In some embodiments, one or more herbal ingredients are amongst the encapsulants. Herbal ingredients may include but are not limited to: maca, he shou wu, iporuru (*Alchornea castaneifolia*), kanna (*Sceletium Tortosum*), honokiol (*Magnolia grandiflora*), Sour Jujube Seed Semen (*Ziziphi Spinosae*), *Cnidium* Fruit (*Fructus Cnidii*), *Corydalis Rhizome* (*Corydalis yanhusuo*), *Albizia* Bark or Flower (*Cortex albiziae*), Ginseng (*Panax ginseng*), *Polygonum* (*Polygoni Multiflori*), Fu ling (*Poria cocos*), CornusFruit (*Fructus corni*), Chinese Yam (*Rhizoma dioscoreae*), *Muira puama*, *Dendrobium* sp., Licorice Root Radix (*Glycyrrhizae Preparata*), *Cordyceps* (*Cordyceps sinensis*), Chinese *Angelica* Root (*Angelicae Sinensis*), Kratom (*Mitragyna speciosa*), *Bacopa monnieri*, *Catuaba*, *Ashwaghanda*, *Peganum harmala*, Wheat Grass, Alfalfa Grass, Oat Grass, Kamut Grass, *Echinacea*, *Chlorella*, Amla Fruit, Stinging Nettles, Carob, Mesquite, Chuchuhuasai, Clavo Huasca, Chanca *Piedra*, Guayusa Powder, *Rhodiola rosea*, Shilajit, Higenamine, *Moringa* (*Moringa oleifera*), Horny Goat Weed (*Epidmedium*), *Astragalus*, Aloe Vera, Turmeric, Pine Pollen, Cucurmine (tumeric compound), Hops, Xanthohumol (hops compound), Passion Flower, *Mucuna* Puriens, Tusli, Black Pepper, Bioperine (black pepper compound), Siberian *Ginseng*, American *Ginseng*, Yerba Mate, Lemon Balm, Astragulus, Kava Kava, Schizandra, Skullcap, Valerian, California Poppy, *Epidmedium*, Pau D'Arco, Gingko, Blue Lotus, White Lilly, and Cacao. Herbal ingredients may comprise essential oils. Exemplary essential oils include but are not limited to: Linalool; B-Caryophyllene; B-Myrcene; D-Limonene; Humulene; a-Pinene; Ylang Ylang (*Cananga odorata*); Yarrow (*Achillea millefolium*); Violet (*Viola odorata*); Vetiver (*Vetiveria zizanoides*); Vanilla (*Vanilla plantifolia*); Tuberose (*Polianthes tuberosa*); Thyme (*Thymus vulgaris* L.); Tea Tree (*Melaleuca alternifolia*); Tangerine (*Citrus reticulata*); Spruce, Black (*Picea mariana*); Spruce (*Tsuga Canadensis*); Spikenard (*Nardostachys jatamansi*); Spearmint (*Mentha spicata*); Sandalwood (*Santalum spicatum*); Rosewood (*Aniba* rosaeodora); Rosemary Verbenone (*Rosmarinus officinalis*); Rosemary (*Rosmarinus officinalis*); Rose (*Rosa damascena*); Rose Geranium (*Pelargonium roseum*); Ravensara (*Ravensara aromatica*); Plai (*Zingiber cassumunar*) Pine Needle (*Pinus sylvestris* L.) Petitgrain (*Citrus aurantium*); Peppermint (*Mentha piperita*); Pepper, Black (*Piper nigrum* L.); Patchouli (*Pogostemon cablin*); Palo Santo (*Bursera graveolens*); Palmarosa (*Cymbopogon martini*); Osmanthus (*Osmanthus fragrans*); Oregano (*Origanum vulgare*); Orange, Sweet (*Citrus sinensis*); Oak Moss (*Evernia prunastri*); Nutmeg (*Myristica fragrans*) Niaouli (*Melaleuca viridifloria*); Neroli (aka Orange Blossom) (*Citrus aurantium*); Myrtle (*Myrtus communis*); Myrrh (*Commiphora myrrha*); Mimosa (*Acacia decurrens*); Melissa (*Melissa officinalis* L.); Marjoram, Sweet (*Origanum majorana*); Manuka (*Leptospermum scoparium*); Mandarin, Red (*Citrus deliciosa*); Mandarin (*Citrus deliciosa*); Lotus, White (*Nelumbo nucifera*); Lotus, Pink (*Nelumbo nucifera*); Lotus, Blue (*Nelumbo nucifera*); Lime (*Citrus aurantifolia*); Lily (*Lilum aurantum*); Lemongrass (*Cymbopogon citratus*); Lemon (*Citrus limonum*); Lavender (*Lavandula angustifolium*); Lavandin (*Lavandula hybrida* grosso); Kanuka (*Kunzea ericoides*); Juniper Berry (*Juniperus cummunis*); Jasmine (*Jasminum officinale*); Jasmine Abs (*Jasminum sambac*); Helichrysum (*Helichrysum italicum*); Grapefruit, White (*Citrus×paradisi*); Grapefruit, Pink (*Citrus paradisi*); Ginger (*Zingiber officinalis*); Geranium (*Pelargonium graveolens*); Geranium, Bourbon (*Pelargonium graveolens*, 'Herit); Gardenia (*Gardenia jasminoides*); Galbanum (*Ferula galbaniflua*); Frankincense (*Boswellia carterii*); Frangipani (*Plumeria alba*); Fir Needle White (*Abies alba*); Fir Needle Siberia (*Abies siberica*); Fir Needle Canada (*Abies balsamea*); Fennel, Sweet (*Foeniculum vulgare*); Eucalyptus Smithii. Eucalyptus Radiata, Eucalyptus Globulus, Eucalyptus Citriodora, Eucalyptus Blue Mallee (*Eucalyptus* polybractea); Elemi (*Canarium* luzonicum); Dill (*Anethum graveolens*); Cypress (*Cupressus sempervirens*); Cumin (*Cuminum cyminum*); Coriander (*Coriandum sativum*); Cocoa (*Theobroma cacao*); Clove (*Eugenia caryophylatta*); Clary Sage (*Salvia sclarea*); Cistus (aka Labdanum) (*Cistus ladaniferus* L.); Cinnamon (*Cinnamomum zeylanicum*); Chamomile, Roman (*Anthemis nobilis*); Chamomile, Blue (*Matricaria chamomilla*); Celery Seed (*Apium graveolins*); Cedarwood, Western Red (*Thuja plicata*); Cedarwood, Blood (*Juniperus virginiana*); Cedarwood Atlas (*Cedrus atlantica*); Carrot Seed (*Daucus carota*); Cardamon (*Elettaria cardamomum*); Caraway Seed (*Carum carvi*); Cajeput (*Melaleuca cajuputi*); Cade (*Juniperus oxycedrus*); Birch, White (*Betula alba*); Birch, Sweet (*Betula lenta*); Bergamot (*Citrus bergamia*); Bay Laurel (*Laurus nobilis*); Basil (*Ocimum basilicum*); Basil, Holy (*Ocimum sanctum*); Basil (*Ocimum basilicum*); Balsam Poplar (*Populus balsamifera*); Balsam Peru (*Myroxylon balsamum*); Angelica (*Angelica archangelica* L.); and combinations thereof.

In some embodiments, cannabinoids may be among the encapsulants. Cannabinoids include but are not limited to cannabigerol-type (CBG), cannabigerolic acid (CBGA), cannabigerolic acid monomethylether (CBGAM), cannabigerol monomethyl ether (CBGM), cannabichromene-type (CBC), cannabichromanon (CBCN), cannabichromenic acid (CBCA), cannabichromevarin-type (CBCV), cannabichromevarinic acid (CBCVA), cannabidiol-type (CBD), tetrahydrocannabinol-type (THC), iso-tetrahydrocannabinol-type (iso-THC), cannabinol-type (CBN), cannabinolic acid (CBNA), cannabinol methylether (CBNM), cannabinol-$C_4$ (CBN-$C_4$), cannabinol-$C_2$ (CBN-$C_2$), cannabiorcol (CBN-$C_1$), cannabinodiol (CBND), cannabielsoin-type (CBE), cannabielsoic acid A (CBEA-A), cannabielsoic acid B (CBEA-B), cannabicyclol-type (CBL), cannabicyclolic acid (CBLA), cannabicyclovarin (CBLV), cannabicitran-type (CBT), cannabitriol, cannabitriolvarin (CBTV), ethoxy-cannabitiolvarin (CBTVE), cannabivarin-type (CBV), cannabinodivarin (CBVD), tetrahydrocannabivarin-type (THCV), cannabidivarin-type (CBDV), cannabigerovarin-type (CBGV), cannabigerovarinic acid (CBGVA), cannabifuran (CBF), dehydrocannabifuran (DCBF), and cannabiripsol (CBR) cannabinoids.

Cannabinoids used in compositions of the present disclosure may be derived from various sources, including but not limited to hemp (e.g. hemp stalk, hemp stem, hemp seed), cannabis (e.g., cannabis flower, cannabisleaf, cannabis stalk, cannabis stem, cannabis seed), Echinacea purpurea, Echinacea angustifolia, Echinacea pallida, Acmella oleracea, Helichrysum umbraculigerum, Radula marginata, kava, black truffle, Syzygium aromaticum (cloves), Rosmarinus officinalis, basil, oregano, black pepper, lavender, true cinnamon, malabathrum, cananga odorata, copaifera spp., and hops.

In some embodiments, encapsulants may include tetrahydrocannabinol (THC) as a type of cannabinoids. THC may include delta-9-THC, delta-8-THC, and combinations thereof. THC may comprise delta-6a,7-tetrahydrocannabinol, delta-7-tetrahydrocannabinol, delta-8-tetrahydrocannabinol, delta-9,11-tetrahydrocannabinol, delta-9-tetrahydrocannabinol, delta-10-tetrahydrocannabinol, delta-6a,10a-tetrahydrocannabinol, and combinations thereof. Delta-9-tetrahydrocannabinol may comprise stereoisomers including (6aR,10aR)-delta-9-tetrahydrocannabinol, (6aS,10aR)-delta-9-tetrahydrocannabinol, (6aS,10aS)-delta-9-tetrahydrocannabinol, (6aR,10aS)-delta-9-tetrahydrocannabinol, and combinations thereof.

In some embodiments, one or more anti-bitterness agents are amongst the encapsulants. Examples of anti-bitterness agents include sodium benzoate, potassium sorbate, or inverted sugar. Certain anti-bitterness agents may also function as a preservative (e.g., sodium benzoate or potassium sorbate) or a sweetener (e.g., an inverted sugar).

In some embodiments, encapsulants may include Alpha-pinene, Linalool, Myrcene, Limonene, Ocimene, Terpineol, Beta-caryophyllene, Geraniol, Alpha-humulene, Phellandrene, Carene, Terpinene, Fenchol, Borneol, Bisabolol, Phytol, Camphene, Sabinene, Camphor, Isoborneol, Menthol, Nerolidol, Guaiol, Isopulegol, Geranyl, Cymene, and Eucalyptol.

In some embodiments, a pH buffer may be used to maintain or adjust its pH. Examples of pH buffers include phosphoric acid and its salts or citric acid and its salts (e.g., sodium or potassium salts).

In some embodiments, additives, such as natural or artificial flavoring agents, or natural or artificial coloring agents may be among the encapsulants. Examples of flavoring agents include flavor extracts (e.g. peach extract, orange extract, strawberry extract, oakwood extract). Examples of artificial coloring agents include FD&C, Blue No. 1, Blue No. 2, Green No. 3, Red No. 40, Red No. 3, Yellow No. 5, and Yellow No. 6. Examples of natural coloring agents include caramel E150, annatto E160b, chlorophyll E140, cochineal E120, betanin, turmeric E100, saffron E160a, paprika E160c, elderberry juice, pandan, and butterfly pea.

In some embodiments, it is preferred to use deionized (or distilled) water.

Various kinds of wines may be utilized, to be encapsulated or as the medium in which the particles are dispersed, including, but not limited to, light wines, sparkling wines, fortified wines, vermouths, and other fermented drinks. Other ethyl alcohols include, but are not limited to, distilled liquors such as whisky, rum, brandies (cognac, armagnac, applejack, kirsch, slivovitz, mirabelle, blackberry, peach), absinthe (made of brandy, wormwood, and other herbs), benedictine (made of brandy, sugar aromatic herbs), akavit, and vodka. Other ethyl alcohols include, but not limited to, compounded liquors such as gin, cordial or liqueurs. In some embodiments, fruit cordials (e.g. apricots, blackberry, cherry, raspberry, and strawberry liqueurs), and plant cordials (e.g. crème de menthe, crème de cacao, and creme de rose, curacao, kummel, maraschino, and chartreuse) may be used.

In some embodiments, a plurality of antioxidants are used. Such antioxidants may be selected from the group consisting of ethanol, polyethylene glycol 300, polyethylene glycol 400, propylene glycol, propylene carbonate, N-methyl-2-pyrrolidones, dimethylacetamide, dimethyl sulfoxide, hydroxypropyl-β cyclodextrins, sulfobutylether-β-cyclodextrin, a-cyclo dextrin, HSPC phospholipid, DSPG phospholipid, DMPC phospholipid, DMPG phospholipid, ascorbyl palmitate, butylated hydroxy anisole, butylatedhydroxy anisole, propyl gallate, a-tocopherol, y-tocopherol and any combination thereof.

In some embodiments, the first phase may further include a sweetener. Examples of suitable sweeteners include sugars, fructose, corn syrup, aspartyl peptide ester sweetener, sulfimide sweetener, ammoniated glycyrrhizin, and inverted sugars. It is believed that in addition to imparting sweetness, sweetener additions may improve spherification as the weight of that sweetener prevents a sphere from floating at the surface of the second phase thereby negatively impacting mechanical strength or sphere integrity. Certain sweeteners may also function as a thickening agent (e.g., fructose or an inverted Sugar).

In some embodiments, encapsulants may include flavors such as rose wine, mango rum, passionfruit rum, strawberry vodka, peach vodka, orange vodka, blueberry vodka, cantaloupe vodka, whiskey, coffee whiskey, hot jalapeno vodka, chocolate whiskey, PB&J vodka, chilli vodka, bacon vodka, bubble gum vodka, whipped cream vodka, marshmallow vodka, strawberry shortcake vodka, fruitloops vodka, buttered popcorn vodka, cookie dough vodka, waffle vodka, glazed donut vodka, cookies and cream whiskey, sesame and popcorn daiquiri, cinnamon churro vodka, pure milk vodka, quinoa vodka, smoked salmon vodka, sriracha vodka, pickle vodka, maple syrup vodka, rainbow sherbet vodka, root beer float vodka, cherry vodka, fireweed vodka, bison grass vodka, wasabi vodka, pineapple upside-down cake rum, asparagus gin, and saffron gin.

In some embodiments, the alcohol intended to be encapsulated may include wine, sherry, brandy, liqueurs, port, vodka, gin, whisky, scotch, cognac, tequila, rum, or champagne.

In some embodiments, encapsulants may include electrolytes, minerals, and vitamins. In some other embodiments, the encapsulated components are similar to hangover pills such as Dihydromyricetin (DHM), Prickly Pear extract, Milk Thistle, Spirulina, N-acetyl-cysteine, L-Theanine, Taurine plus vitamins, minerals.

In some embodiments, the encapsulated components consist of various ingredients. In some embodiments, a finished product may contain different type of particles with different release kinetics. For example, a beverage may contain two type of particles; particles containing alcohol and particles containing anti-hangover ingredients. The alcohol containing particles, in some embodiments, may have a faster release kinetic. Then, the particles containing anti-hangover ingredients may have slower release kinetics to help the consumer experience a better feeling after alcohol intake.

In some embodiments, a preservative may be among the encapsulants. Examples of preservatives include sodium benzoate, sodium metabisulfite, potassium sorbate, methylparabens, ethylparabens, propylparabens, butylpara bens, sorbic acid, acetic acid, propionic acid, sulfites, nitrites, sodium sorbate, calcium sorbate, benzoic acid, potassium benzonate, calcium benzonate, propylene glycol, benzaldehyde, butylated hydroxytoluene, butylated hydroxyanisole, formaldehyde donors, essential oils, monoglyceride, phenol, mercury components and any combination thereof. It is believed that the preservative may effectively inhibit growth of bacteria, molds, or yeasts and extend shelf life of this first composition without imparting any undesired changes in taste, odor, viscosity, or color thereto. Certain preservatives may also function as an anti-bitterness agent (e.g., sodium benzoate or potassium sorbate).

In some embodiments, the encapsulated ingredients may include ionic multivalent components such as ionic zinc or ionic copper. Ionic zinc may refer to any compound or composition that may release zinc ion. It may be a zinc salt or a composition comprising a non-salt zinc compound and a solubilizing agent that causes the non-salt zinc compound to release zinc ions.

Organic zinc salts may include zinc acetate, zinc propionate, zinc butyrate, zinc formate, zinc gluconate, zinc glycerate (dihydroxypropionate), zinc glycolate (hydroxyacetate), zinc lactate, zinc pyruvate, and zinc gallate. Another class of organic zinc salts may be made from di-carboxylic acids (which have two carboxy groups on a single molecule), such as maleic acid, malonic acid, and succinic acid. The corresponding zinc salts are zinc maleate, zinc malonate, and zinc succinate. Other organic salt candidates that are less soluble in aqueous solution and/or have relatively high pK values include zinc salicylate, zinc citrate, zinc oleate, zinc benzoate, zinc laurate, zinc stearate, zinc valerate, and zinc tartrate. Inorganic salts, such as zinc chloride, zinc sulfate, and other similar salts, may also be used.

In some embodiments, the encapsulated ingredients may include a cationic polymer such as polyamino acids (e.g. poly-(D, L or DL)-lysine salts, poly-(D, L or DL)-arginine salts, and all other forms of poly-cationic amino acid salts), polyamines (e.g. polymethylamine, polyethylamine, poly-n-propylamine, poly-iso-propylamine, polyethanolamine, polymethyl ethanolamine, polyethyl ethanolamine, ethyl diethanolamine, dimethyl ethanolamine, polymorpholine, poly-N-methylmorpholine, poly-N-ethylmorpholine, and mixtures thereof), poly((meth)acrylic acid) based copolymers with cationic groups (i.e. primary, secondary, tertiary or quaternary amine) on the repeating monomer unit, cationic exchange resins, proteins or peptides, and polysaccharides.

In some embodiments, the encapsulated ingredients may include a cationic surfactant such as coconut alkyl amine acetate, stearyl amine acetate, lauryl trimethyl ammonium chloride, stearyl trimethyl ammonium chloride, cetyl trimethyl ammonium chloride, di-stearyl dimethyl ammonium chloride, cetrimide, and alkylbenzyl dimethyl ammonium chloride (such as benzalkonium or benzethonium type preservative, disinfectant and fungicide).

In some embodiments, the encapsulated ingredients may include a thickener that may function to permit zinc to maintain its ionic state (e.g. glycerine, carrageenan, sugar, guar gum, and methylcellulose).

In the some embodiments, the release of the encapsulated ionic zinc may be performed for an extended period of time (e.g. 5 min, 10 min, 30 min, 60 min, 100 min, or 300 min) in the upper respiratory tract.

In some embodiments, the retention time of a droplet encapsulating ionic zinc may be prolonged by dispersing the droplets in a sticky hydrogel medium such as xanthan gum or agar gum.

In some embodiments, an absorption enhancer or bioavailability enhancer may be among the encapsulants. An absorption enhancer or bioavailability enhancer selected from the group consisting of medium chain fatty acids, omega-3 fatty acids, capric acid, caprylic acid, (8-[2-hydroxybenzoyl]-amino)caprylic acid, N-(10-[2-hydroxybenzoyl]-amino)decanoic acid, N-(8-[2-hydroxybenzoyl]-amino)caprylic acid (SNAC, salcaprozate sodium), 8-(N-2-hydroxy-5-chloro-benzoyl)-amino-caprylic acid (5-CNAC), N-(10-[2-hydroxybenzoyl]-amino)decanoic acid, alkylglycosides, chitosan, trimethylated chitosan, protease inhibitors, β-glycoprotein inhibitors, dodecyl-2-N,N-dimethylamino propionate (DDAIP), zinc chelating agents (e.g. agar, ethylenediaminetetraacetic acid (EDTA), ethylene glycol-bis(2-aminoethylether)-N,N,N,N'-tetraacetic acid (EGTA), 1,2-bis(o-aminophenoxy)ethane-N,N,N',N'-tetraacetic acid (BAPTA), and ethylenediamine-N,N-diacetic-N,N'-di-β-propionic (EDPA)), calcium chelating agents (e.g. ethylene glycol tetraacetic acid, ethylene diamine tetraacetic acid (EDTA), salicylic acid, flavonoids (e.g. quercetin ((2-(3,4-dihydroxyphenyl)-3,5,7-trihydroxy-4Hchromen-4-one), luteolin), isoflavones (e.g. genistein (5,7-dihydroxy-3-(4-hydroxyphenyl)chromen-4-one)), flavonoid glycosides (naringin), alkaloids (e.g. sinomenine (7,8-didehydro-4-hydroxy-3,7-dimethoxy-17-methylmorphinan-6-one), triterpenoid saponins (glycyrrhizin [(3,18)-30-hydroxy-11,30-dioxoolean-12-en-3-yl 2-O-glucopyranuronosyl-Dglucopyranosiduronic acid]), nitrile glycosides, phytomolecules (e.g. lysergol, allicin (garlic)), terpenes (ginkgolide A, B, C and J), ginsenosides, epigallocatechin, epigallocatechin gallate, phenanthrene, cuminumcyminum Linn, herb, ginger, aloe vera, capsaicin, colchicine, vincristine, matrine, ammonium glycyrrhizinate, beeswax, piperine, trikatu, and their pharmaceutically acceptable salts (e.g. sodium), or derivatives (e.g. esters). In some cases, encapsulants are suitable for being ingested by a human, or in some cases, the encapsulants are not suitable for human or animal ingestion, for instance, active ingredients for topical creams or lotions.

5. Size

In some embodiments, particles are characterized by their size. The particle size distribution can be determined by sieve analysis. Unless indicated otherwise, the particle size refers to the mean size.

In some embodiments, the particles are so small in diameter that the consumer (e.g., a human) does not feel the particles as distinct entities in his/her mouth. In some other embodiments, the particles are big enough in diameter that the consumer may bite down, squeezes or otherwise causes one or more such particles to break open in his/her mouth. In some other embodiments, the particles are big enough that the consumer may feel them in his/her mouth but not too big that he/she may bite them. In some embodiments, different type of particles with different encapsulated materials are mixed.

In some embodiments, the size of the particles is smaller than the mouth-feel detection limit for human consumers, e.g., in a panel of 20 consumers presented with a host material having a concentration of between 5 and 50 particles per cubic centimeter, in a blind taste test with comparing to a particle-free version of the host material, fewer than 5 consumers will report that they may tell a difference in mouthfeel between the augmented and un-augmented version.

In some embodiments, the particles are larger, and the consumer may notice a change in mouth-feel caused by the particles. In some embodiments, the mean size of the particles is less than 3 millimeters, less than 1 millimeter, less than 500 micrometers, less than 300 micrometers, or less than 100 micrometers. The sizes may have a distribution, with a high-side characteristic size value, referred to as a maximum size. The maximum size is three standard deviations larger than the mean size-ranges, and the same ranges as discussed above with respect to mean sizes may apply to the maximum size. (Thus, a large enough sample is likely to have some particles larger than the "maximum size," though they will be rare.) In some embodiments, the particles sizes within a sample are expected to exhibit a Gaussian distribution.

In some embodiments, the particles are less than 500, 100, 10, or 1 micrometers in size. In some embodiments, the particles are less than 500, 100, or 50 nanometers in size.

In some embodiments, the particles are less than 1, 0.2, 0.02, or 0.002 cubic millimeters in volume. In some embodiments, the particles are less than 1, 0.2, or 0.2 cubic micrometers in volume. Volumes referenced are mean volumes unless indicated otherwise.

In some embodiments, the particles are filtered after manufacturing to narrow the size distribution or remove the bigger particles. In some embodiments, filters may have a pore size of less than 1 millimeter, 500 micrometers, 100 micrometers, 1 micrometer, 500 nanometers, or 100 nanometers.

In some embodiments, the particles may be purified after manufacturing to remove the unreacted chemicals. In some embodiments, the particles may be purified using a variety of techniques. In some embodiments, the particles were purified by spinning down the particles by centrifuge and washing them multiple times with a solvent such as water. In some embodiments, the particles purified using other techniques such as passing through a filter or sieve.

In some embodiment, the size and structure of the particles are tuned by changing the type and concentration of the multivalent cations, the concentration and molecular weight of the alginate, as well as the ratio and distribution of its guluronic (G) and mannuronic acid (M) units. Higher G/M ratio alginates may produce stiffer gels with better mechanical integrity. The type and concentration of gelling ion ($Ca^{2+}$, $Sr^{2+}$, $Ba^{2+}$), the presence of other ions such as sodium in the gelling solution, and gelling time and temperature may also affect the size and structure of the capsules. Divalent cations with higher affinities for alginate, such as Sr and Ba, are expected to cause formation of inhomogeneous particles (dense shell, diffuse core), while the addition of non-gelling ions such as sodium to the gelling bath may increase homogeneity.

In some embodiments, hydrophobicity of the oils may be tuned by introducing a mixture of oils to produce micro- and nano-emulsions. A goal of using such mixtures is to modulate the hydrophobicity to the point where a desired size or stability is reached for the dispersed droplets. In some embodiments, micro-emulsions have droplets with a mean (or median) diameter ranging from 1-1000 μm. In some embodiments, the droplets have a mean (or median) diameter between 5-200 μm in size. In some embodiments, the droplets have a mean (or median) diameter between 10-25 μm in size. In some embodiments, nano-emulsions have droplets with a mean (or median) diameter ranging from 10-1000 nm in size. In some embodiments, the droplets have droplets with a mean (or median) diameter ranging from 10-250 nm in size. In some embodiments, the droplets have a mean (or median) diameter ranging from 15-25 nm in size.

In some embodiments, the size of the particles may be characterized by dynamic light scattering (DLS).

In some embodiments, the formed particles may undergo a purification process to minimize or otherwise reduce the bitter taste of particles encapsulating *cannabis* extract (e.g. CBD and THC).

In some embodiments, particles may be passed through a hydrophilic filter membrane with pore sizes ranging from 100-450 nm. This step is done to remove (or reduce an amount of) particulate contamination including micro-organisms, dust, metallic particles shed by the ultrasonic horn, left-over plant matter, etc. The hydrophilic filter also makes it likely that any unencapsulated, hydrophobic droplets have low affinity for the membrane material.

In some embodiments, disposable syringe filters, including a plastic housing and a disc-shaped membrane, may be used to remove the mentioned impurities. These disposable filters may be used for small-volume (10-30) sample filtration. Examples of appropriate hydrophobic materials for this purpose include nylon, polyethersulfone, cellulose acetate, regenerated cellulose, anopore, glass fiber, polypropylene, hydrophilic polyvinylidene fluoride, and hydrophilic polytetrafluroethylene.

In some embodiments, disposable vacuum filtration systems, including polystyrene filter funnels, may be used to remove the mentioned impurities. A vacuum pump may be connected to the assembly of the filter, fitting, and the attached bottle to collect the sample. The filter funnel may be made of a hydrophilic membrane, with pore sizes ranging from 100-450 nm, e.g., 220 nm. Disposable vacuum filtration systems may be utilized for purification of samples with volumes up to 500 ml or larger.

In some embodiments, reusable in-line sterilizing filters, including a hydrophilic hollow fiber material packed into a plastic cartridge, may be used to remove the mentioned impurities. These filters may have a network of long, hollow filaments with pore sizes ranging from 100-450 nm, preferably 220 nm. The in-line sterilizing filters may be used for purification of samples with volumes up to several liters at a time, or larger. The sterilizing filters may be backflushed with water to clear out the particle matters that have stuck in the membrane, e.g., like in response to determining that more than a threshold amount of emulsion has been filtered or exceeding a threshold pressure drop. Several methods, including small pumps, which are able to provide low flow rates (0.1-1 L/min), can be used to push the particles through the membrane.

In some embodiments, crossflow filtration may be used to continuously purify the particles.

6. Stability

In some embodiments, stabilizers have a hydrophobic tail with a hydrophilic head that facilitates placement of themselves in the interphase of oil and water and stabilize the particles. In some embodiments, stabilizers may provide surface elasticity or steric stability for the particles in order to prevent or impede coalescence or aggregation over a wide pH range (e.g. pH of 2-7).

In some embodiments, the stabilizer may be chosen based on the size of the particles. For example, small molecule non-ionic surfactants, such as polysorbates or sodium dodecyl sulfate (SD S), may be used to stabilize particles smaller than 200 nanometers while other surfactants such as lecithin or proteins may be used to stabilize particles bigger than 200 nanometers.

In some embodiments, suspension stability may be measured using zeta-potential analysis to determine the surface charge of the particles in a surrounding medium. In some embodiments, suspension stability is modified through various scenarios including addition of surfactants, viscosity modification of the continuous phase, change in particle density, or change in particle size. In some embodiments, the net value of the surface charge is kept above 10 mV to keep the particles dispersed. In some other embodiments, the net value of the surface charge is kept above 5 mV to keep the particles dispersed. In some other embodiments, the net value of the surface charge is kept above 15 mV to keep the particles dispersed. In some other embodiments, the net value of the surface charge is kept above 25 mV to keep the particles dispersed. In some other embodiments, the net value of the surface charge is kept above 20 mV to keep the particles dispersed.

In some embodiments, dispersed-to-continuous (e.g. oil-to-water) phase viscosity ratio is a factor for preparing stable emulsions. This ratio is defined by ε:

$$\xi = \left(\frac{\eta d}{\eta c}\right)$$

where ηd is the viscosity of the dispersed phase and ηc is the viscosity of the continuous phase. For a turbulent shear (e.g., with forms of mixing implemented in the provisional application incorporated by reference above), a c range of 0.5-5 is found to be optimal where droplet disruption is most efficient. In some embodiments, in order to reduce the ε value, low-viscosity oils (relative to that of the continuous phase) may be employed. In some embodiments, in order to reduce the ε value, the viscosity of the continuous phase may be increased by the addition of thickeners or co-surfactants (e.g., polyethylene glycol, or guar gum).

The volume fraction of dispersed phase (p) may be directly related to the minimum diameter (dmin) of droplet. The increase in disperse phase (oil) volume fraction results in the increase in droplet size (at constant process variables). Possible reasons could be the increase in emulsion viscosity, depletion of emulsifier and coalescence due to the increased rate of collision frequency.

In some embodiments, a surfactant or a binary surfactant system may be used to facilitate the formation of stable oil droplets within the continuous aqueous phase. In emulsion systems, the reservoir of excess free energy in the interfacial region generally is expected to result in an overall free energy that is well above the global minimum of the system. Such a colloidal system often cannot be formed by spontaneous dispersion; it is typically thermodynamically unstable, and any apparent stability may be regarded as a purely kinetic phenomenon. The emulsifier may serve to reduce the interfacial tension between the two phases and reduce the amount of input required to overcome the surface energy. Emulsifiers additionally may stabilize the final dispersion by preventing flocculation, coalescence, rupture, and separation into two immiscible phases. Therefore, the selection of appropriate surfactants is helpful for emulsion formation and stability.

In colloidal food systems, which often include particles and droplets of various kinds, particles may remain as individual units, but in many instances, aggregation takes place to form three-dimensional structures, referred as "gels." The occurrence of aggregation phenomenon is determined by the general concept of the balance between attractive forces (e.g. van der Waals) and repulsive forces. The latter may be electrostatic from charged interfaces, steric from adsorbed polymers or from vesicles in the continuous phase, or a combination of forces depending on the composition of the food emulsion. In some O/W emulsions described herein, the adsorbed surfactants are the cause of repulsive forces, prolonging the stability of particles. Ionic surfactants act mainly through electrostatic repulsion, while surfactants with a polymeric polar group provide steric repulsion as well as electrostatic effects if the polar group is also charged.

Many surfactants used in food-grade emulsion are not water soluble. The first class of such surfactants is those that are below the Krafft point (Krafft point: temperature at which the solubility of a surfactant is equal to its critical micelle concentration) at room temperature. These surfactants not only form an adsorbed monolayer at the O/W interface but form additional phases to the two aqueous and oil liquids. The second class is the surfactants that have Krafft points well in excess of room temperature and exhibit temperature-dependent phase behavior. Even surfactants with Krafft points below room temperature are classified as water insoluble as a contrast to ionic surfactants, which form transparent solutions at concentration levels of 30-40 wt %. On the other hand, for water-soluble surfactants, the adsorption of the surfactant to the interface increases with the concentration in aqueous solution until critical micelle concentration (CMC) is reached, at which the surfactant has formed a monolayer at the interface. Excess surfactants in the system may form micelles.

The emulsifying capability of a surfactant can be classified according to the hydrophilic-lipophilic balance (HLB) of its molecules. HLB is defined as the ratio of the weight percentage of hydrophilic groups to the weight percentage of lipophilic groups in the molecule. The HLB scale has been created to classify non-ionic surfactants according to their emulsifying properties. HLB values for commercially available surfactants range from 1 to 20. Surfactants with low HLB, ranging from 3 to 6, promote the formation of W/O emulsions. Commonly used classes of such emulsifiers are glycerol esters, propylene glycol fatty acid esters, polyglycerol esters, and sorbitol fatty acid esters. Surfactants with HLB values ranging from 8 to 16 favor the formation of O/W emulsions. This class of emulsifiers includes proteins, phospholipids, potassium and sodium salts, hydrocolloids, alginates, polyoxyethylene fatty acid esters, guar gum, etc.

Emulsifiers may be further categorized into low molecular mass surfactants (fatty alcohols, glycolipids, and fatty acids), and high molecular mass surfactants extracted from naturally occurring materials, polysaccharides and proteins. Low molecular weight (LMW) surfactants are mobile at the interface and efficient in reducing the interfacial tension. Consequently, they coat the oil-water interface rapidly during emulsification. Emulsifier concentration in the solution may play a decisive role to estimate the saturation radius of droplets resulting from emulsification, provided that, all other parameters are kept constant. Besides concentration, physicochemical characteristics of emulsifiers are also helpful for the formation and stability of nanoemulsions. Low molecular weight nonionic emulsifiers (Tweens, Spans) facilitate preparing the droplets of very small size. However, it is challenging to fabricate fine droplets from food biopolymers (proteins, modified starches, gums) due to their high molecular weight. Although protein-based emulsifiers have an ability to produce smaller emulsion droplets when used at lower concentrations than that of polysaccharides, high local intensities of ultrasonic treatment may denature the protein as they are sensitive to higher temperatures.

In lecithin-based nano-emulsions, Ostwald ripening may be of minor importance, especially in combination with highly non-polar oils. Physical stability may be obtained by employment of lecithin as an emulsifier, which is remarkably insoluble in water, and the choice of an oil with a distinctly low water solubility. Therefore, diffusion of the emulsified oil droplets through the aqueous medium is limited. However, it should be noted that an excess of lecithin decreases emulsion stability and results in the presence of vesicular lecithin aggregates. Thus, low amounts of surfactant are therefore considered not only desirable from a biological and cost efficiency viewpoint, but also for technological reasons. On the other hand, an increase in lecithin concentration leads to the production of smaller particles due to an increased surfactant to oil volume ratio, which in turn leads to enhanced physical stability. In contrast, large oil volume fractions lead to increased droplet collisions and hence coalescence during emulsification. None of which is to suggest that embodiments are limited to systems employing these techniques or any other described herein, as discussion of various design and engineering tradeoffs should not be read as implying any sort of disclaimer.

In some embodiments, using a single surfactant may lead to emulsions with enhanced stability, possibly due to tighter molecular packing at the oil/water interface.

In some embodiments, using a binary surfactant system may lead to emulsions with enhanced stability, possibly due to tighter molecular packing at the oil/water interface. Use of binary surfactant system allows for tuning of the HLB value. In some embodiments, the effective HLB value of the surfactants may be matched (or otherwise selected with a value that corresponds) with the HLB value of the carrier oil suitable to form O/W emulsions.

In some embodiments, the amount of surfactant(s) present in the system may range between 1 to 25% by volume. In some embodiments, the amount of surfactant(s) present in the system may range between 6 to 20% by volume. In some embodiments, the amount of surfactant(s) present in the system may range between 8 to 14% by volume. Insufficient surfactants may lead to a higher energy input requirement to create O/W emulsions of a certain size. Insufficient surfactants may lead to incomplete coverage of O/W emulsion, which may subsequently lead to droplet coalescence and phase separation. Excess surfactants may lead to formation of additional micelles. Excess surfactants may lead to an undesired increase viscosity, affecting the energy required to form droplets.

In some embodiments, the stability of the resulting composition (e.g., the emulsion, the result of adding an emulsion concentrate to a more dilute host food or beverage product, or one of these packaged for distribution, like in a glass bottle, an aluminum can with a liner, a paper-based container with a liner, or a plastic bottle) may be measured by various techniques such as particle size measurement, light scattering, focused beam reflectance measurement, centrifugation, rheology and any combination thereof. Unless another measurement method is specified, drop size measurement is used. Under this method, stability is indicated by monitoring the change in size of the particles over time.

In some embodiments, the resulting composition is stable at room temperature for about 1 day to about 36 months. In some embodiments, the composition is stable at room temperature for about 1 months to 12 months. In some embodiments, the composition is stable at room temperature for 3 to 6 months.

In some embodiments, presence of certain ingredients, such as flavoring agents or can liners, may change the stability of the solution by interacting with certain active ingredients. For examples, full spectrum CBD may interact with aluminum can liners and physically adsorb to the walls of the can and therefore reduce the available CBD in the solution. Some embodiments are expected to mitigate or eliminate this effect and impart greater stability that is exhibited by traditional approaches by reducing these interactions with the exterior walls of resulting capsules.

In some embodiments, the composition is stable at fridge temperature (e.g., less than 5° C.) for about 6 months to about 60 months. In some embodiments, the composition is stable at fridge temperature for about 1 month to 12 months. In some embodiments, the composition is stable at fridge temperature for about 1 to 14 days.

In some embodiments, the composition is stable at about 40° C. for about 2 months to about 12 months. In some embodiments, the composition is stable at about 40° C. for about 3 months to about 9 months. In some embodiments, the composition is stable at about 40° C. for about at least one month. In some embodiments, the composition is stable at about 40° C. for about at least one week. In some embodiments, the composition is stable at about 40° C. for about at least one day.

In some embodiments, the composition's pH may range between 2 and 7.5. In some embodiments, the composition's pH may range between 2 and 4. In some embodiments, the composition's pH may range between 4 and 7.

In some embodiments, a stabilizing agent may be present in the continuous aqueous phase. Once the droplets in an O/W *cannabis* beverage emulsion have been formed during homogenization, it is helpful to keep them stable throughout the expected lifetime of the product. Emulsions may become unstable through numerous physicochemical processes, which are often highly dependent on the nature of the emulsifier used to stabilize the system. These physicochemical processes include the separation of oil and water phases, coalescence, flocculation of oil droplets, and creaming of the droplets. In some embodiments, the emulsion comprises a stabilizer. In some embodiments, the stabilizer is alginate.

In some embodiments, salts or sugars are added to the interior water phases to control the osmotic pressure gradients. In some embodiments, the concentration of the salt or sugar in the interior water phase is 0.5 molar, 0.1 molar, 0.05 molar, or 0.01 molar. In some embodiments, the half-life of storage of the particles may be prolonged by balancing the osmotic pressure between the interior and exterior water phases.

Failure to maintain an appropriate osmotic balance between inner and outer aqueous phases is a source of instability for W/O/W emulsions during storage (which is not to suggest that imbalanced systems or any other subject matter are disclaimed). The osmotic pressure difference may be zero or non-zero while still achieving good stability and high yield, but it should be low enough (in absolute value) to prevent or impeded the coalescence or rupture of any swollen internal droplets. A contemplated strategy is to attempt to reduce or eliminate the swelling (or shrinkage) of internal liquid droplets by converting them into soft solid-like particles through the gelation of biopolymer ingredients such as starch or globular proteins.

7. Theory

In some embodiments, the terminal settling velocity (vs) of a particle is calculated using Stokes' law:

$$vs = \frac{g(\rho_p - \rho_w)d_p^2}{18\mu}, \quad (1)$$

wherein g is the gravitational acceleration constant (=9.81 m/s2), $\rho_p$ is the particle's density (calculated based on the net density of a capsule based on its shell density and the density of the interior phase), $\rho_w$ is the medium's density, $d_p$ is the particle's diameter (capsule outer diameter), and μ is the medium's viscosity. For example, a 500 μm capsule with a net density of 1600 kg/m3 would have a terminal settling velocity of 0.08175 m/s in water ($\rho_w$=1000 kg/m3, μ=0.001 N·s/m2). Next, the Reynold's number is calculated based on the vs obtained in the previous step. The aim here is to confirm whether the terminal velocity obtained adheres to Stokes' Law or a correction factor must be applied. Reynolds' number is given by:

$$N_R = \frac{\emptyset v_s d_p \rho_w}{\mu}, \quad (2)$$

where Ø is the shape factor of the particle (a perfect sphere would have a shape factor of unity). Following the example above, the calculated Reynold's number for a perfectly spherical particle would be 40.875. The calculated Reynold's number is significantly greater than the upper limit for the Stokes' law calculation (1 is the upper limit); meaning a correction factor (CD, drag coefficient) must be calculated and applied. The drag coefficient may be calculated by:

$$C_D = \frac{24}{N_R} + \frac{3}{\sqrt{N_R}} + 0.34 \quad (3)$$

Following the example above, CD would be ~1.40. Now, the corrected terminal velocity is calculated by:

$$v_s^2 = \frac{4}{3}g\frac{(\rho_p - \rho_w)d_p}{C_D \rho_w} \quad (4)$$

Following the example above, the new vs is 0.053 m/s. Once again, the Reynold's number calculation must be repeated and CD applied to the above equation until the variation in vs reaches below 5%.

To describe colloidal assembly and dissociation, the steric repulsion will be described in conjunction with the DLVO potential (VDLVO) which is a sum of the van der Waals (vdW) potential:

$$V_{vdW} = \frac{-A}{6}\left[\frac{2a^2}{H(4a+H)} + \frac{2a^2}{(2a+H)^2} + \ln\left(\frac{H(4a+H)}{(2a+H)^2}\right)\right] \quad (5)$$

where A is the Hamaker constant, H is the surface to surface separation distance, and a is the particle radius and the electrostatic potential Vel which is given by:

$$V_{el} = \frac{64\pi a k_b T \Gamma_0^2 n_\infty}{\kappa^2}\exp[-\kappa H], \quad (6)$$

where $n_\infty$ is the bulk ion concentration, and $\kappa^{-1}$ is the Debye length given by:

$$\kappa = e\sqrt{\frac{z_{ion} n_{ion}}{\varepsilon_r \varepsilon_0 k_b T}}, \quad (7)$$

where $z_{ion}$ is the valence and mon is the number density of ions available in the solution, and $\varepsilon_r$ is 78.4 for water. The parameter $$\Gamma_0 = \frac{\exp\left[\frac{ze\psi_0}{2k_b T}\right] - 1}{\exp\left[\frac{ze\psi_0}{2k_b T}\right] + 1} \quad (8)$$

is a function of the valence z and the surface potential wo.

In some embodiments, the particles are considered to be stable against sedimentation or foaming when the terminal velocity of the particles is on the order of $10^{-8}$-$10^{-7}$ m/s.

8. Mixing Techniques

In some embodiments, a high-shear rotor-stator device may be utilized to create coarse emulsions. A variety of stirrers, blenders and homogenizers may be used for the purpose of creating emulsions.

In some embodiments, a high-energy acoustic ultrasonication device may be utilized to create emulsions. Ultrasound-assisted emulsification is expected to be suitable for creating nano-emulsions. Ultrasonic emulsification involves the exposure of immiscible phases to high intensity (e.g., high frequency or high amplitude suitable to cause cavitation) acoustic waves, which is followed by the disruption of droplets (dispersed phase) under the influence of cavitation effects in the liquid medium (continuous phase).

Acoustic emulsification is believed to be a two-step phenomenon. In the first step, dispersed phase droplets (or bubbles) are incorporated into the continuous phase under the influence of Rayleigh-Taylor instability. Rayleigh-Taylor instability is the acceleration of one fluid into other due to acoustic waves at the media surface. In the second step, larger droplets/bubbles are broken down into smaller ones due to cavitation process. The energy required by the continuous phase in the form of shear to break or deform droplets of the dispersed phase may be expressed in terms of the Laplace pressure (p):

$$p = \gamma\left[\frac{1}{R_1} + \frac{1}{R_2}\right] + \frac{\gamma}{2R}$$

In the above equation, R1 and R2 are the radius of curvature of perfectly spherical droplets (thus, R1=R2), while γ is the interfacial tension of the droplets. When the applied shear stress is greater than the characteristic Laplace pressure, emulsions are created. Though, extremely high shear is often helpful in the case of nano-emulsions.

In dilute emulsions, where droplet coalescence is unlikely, droplet formation may be expressed in terms of the Weber number (We), which is the ratio of the external disruptive energy (Ev) over surface energy (Es):

$$We = \frac{E_v}{E_s} = \frac{\rho_c (\overline{u})^2 d_{max}}{\gamma}$$

The equation above shows the Weber number for maximum stable droplet diameter (dmax). Here, ρc is the continuous phase density, while $\overline{u}$ is the mean velocity difference across the droplet and γ is the interfacial tension of the droplets. volumetric acoustic energy density (Ev) expressed in W/cm3 or W/mL, is the energy (power) dissipated per unit volume of sample for a given period of time:

$$E_v = \frac{\text{energy input}}{\text{dispersing volume}}$$

When the dispersed phase is added into the continuous phase, there is a high energy barrier to break planar interfaces and initiate the emulsification process. Disruption of droplets increases with increasing Weber number and it is expected that droplet break-up occurs when the Weber number is higher than a critical value. $(\overline{u})^2$ is a function of average power dissipated per mass unit. Therefore, high-energy disruption forces are helpful to produce droplets of nanometer scale.

The resultant nano-emulsions are expected to show better stability against droplet aggregation than other emulsions, as their small droplet size influences the Brownian motion and colloidal interactions (though embodiments are also consistent with other approaches that have lower stability where other tradeoffs are made). The minimum size of a droplet during emulsification (dmin) may be calculated depending on the type (Fsat) and concentration of emulsifiers (Cs) used:

$$d_{min} = \frac{6\Gamma_{sat}\varphi}{C_s}$$

Here, φ is the volume fraction of dispersed phase while Fsat (usually expressed in mg/m2) is the surfactant load at saturation and defined as mass of emulsifier adsorbed per unit surface area of an interface when surfactant concentration is in excess. Above equation, along with the turbulence phenomena, shows that droplets of small size may be formed by increasing the concentration of emulsifiers, decreasing the volume fraction of dispersed phase, or using emulsifiers with a lower surfactant load at saturation.

Additionally, immersion of the ultrasonic probe may be deep enough to start cavitation. Otherwise, agitation will be the predominant phenomena, resulting in the production of potentially undesirable aerosols besides poor emulsification (again though, some embodiments may implement agitation without cavitation). Another issue is the erosion of probe tip, which can result in the contamination of emulsions with metal particles. These particles may trigger oxidation and induce the development of off flavors in the prepared emulsions. Additionally, output energy of the probe with an eroded tip is decreased, thereby reducing the system efficiency.

In some embodiments, the total volume of the emulsions in a batch may range between 0.5 to 250 ml. In some embodiments, the total volume of a emulsion in a batch may range between 1 to 20 ml.

In some embodiments, the ultrasound sonication time ranges from 1 to 75 minutes. The optimal processing conditions vary for different formulations, since over-processing might lead to fluctuating droplet sizes. Over-processing is either caused by increased droplet collision and re-coalescence rates upon increase of homogenization cycles or insufficient emulsifier concentration in relation to the increasing interfacial area. These two phenomena are often connected. If the newly created interfacial area is too large to be efficiently covered by emulsifying agents, the coalescence process is triggered. This coalescence is often the limiting factor for droplet size reduction. A plateau in particle size reduction with time is reached, where no further decrease of droplet diameters can be reached, or droplet size even slightly increases. An aspect in this context is the influence of the temperature during production. Thermal energy is produced during high-pressure homogenization. Efficient cooling may limit cavitation phenomena and prevent droplet re-coalescence. Moreover, the viscosity of the formulation can play a role. Increased inlet fluid viscosity could promote droplet rupturing through higher extensional stress and could weaken re-coalescence phenomena.

In some embodiments, the ultrasound sonication time may range between 5 to 25 minutes.

In some embodiments, the ultrasound sonication time may range between 1 to 5 minutes.

In some embodiments, the ultrasound sonication time may range between 30 seconds to 1 minute.

In some embodiments, a flow-through sonication system may be used to prepare the nano-emulsions in a continuous manner. In such embodiments, coarse micro-emulsions may be prepared in agitation tanks and fed to the sonication chamber via a pump. The micro-emulsions are subjected to high intensity ultrasonication and pumped back to the agitation tank.

In some embodiments, different droplet formation techniques (e.g. mixing two immiscible phases), such as micro-fluidization and ultrasonication may be applied in micro/nano encapsulation of different core (e.g., encapsulated, not in the sense that they are "core" to the inventions) materials. In some embodiments, these techniques may be applied as a subsequent stage to the above operations, to break up larger droplets formed with the techniques above. Some embodiments introduce energy into the system (e.g., a mixture of larger droplets of the first phase in a reservoir of the second phase) by subjecting the phases to vigorous mechanical agitation. The type of agitation which is expected to be most effective in this context is that which subjects the large droplets of the first phase to shear. Some embodiments may include an actuator configured to apply such shear, e.g., by oscillating a plate immersed in the mixture, by flowing the mixture through a tortuous path at high flow rates (e.g., with a Reynolds number of greater than 2100), by rotating a blade through the mixture, or the like. In this way, these droplets are deformed from their stable spherical shapes and break up into smaller units. In the presence of emulsifying agents, it is expected that a stable emulsion of droplets will be formed.

One condition that is expected to influence emulsion formation is temperature. Interfacial tension and viscosity are temperature-dependent, both decreasing with increase in temperature. Thus, raising the temperature of the liquids is expected to facilitate emulsion formation, subject to constraints from the heat sensitivity of the components.

In some embodiments, when viscosity of the first and second phases are low (e.g., less than 3000 centipoises), turbine and propeller mixers may be used to premix the phases prior to emulsification. In some embodiments, a stable emulsion may result from such mixing with no further treatment. In the case of higher viscosity liquids (e.g. more than 2000 centipoises) and pastes, pan mixers, kneaders and some types of continuous mixers may be used to disperse the first phase throughout the second phase. Tumbling mixers, such as those used for mixing powders may also be used for this purpose.

In some embodiments, droplets are formed (e.g., initially, or by segmenting larger droplets) with a pressure homogenizer. In some embodiments, premixed phases (e.g., the above first phase and second phase) are pumped through a narrow opening at high velocity (e.g. with a Reynolds number of greater than 2100). The opening is provided between a valve and its seat. In some other embodiments, a pressure homogenizer includes one or two valves and a high-pressure pump is used to form the droplets. As the liquids pass through the gap, 15-300 um wide, between the valve and seat, they are accelerated to speeds of 50-300 m·s$^{-1}$. In some embodiments, the droplets of the internal phase (first phase) shear against each other, are distorted and break up into smaller units. As the liquids exit from the gap, there is a sudden drop in pressure. Some cavitation may occur. In some embodiments, a valve is designed to cause the droplets impinge on a hard surface (breaker ring) set at 90 degrees to the direction of flow of the liquids after they emerge from the gap. All these mechanisms are expected to stress the droplets and contribute to their disruption. Droplets diameters of 0.1-0.2 um is expected to be attainable in pressure homogenizers. It is expected that there is an approximately inverse linear relationship between the logarithm of the homogenizing pressure and the logarithm of the droplet diameter produced by a pressure homogenizer. Homogenizer valves may be made of stainless steel or alloys such as stellite. More erosion-resistant materials such as tungsten carbide may be used, but tungsten carbide is not expected to be suitable for some food applications (which is not to suggest that tungsten carbide or any other material is disclaimed). In some embodiments, the homogenizing valve may not have any passages other than the primary flow passage. The small droplets of the internal phase may cluster together. These may be dispersed by passing them through a second valve. Some embodiments, thus, implement two-stage homogenization. The first valve may be set at a higher gauge pressure, 14-70 MPa, and the second valve may set be at a lower gauge pressure, 2.5-7.0 MPa.

In some embodiments, a hydroshear homogenizer is used to form the droplets (e.g. mixing two immiscible or partially miscible phases). In some embodiments, the first and the second phases are pumped into a cylindrical chamber at relatively low pressure, e.g., up to 2000 kPa. They may enter the chamber through a tangential port at its center and exit via two cone-shaped discharge nozzles at the ends of the cylindrical chamber. The liquids accelerate to a high velocity (sufficient to achieve Reynolds number greater than 2100) as they enter the chamber, spread out to cover the full width of the chamber wall and flow towards the center, rotating in ever decreasing circles. High shear develops between the adjacent layers of liquid, destabilizing the large droplets of the internal phase. In the center of the cylinder a zone of low pressure is expected to develop and cavitation, ultrahigh frequency vibration and shock waves are expected occur which all contribute to the break up of the droplets and the formation of an emulsion. Droplets sizes in the range 2-8 um is expected to be produced by this embodiment.

In some embodiments, a microfluidizer is used to form the droplets (e.g. mixing two immiscible phases). In some embodiments, separate streams of the first and the second phases may be pumped into a chamber under high pressure, e.g., 10 MPa. The liquids may be accelerated to high velocity, impinge on a hard surface and interact with each other. Intense shear and turbulence develop which is expected to cause breakup of the droplets of the internal phase and the formation of an emulsion. Very small emulsion droplets are expected to be produced by recirculating the emulsion a number of times through the microfluidizer.

In some embodiments, a membrane homogenizer is used to form the droplets. In some embodiments, the internal phase liquid is forced to flow through pores in a glass membrane into the external phase liquid, and an emulsion may be formed. Glass membranes may be manufactured with pores of different diameters to produce emulsions with different droplet sizes, e.g., in the range 0.5-10 um. Such membranes may produce o/w or w/o emulsions with very narrow droplet size distributions (polydispersity index of less than 1.2). In a batch version of this equipment, the internal phase liquid may be forced (e.g., pumped) through a cylindrical membrane partly (e.g., between 10% and 90% along a central axis)) immersed in the external phase (second phase) in a vessel. In a continuous version, a cylindrical membrane through which the external phase flows may be located within a tube, through which the internal phase flows. The internal phase may be put under pressure forcing it through the membrane wall into the external phase.

In some embodiments, an ultrasonic homogenizer is used to form the droplets (e.g. mixing two immiscible phases). In some embodiments, a liquid is subjected to ultrasonic irradiation, causing alternate cycles of compression and tension develop. This may cause cavitation in gas bubbles present in the liquid, resulting in the release of energy. This energy may be used to disperse the first phase in the second phase and produce an emulsion. In some embodiments, piezoelectric crystal oscillators may be immersed a reservoir. An ultrasonic transducer may include a piezoelectric crystal encased in a metal tube. When a high-intensity electrical wave is applied to such a transducer, the crystal oscillates and generates ultrasonic waves. In some embodiments, a transducer of this type is partly (e.g., more than 10%, 50%, or 90%) or entirely immersed in a vessel containing two liquid phases (e.g., the first phase and the second phase, as described above), together with an emulsifying agent or agents, and one phase may be dispersed in the other to produce an emulsion. For the continuous production of emulsions on an industrial-scale, mechanical ultrasonic generator may be used. A blade with wedge-shaped edges may be clamped at one or more nodal points and positioned in front of a nozzle through which the premixed emulsion is pumped. A resulting jet of liquid (the first and the second phases) emerging from the nozzle may impinge on the leading edge of the blade, causing the blade to vibrate at the blade's natural frequency, for example, in the range 18-30 kHz. This is expected to generate ultrasonic waves in the liquid, which is expected to cause one phase to become dispersed in the other, which is expected to cause the formation of an emulsion. The pumping pressure may be relatively low, for example, in the range 350-1500 kPa, and droplet diameters of the order of 1-2 um are expected to be produced. In some embodiments, a modified ultrasonic homogenizer may be used to form the droplets where in another mixing technique is coupled with ultrasonic waves to provide better bulk mixing and keep the form droplets dispersed equally in the solution. In some other embodiments, the first and second phases may be mixed with an emulsifier machine (for example a turbo emulsifier) and then an ultrasonic homogenizer may be used to further reduce the size of the formed droplets.

In some embodiments, a colloid mill may be used to form the droplets (e.g. mixing two immiscible or partially miscible phases). In some embodiments, the premixed emulsion ingredients pass through a narrow gap, in the range of hundreds of microns between a stationary surface (stator) and a rotating surface (rotor). In doing so, the liquid is expected to be subjected to shear and turbulence, which is expected to bring about further disruption of the droplets of the internal phase and disperses them throughout the external phase. The gap between the stator and rotor may be adjustable within the range 50-150 m. The rotor may turn on a vertical axis in close proximity to the stator. The clearance between them may be altered by raising or lowering the stator by means of an adjusting ring. Rotor speed ranges from 3000 rpm for a rotor 25 cm in diameter to 10 000 rpm for a smaller rotor 5 cm in diameter. Rotors and stators may have smooth stainless steel surfaces. Carborundum surfaces may be used when milling fibrous materials. Colloid mills may be jacketed with heat exchangers for temperature control. This type of mill is expected to be suitable for emulsifying viscous materials (e.g. 2000 centipoises and more). For lower viscosity materials the rotor is mounted on a horizontal axis and turns at higher speeds, up to 15 000 rpm. Mills fitted with rotors and stators with matching corrugated surfaces may also be used. The clearance between the surfaces may decrease outwardly from the center. The product may be discharged under pressure, up to 700 kPa. Incorporation of air into the product is expected to be limited and foaming problems are expected to be reduced in this type of mill relative to other approaches discussed herein.

In some embodiments, particles are generated using an electrostatic bead generator, with an electrostatic potential of 5-7 kV between a needle (with a hollow tube conveying liquid) feeding the first or second phase and a gelling bath (e.g., in which a distal end of the needle is disposed). In some embodiments, the first or second phase may be pumped at a rate of ~30 ml·h$^{-1}$ through the needle with an outer diameter of 0.4 mm and a voltage of 7 kV, and the distance between the needle and the gelling bath may be 10 mm, which is expected to cause capsules with a diameter of 500 um to be generated. Smaller capsules with diameters down to 200 um are expected to be formed at lower flow rates, lower voltages and smaller needles.

In some embodiments, a dripping method may be used to introduce droplets of first phase to the second phase. Detachment of the droplet from the nozzle tip is fundamentally governed by Tate's Law. Droplets formed by the dripping method are typically highly uniform in size and tend to be large (e.g., larger than 1 mm, depending on the liquid) because of the accumulation of drop volume at the nozzle tip before droplet breakup. It is expected that the droplet size may be reduced by promoting droplet breakup by applying external forces to an as-yet-unreleased droplet, such as air-driven shearing, forced vibration, electrostatic potential, and centrifugal force, actuators for which may be coupled to an orifice plate through which droplets are formed. Some embodiments may produce monodisperse capsules with sizes in the sub-millimeter range (e.g., 100-1000 um), and they are expected to achieve higher capsule production rates when compared with the other dripping method. The dripping method may also be used to produce liquid-core capsules with either aqueous- or oil-phase cargo. To produce aqueous-core capsules, the cargo may be pre-mixed with divalent cations before its dropwise addition to a first or second phase. Upon contact with the first or second phase, divalent cations at the droplet surface are expected to cross-link with the alginate polymer to form a continuous shell that encases the aqueous core. Some embodiments form capsules with inverse gelation. In some embodiments, both the first or second phase and cargo (either aqueous or oil phase) may be pre-templated into compound droplets using a concentric nozzle (with alginate as the outer flow and cargo as the inner flow). The compound droplets with cargo as the inner phase may then be collected in a gelling bath to solidify the shell. Some embodiments form capsules with co-extrusion. The primary drawback of using the dripping method to form droplets or capsules is the low production rate in terms of droplet number per unit time (which is not to suggest that this or any other subject matter is disclaimed). The formation of droplets is on a drop-by-drop basis, and the maximum working flow rate is often limited by the critical velocity before the extruded alginate liquid merges into a jet. One way to increase the process productivity to an industrial scale is by using multiple nozzles.

In some embodiments, particles are generated by atomization techniques. Some embodiments disperse the first phase into aerosolutions that may be gelled to form microparticles. Various mechanisms by which the first or second phase may be atomized include the following: (i) pressure nozzle, (ii) co-axial nozzle, and (iii) rotary atomization. In some embodiments, the injecting solution may be extruded at a high velocity into quiescent air and fragmented into droplets by the drag force between the fluids. In some embodiments, the injecting solution is extruded by a high-velocity, co-flowing stream of air. The co-axial airflow exerts drag on the first or second phase liquid surface, which then disintegrates into tiny droplets. The breakup of the solution thread and droplet is expected to occur when the dynamic pressure of the co-axial gas exceeds the pressure inside the liquid by a threshold amount. In some embodiments, the first or second phase may be fed onto a disk or wheel that rotates at a high speed, e.g., greater than 100 rotations per minute (RPM), greater than 400 RPM, or greater than 600 RPM. The resulting centrifugal force is expected to spread the first or second phase onto the disk into a thin sheet (e.g. less than 100 micrometers, or less than 50 micrometers). The first or second phase eventually discharges at the peripheral edge of the disk as droplets that are smaller than those existing before discharge. Some embodiments use spray nozzles that are employed in industry for spray drying. The mean size of the particles formed may be altered over a wide range, e.g., from 10 to 100 um. In some embodiments, ultrasonic atomization may be used to produce microparticles or microcapsules with mean sizes of 50-110 um. Generally, the size distribution of particles formed by the atomization method is expected to be broad because of the chaotic disruption of the liquid thread or droplet under turbulent conditions. Nevertheless, this method is industrially attractive because of its high productivity and is there-fore useful in applications that do not require stringent control over the size distribution.

In some embodiments, particles are generated by liquid-liquid techniques. Some embodiments disperse a first or second phase in a continuous phase of immiscible liquid (or partially miscible), which is expected to form a template of water-in-oil (W/O) emulsion prior to gelling. Some embodiments implement emulsification methods. The oil phase may be vegetable or mineral oil. Some embodiments may be used to produce small alginate capsules, e.g., with a mean size diameter ranging from 1 to 1000 um. The factors influencing the droplet size profile in the emulsification method are expected to include the alginate concentration (or viscosity of the first or second phase), gelling conditions, and surfactant formulation. Channeled emulsification may be used to disperse the droplets. In some embodiments, the droplets may be formed one drop at a time from one channel, and the diameter of the resulting droplets may be limited by the length of the channel. Monodisperse droplets may be formed using uniform channel openings, such as those used in microfluidics and membrane emulsification. Alternatively, or additionally, droplets may be dispersed by non-channeled emulsification. Some embodiments cause the turbulent mixing of immiscible liquids through mechanical stirring by a rotor or stator or high-pressure homogenizers. The resulting droplets are expected to have a broader size distribution than those formed via channel emulsification because a liquid-liquid interface is created through flow turbulence. Water in oil (W/O) emulsions are expected to form capsules immobilizing hydrophilic or large cargos, whereas oil in water in oil (O/W/O) emulsion templates are expected to form microcapsules loaded with lipophilic cargos. Some embodiments implement an emulsification method referred to as the non-channeled method. Some embodiments use mechanical stirring, e.g., at stirring speeds below 1000 RPM. The size of the capsules formed is expected to be inversely proportional to the energy input during agitation. This method is expected to produce capsules with a large range of mean size diameter between 20 and 1000 um, but the particle size distribution is expected to be generally broad and polydisperse. In some embodiments, non-channel methods, such as high-speed and high-pressure homogenization are used to produce capsules with smaller mean sizes and size distributions that are narrower and unimodal compared with those obtained by mechanical stirring.

In some embodiments, particles are generated by using microfluidics. Several microchannel may be used to generate calibrated droplets depending on the type of technology used for the fabrication of the microfluidic devices. For example, the inner diameter of a microchannel may be 500, 100, 10, or 1 micrometer. With planar chips, designed using soft lithography or laser etching fabrication, examples of configurations that may be used include the following two implementations. Periodic trains of monodisperse droplets may form by colliding two immiscible fluids streams at a T-shaped junction, or periodic trains of monodisperse droplets may form by using a flow focusing microdevice (FFD), where a 2D planar co-axial stream is forced to flow through a small orifice (e.g. diameter in the range of 200 micrometers). With both configurations, experiments may be performed either by imposing the flow rates or the pressure drop of the various streams. In each case, the mechanism of droplet formation which results from a subtle interplay between confinements, viscous and capillary stresses is expected to cause the production of periodic trains made of monodisperse droplets with extremely narrow size distribution. The mean droplet size is expected to be fine-tuned by adjusting the flow parameters of the various streams from 10 typically the lateral size of the channels used, up to a few hundreds of microns. The mean droplet size is expected to be decrease with the flow rate and viscosity of the continuous phase and increases with the flow rate of the dispersed phase. To decrease the droplet size, some embodiments may break the drops into controlled daughter droplets at a T junction or at a junction of various other angles. This passive method of break-up is expected to facilitate modulating the size ratio of daughter droplets by modifying the hydrodynamic resistances of the two junction's outlets. It is expected that this passive method of break-up may be carried out in succession without increasing the polydispersity of the droplets until their dimensions are larger than the channel dimensions. In some embodiments, monodisperse drops in larger sizes may be generated using double capillary devices, by injecting the disperse phase through the co-flowing matrix fluid the setup includes a blunt calibrated needle with a diameter $\varphi$ of typically a few hundreds of micrometers, centered to a cylindrical glass capillary with a diameter of $D \geq \varphi$. Using independent syringe pumps, two immiscible fluids (the first and the second phases) may be respectively infused through both the needle and the annular gap between it and the internal capillary wall. The flow rates may be independently controlled and adjusted in order to form monodisperse droplets of the dispersed phase in the continuous one. Both W/O and O/W droplets may be prepared provided that the wetting properties of the internal capillary wall are compatible with the continuous phase. Such devices then are expected to allow the extension of the preparation of well calibrated emulsions up to sizes of a few millimeters. Emulsions with smaller sizes (typically a few tens micrometers) are expected to be generated by using a double capillary device, which may include a cylindrical capillary tube co-axially nested within a square glass.

In some embodiments, the size of the particles formed by liquid-liquid methods is reduced by using a solvent diffusion method. The alginate may be mixed with a solvent before dispersing the solution into droplets in an immiscible phase. Upon droplet formation, the solvent may be removed, thereby causing the alginate droplets to shrink. The addition of divalent cations causes the alginate droplets to gel.

In some other embodiments, a combination of techniques discussed above is used to form the droplets. Such combinations include using the mixing techniques in parallel or one after each other. In some embodiments, different types of particles with different encapsulants are formed with different ones of the above techniques and combined into a single host material.

9. Taste

In some embodiments, particles are expected to mask an unpleasant flavor of encapsulated components in order to keep the taste of the host product pleasant, in some cases without affecting mouthfeel, and in some cases, while remaining shelf stable. For example, some consumers may not like the taste of some type of alcohol while enjoying the effect of alcohol consumption. Addition of alcohol-containing particles to fruit juice or various other types of beverage is expected to provide the opportunity for the consumer to enjoy the effect of alcohol consumption without experiencing the unpleasant flavor of alcohol.

In some embodiments, the effectiveness of masking a flavor of an encapsulated component is calculated by measuring the concentration of that component in the medium in which the particles are dispersed. For example, if whey protein is encapsulated, the concentration of the whey protein is monitored and measured in the medium in which the particles are dispersed. As the whey protein is released from inside the particles into the medium, the concentration of the whey protein is changed in the medium and by monitoring this change, the effectiveness of the masking the flavor of the whey protein by particles and the release kinetics of the whey protein is calculated.

10. Permeability

In some embodiments, the particles contain an oil phase. In some such cases, permeability of the particles is less of a concern compared to particles containing water miscible components such as alcohol and proteins. Instead of permeability, stability of the particles is often more important in case of oil-containing particles. In some such cases, the shell of the particles may be made of less polymers (such as alginate) and more stabilizers (such as surfactants). Stabilizers may be selected from the group of non-ionic, anionic, cationic or amphoteric emulsifiers. The non-ionic emulsifiers used may be different emulsifiers from the group consisting of partial fatty acid esters, fatty alcohols, sterols, polyethylene glycols, such as ethoxylated fatty acids, ethoxylated fatty alcohols, and ethoxylated sorbitan esters, sugar emulsifiers, polyglycerol emulsifiers, and silicon emulsifiers. The anionic emulsifiers used may be different emulsifiers from the group consisting of soaps, such as sodium stearate, fatty alcohol sulfates, mono, di- and trialkyl phosphoric acid esters and the ethoxylates thereof, fatty acid lactate esters, fatty acid citrate esters, and fatty acid citroglycerin esters. Cationic emulsifiers may be, for example, quaternary ammonium compounds having a long-chain aliphatic group, such as distearyldimonium chloride. Amphoteric emulsifiers may include different emulsifiers from the groups consisting of alkylamininoalkane carboxylic acids, betaines, sulfobetaines, or imidazoline derivatives. In some embodiments, naturally occurring emulsifiers are used such as beeswax, lecithin, and sterol. In some embodiments, the final product is a stable oil in water emulsion.

In some embodiments, permeability of the particles may be tuned to prolong the shelf-life. In some embodiments, calcium chloride and zinc sulphate are used to cross-link alginate microspheres prepared by an emulsification method. The particles cross-linked by a combination of these two salts are expected to show different morphology and slower release compared with those cross-linked by the calcium salt alone. Zinc cations may interact with the alginate molecules to a greater extent than calcium cations. Zinc and calcium cations are expected to bind at different sites of the alginate molecule The zinc cations may be less selective and hence produce more extensive cross-linking of alginate which is expected to cause delayed release of the encapsulated first phase.

Permeability of particles may be further tuned by addition of mono and polysaccharides such as sucrose and chitosan. In some embodiments, the stability of particles is tuned by the amount of chitosan bound to the particles. When the particles are made by dropping a solution of sodium alginate into a chitosan solution (one-stage procedure), all the chitosan is located in a thin alginate/chitosan membrane on the surface. The permeability of these particles may be reduced by increasing the chitosan molecular weight and the degree of acetylation. The addition of several layers of alginate and chitosan is expected to minimize the permeation rates. In some embodiments, multilayers of alginate or chitosan are coated to control the permeation of the encapsulated first phase.

In some embodiments, the permeation of particles may be controlled by varying the ratio of guluronic acid (G-alginate) to mannuronic acid (M-alginate) content. While alginates with high guluronic acid content develop stiff porous gels that maintain their integrity for long periods of time, alginates rich in mannuronic acid residues are expected to develop softer, less porous particles that tend to disintegrate faster. The affinity of alginates toward divalent ions may decrease in the order Pb>Cu>Cd>Ba>Sr>Ca>Co, Ni, Zn>Mn. Ca binds to G- and MG blocks, Ba to G- and M-blocks, and Sr to G-blocks solely. Different affinity is expected to influence the physical properties of ionically crosslinked alginate gels. High-G alginates are expected to be influenced by using ions of high affinity (Ba or Sr), whereas for high-M alginates no effect is observed on stability or permeability when using Ba or Sr in the gelling solution In some embodiments, the permeation of the particles is further controlled by coating a layer or layers of polycations such as polyethyleneimine, poly-L-ornithine (PLO), poly-D-lysine, poly-L-lysine and polymethylene-co-guanidine. In some other embodiments, use of epimerized alginate or covalently cross-linked alginate may lead to reduced permeability of the particles. In some embodiments, use of cations with higher affinity toward alginate may lead to reduced permeability of the particles.

In some embodiments, permeation of the particles is further controlled by coating a layer or layers that are resistant to acidic breakdown as well as pH differentials; such layers may protect the active ingredients in the harsh conditions (e.g., surrounding medium before consumption or acidic environment of digestive tract) and release the active ingredients (e.g., encapsulants) in benign environment for probiotics, proteins, and peptides (e.g. in the colon that has a much lower concentration of proteolytic and other enzymes.) A much lower concentration of proteolytic and other enzymes are expected to be populated in the colon, as it is a much more benign environment for proteins and peptides as well as other biological entities such as carbohydrates and nucleic acids.

11. Controlled Release

In some embodiments, the particles have a kind of "extended" or "delayed" release composition (relative to non-encapsulated versions of active ingredients), wherein the encapsulated materials are released over a prolonged period. Non-limiting examples include food and beverage, oral care, personal care, and drug industries.

In some embodiments, the release rate of encapsulated components from the particles is determined by measuring the concentration of encapsulated components in the solution in which the particles are dispersed.

In some embodiments, the particles comprise a pH sensitive component such that known dissolution characteristics may be imparted to the encapsulant. Thus, for example, encapsulating compositions may be prepared according to methods known in the art such that upon exposure of the particles to a specific elevated or decreased pH, the encapsulating material rapidly dissolves, hardens, becomes permeable or the like. In some embodiments, for example, the encapsulant is designed to dissolve in a solution of reduced pH. Thus, contact of the particles of this embodiment with acidic environment of stomach is expected to result in rapid dissolution of the particles, and release of the contained alcohol composition into the stomach.

Release of an encapsulated component from a particle may be caused by a variety of mechanisms, including mechanical particle rupture, particle wall dissolution, particle wall melting or diffusion through the wall. In some embodiments, the difference in the concentration of the encapsulated component between inside and outside the shell of the particle cause the mass transfer from the side with higher concentration to the side with lower concentration. For example, if the particles are encapsulating vodka and are dispersed in water, the concentration of the alcohol molecules is higher inside the particles compared the outside. Therefore, the alcohol molecules will migrate through the pores of the polymeric shell of the particles from inside toward outside the particles because there is an effective osmotic pressure gradient between the interior and exterior of the particles. Same phenomenon will cause the water molecules to be transferred inside the particles. Therefore, the concentration of the alcohol and water will become equal in inside and outside of the particles eventually. Reducing the size of the pores of the polymeric shell or the concentration difference between two sides of the polymeric shell is believed to prolong the release kinetics. In addition, low molecular interaction of the encapsulated component with the outside medium is also believed to reduce the release rate. For example, if oil is encapsulated inside the particles and the particles are dispersed in water, the oil molecules have a very low and weak interaction with water molecules (low solubility) and therefore oil molecules do not want to be transferred from inside the particles to the hydrophilic medium outside the particles.

In some embodiments, a solution may contain particles with different release kinetics. In some embodiments, a solution containing particles with different release kinetics may offer almost steady release of the encapsulated ingredients over a prolonged period of time. For example, a solution may contain particles, encapsulating protein, with different release kinetics. Consumption of such a solution may lead to steady delivery of protein to a consumer's body over a prolonged period of time. In some embodiments, the prolonged period of time may be 1, 2, 5, 10, or 20 hours. Delayed release may also be characterized relative to the active ingredient in unencapsulated form, producing release curves that are delayed in their initial phases by 20% longer, 50% longer, 100% longer, 200% longer or more, and span after the start of release 20% longer, 50% longer, 100% longer, 200% longer or more than the span of time over which release occurs in unencapsulated form.

In some embodiments, the release kinetics of active ingredients and the extent of absorption in humans or other in vivo may be studied by Mass-balance pharmacokinetic studies, Absolute bioavailability studies, In vivo or in situ intestinal perfusion studies (e.g., in animals or humans), In vitro permeation studies (e.g. in animals or humans), and other techniques known in the art.

In some embodiments, a particle may have a control release mechanism to release an active ingredients immediately (e.g., after consumption by a mammal, like a human), after some delay (e.g., 2, 4, 8, or 12 hours after consumption), an extended release (e.g. constant release over a window of 0.5, 1, 2, 4, 6, or 12 hours), step-wise release (e.g. release 50% of active ingredients in the first hour, no release in the second hour, and release the other 50% of the active ingredients in the third hour after consumption), or a combination thereof. Such controlled release mechanism may be achieved through a single or multiple layers in a particle. In some cases, the same encapsulant may be encapsulated multiple different ways in different particles in a host alimentary product, e.g., to produce a spike in release after a first amount of time and then a different spike in release after a second amount of time. Or different payloads may be encapsulated in different ways to release at different times, e.g., releasing a stimulant after a first amount of time and an anti-inflammatory agent later after a second amount of time to aid in workouts and recovery. In some embodiments, an in-vitro dissolution rate of particles and the release profile of active ingredients was measured by USP apparatus type II or type III at various conditions (e.g. at 37° C. and 50 rpm, in pH 6.8 buffer). Such conditions were chosen to simulate the surrounding medium of particles before consumption (e.g. in a beverage or an energy shot) and after consumption at different stages of digestive tract (e.g. colon or small intestine). The term USP apparatus used herein is described e.g., in the United States Pharmacopeia XXV (2002).

12. Bioavailability

In some of the embodiments where lecithin is used as emulsifier for the production of O/W emulsions, the resultant nano-emulsions are highly fluid and appear transparent or translucent. This transparency or translucency infers the presence of droplets smaller than 50 nm suspended in the continuous aqueous phase. For applications where bioavailability is of importance, the reduction in particle size proves to be beneficial; as the increased surface area to volume ratio of the particles result in a higher interaction rate between the particle and its surroundings. Conversely, when the droplet diameter exceeds around 100 nm, nano-emulsions appear hazy or white due to significant multiple scattering of light. The physical stability and shelf life of nano-emulsions is superior to that of macroscopic emulsions. The droplet size distribution is, for some use cases, one of the most important physical characteristics of nano-emulsions. In this disclosure, it is determined by dynamic light scattering (DLS). Furthermore, stability of the composition is measured using a technique selected from the group consisting of measuring drop size, light scattering, focused beam reflectance measurement, centrifugation, rheology and any combination thereof.

In some embodiments, absorption enhancers may be used to promote membrane permeability and improve oral bioavailability. Sodium N-[8-(2-hydroxybenzoyl)amino]caprylate (SNAC) is an example of an absorption enhancer.

13. Products

Some embodiments of the present application relate to food particles obtained by the method described above. Some embodiments discloses a method of producing a spherical alimentary-related particles that contains in its interior substances, characterized in that the diameter of the spherical food particle is in the range of 100 nm to 10 mm or, in some other embodiments, in the range of 1 micrometer to 1 mm or, in some other embodiments, 100 micrometers to 800 micrometers or, in some other embodiments, 300 micrometers to 500 micrometers.

In some embodiments, the particles of the present disclosure may be provided as a food composition in combination with a food carrier, including but not limited to food bars (e.g., granola bars, protein bars, candy bars), cereal products (e.g., oatmeal, breakfast cereals, granola), bakery products (e.g., bread, donuts, crackers, bagels, pastries, cakes), dairy products (e.g., milk, yogurt, cheese), beverages (e.g., milk-based beverages, sports drinks, fruit juices, teas, soft drinks, alcoholic beverages, bottled waters), beverage mixes, pastas, grains (e.g., rice, corn, oats, rye, wheat, flour), egg products, snacks (e.g., candy, chips, gum, gummies, lozenges, mints, chocolate), meats, fruits, vegetables or combinations thereof. Food compositions may comprise solid foods. Food compositions may comprise semi-solid foods. Food compositions may comprise liquid foods. A composition in a liquid form may be formulated from a dry mix, such as a dry beverage mix or a powder. A dry mix may be suitable in terms of transportation, storage, or shelf life. The composition may be formulated from the dry mix in any suitable manner, such as by adding a suitable liquid (e.g., water, milk, fruit juice, tea, or alcohol).

In some embodiments, the particles of the present disclosure may comprise pet or other animal products, such as animal food (e.g., dog food, cat food), treats, and nutritional supplements (e.g., liquids, sprays, or powders for application to food or water). These compositions may be formulated for or administered to domestic or pet animals (e.g., dogs, cats, small mammals, birds), livestock and other farm animals (e.g., cows, pigs, horses, sheep, goats), zoo animals, or any other vertebrates. Compositions for administration to animals may be formulated with microencapsulated cannabinoid-rich oil or non-encapsulated cannabinoid-rich oil, alone or in combination with essential oils, terpenes, and other components described herein. Compositions for administration to animals may be mixed into feed or water, prepared for spraying application (e.g., mixed in glycerin), for intravenous administration (e.g., in a syringe or an IV bag), in salves, vitamins, liquid vitamin pumps, treats, or other forms.

In some embodiments, the particles are intended as food product additives, including during fruit preparation, in yogurts, or as an ice cream topping. In some embodiments, the particles may be served at varying temperatures: from frozen, to slightly chilled, to room temperature, warm and even quite hot. In some embodiments, other types of polysaccharides are used instead of sodium alginate such as agar/agarose, k-carrageenan, pectin, gellan gum, and chitin.

In some embodiments, the particles will have an expected shelf life of about 1 year. In some other embodiments, the particles will have an expected shelf life of about 6 months. In some other embodiments, the particles will have an expected shelf life of about 2 months. In some other embodiments, the particles will have an expected shelf life of about 1 month. In some other embodiments, the particles will have an expected shelf life of about 1 week. In some other embodiments, the particles will have an expected shelf life of about 1 day. Such particles should tolerate a wide range of temperatures without affecting quality. The permeability of the particles is another factor in determining the shelf life of the particles. In some embodiments, the particles are stable in the temperature range of 0-40 degrees of Celsius. In some other embodiments, the particles are stable in the temperature range of 15-30 degrees of Celsius.

In some embodiments, the particles may be dispersed in a lubricant. Particles may contain various types of encapsulants, including essential oils and analgesics.

In some embodiments, the particles may be dispersed in a sanitizer. Particles may contain various types of encapsulants, including essential oils and antibacterial ingredients.

14. Characterization and Uses

In some embodiments, shelf-life of the products is predicted using the data collected during accelerated testing to produce a model for prediction. The data, in some embodiments, is matched with common reaction kinetic formulas or extrapolated to predict capsule performance over future time points and the shelf-life of the product. In some embodiments, sufficient number of experiments are performed to test the different storage stability variables, such as temperature, time and humidity. In some embodiments, 50 experiments at different conditions were performed. In some embodiments, 100 experiments at different conditions are performed. In some embodiments, more 100 experiments at the same conditions are performed. In some embodiments, for flavors, orange oil is used an example of an encapsulant. Orange oil is a flavor component that may be encapsulated to control release and prevent oxidation. In some embodiments, to compare the performance of orange oil encapsulated particles, samples are analyzed for limonene and limonene oxide formation over the course of 70 days at 37° C.

In some embodiments, in situ particle performance is analyzed using an oxygen sensitive fluorescent dye to monitor the oxygen exposure of encapsulants. In some embodiments, the stability and prediction of shelf-life of particles is dependent upon the particle formulation, system metrics, and final application.

In some embodiments, the dispersed phase of a product (e.g., a beverage or an energy shot) includes one or more particles. The particles are stable and do not dissolve in the dispersion medium. In some embodiments, when the dispersion medium has a certain viscosity, the particles may stay uniformly dispersed throughout the dispersion medium. In some embodiments, the particles may be settled at the bottom of a dispersion medium or be floating at the top of the dispersion medium and then dispersed by shaking the dispersion medium.

In some embodiments, a dispersion medium may include pH modifiers for modifying the pH of the dispersion medium. The pH of the dispersion medium may need to be adjusted with the pH modifier in order to provide a medium that will not degrade the particles dispersed therein at a fast rate to provide the desired shelf life stability.

In some embodiments, the formed particles may be encapsulated again in bigger particles. In some embodiments, the reason behind such process may be increasing the shelf life. In some other embodiments, the reason behind such process may be achieving different release timelines for different components where the encapsulated materials inside smaller particles would be released later than the encapsulated materials inside the bigger particles. In some embodiments, there is one particle inside the bigger particles. In some other embodiments, there are multiple small particles inside one big particle. In some embodiments, it may be a combination of the previous two.

In some embodiments, the term "adding" refers to joining two or more things together. In some embodiments, adding comprises joining two ingredients together.

Herein, the term "dissolving" refers to converting the particle of a compound to a lower state of stability and volume. In some embodiments, dissolving comprises forming a solution by placing a solid into a liquid. In some embodiments, dissolving comprises forming a homogenous mixture of a liquid and oil. In some embodiments, dissolving comprises forming a homogenous aqueous mixture.

Herein, the term "solution" refers to a mixture or formulation of two or more compounds. In some embodiments, the solution is a mixture of two or more liquids.

Herein, the term "spraying" refers to dispersing a compound or compounds into fine particles or droplets. In some embodiments, spraying includes dispersing a liquid into a fine mist.

Herein, the term "evaporating" refers to converting a compound into the vapor phase. In some embodiments, evaporating includes heating a compound. In some embodiments, evaporating comprises changing pressure. In some embodiments, evaporating includes turning a liquid into a gas.

Herein, the term "combining" refers to merging, incorporating, fusing, blending, or mixing. In some embodiments, combining comprises mixing compounds to form a homogeneous mixture.

In some embodiments, the encapsulation process is performed at ambient temperature. An increase or decrease in temperature, as well as increasing the production costs of the particles, may affect the viscosity, density and surface tension of the oily and aqueous phases present in the process. In some cases, the process may be tuned to accommodate other temperatures.

The term "about," "nearly," "substantially," and the like, as used herein refers to within +/−20% of the designated amount, unless indicated otherwise, which is not to suggest that terms lacking these qualifiers are to be read as limited to the exact recited value if industry practice is to allow for some tolerance around the recited value (e.g., if one of ordinary skill in the art would understand reference to 10% alcohol concentration in a host beverage to encompass anything in the range of 8% to 12% under industry practice and typical variation in a manufacturing process around a target value).

In some embodiments, the particles are separated from one another by a host beverage, e.g., less than 20%, less than 10%, less than 1%, or less than 0.01% of the particles are in contact under the above solubility test.

It will be appreciated that preferred properties of a particle (e.g., size, material, structure, and etc.) may be readily determined by those skilled in the art by evaluating the application and product. It is the combination of materials, method and form of application that produce the desired particle, which one can determine only from experiments.

Figure 12:
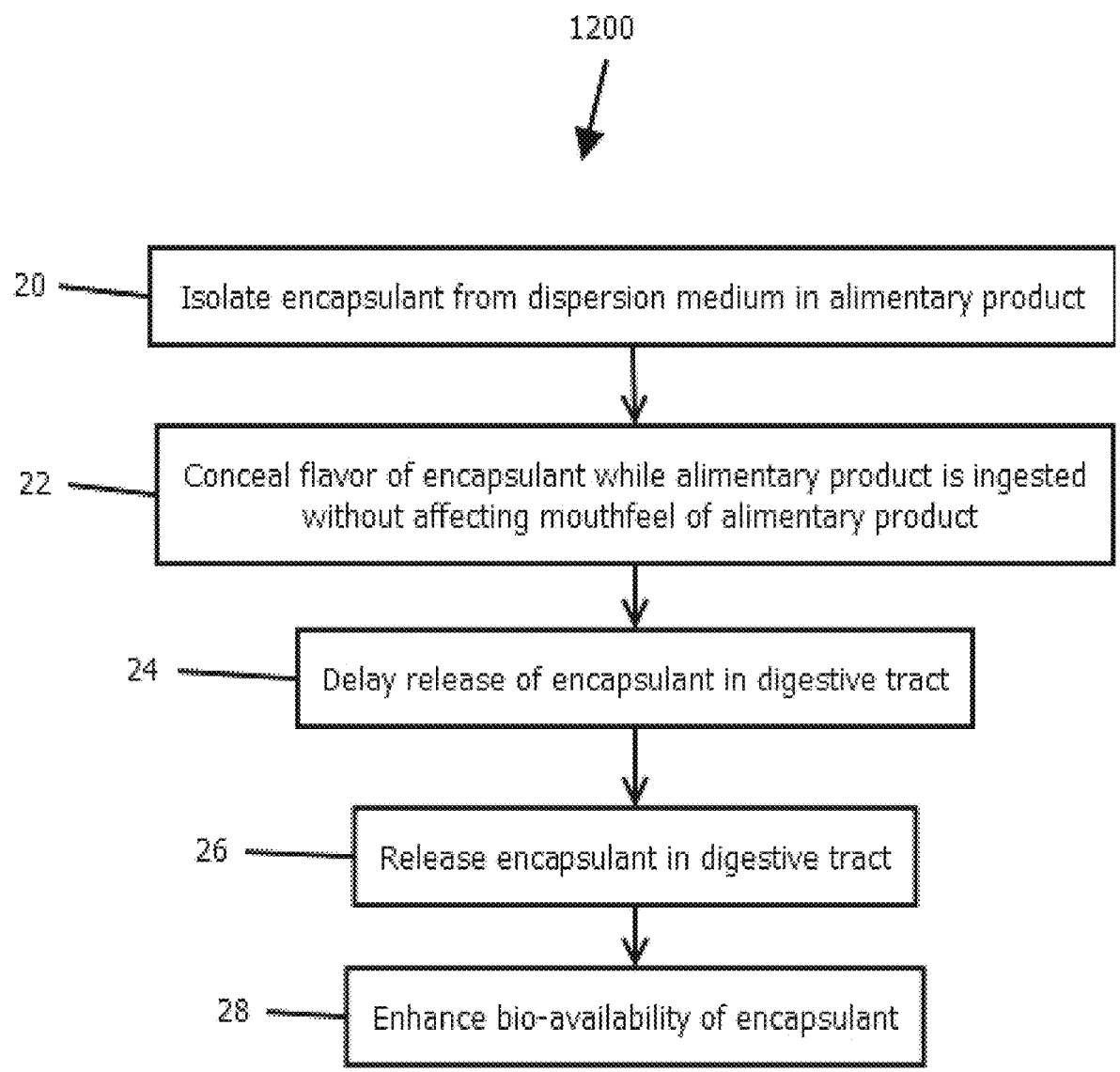
FIG. 12 is a flow diagram showing a method of operation, in accordance with some embodiments of the present disclosure.

FIG. 12 depicts a method 1200 of operation, in accordance with some embodiment, and may generally include adding some particles, in accordance with some embodiments of the present disclosure, to a dispersion medium in a container, as an alimentary product, to achieve some of the following steps: isolating encapsulants from the dispersion medium in the alimentary product as shown in block 20, concealing (e.g., fully or partially) the flavor of encapsulants (or at least some of them) while the alimentary product is ingested without affecting mouthfeel of the alimentary product as shown in block 22, delaying (or controlling) the release of the encapsulants (or at least a portion of the encapsulants) in the digestive tract as shown in block 24, releasing the encapsulants in the digestive tract as shown in block 26, and enhancing the bioavailability of the encapsulants as shown in block 28.

Figure 13:
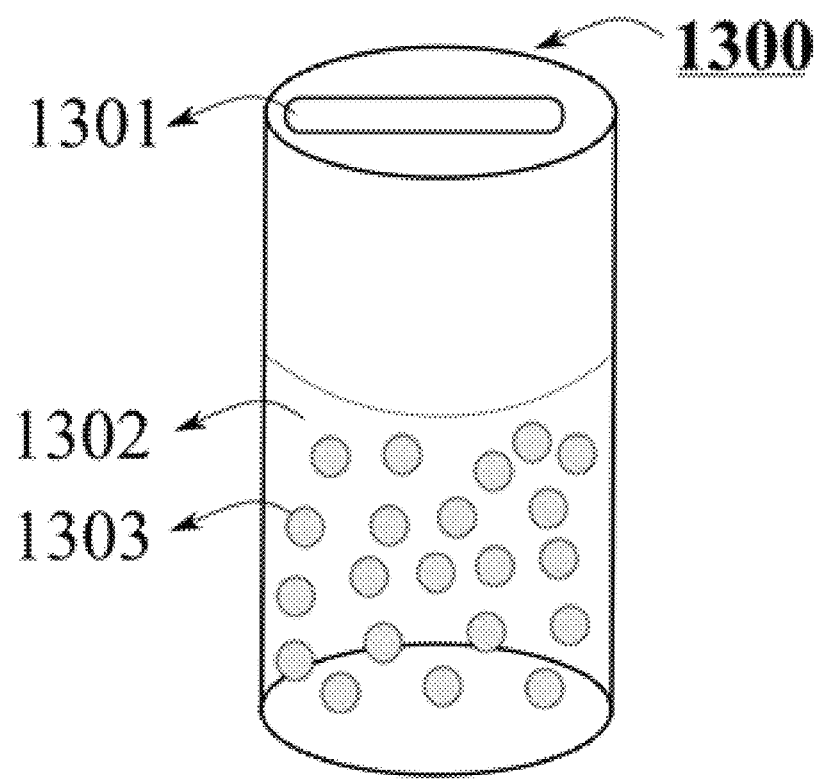
FIG. 13 is a perspective view of a container with particles dispersed in a medium, in accordance with some embodiments of the present disclosure.

FIG. 13 illustrates a container (e.g., a can or a bottle) 1301 containing a host medium (e.g. a beverage) 1302 and particles 1303, containing an encapsulant, dispersed in the host medium. The container 1300 may have an opening. In some embodiments, the particles may be uniformly dispersed throughout the host medium. In some embodiments, the particles may be settled (e.g. fully or partially) at the bottom of the container. In some embodiments, the particles may be floating (e.g., fully or partially) on the top of the host medium. in some embodiments, some of the particles may be in surface contact with each other. In some embodiments, particles are isolated from each other by the host medium.

In some embodiments, the particles similar to the particle shown in FIG. 4 are used in immune booster products. Such products may be packaged in 2 oz. (or 1 oz.) format to deliver 20 mg ionic zinc, 1000 mg vitamin C, 600 IU and vitamin D3. In some embodiments, the 2 oz. format contain 20 mg CBD as well. Containers may be less than or equal to 50 gallons, 5 gallons, 1 gallon, 1 quart, 12 oz, 5 oz, or 2 oz.

In some embodiments, the particles may contain encapsulants with antimicrobial activities. In some embodiments, the particles may contain encapsulants with antirhinoviral activity (e.g. ionic zinc).

In some embodiments, particles, containing encapsulants with antirhinoviral activity, may be used in an immune booster product to enhance the taste (e.g. by masking the flavor of bad tasting ingredients such as ionic zinc), keep the encapsulants in the right format (e.g. keep the zinc in ionic format by a complexing agent such as agar), or provide controlled released at various stages of digestive tract (e.g. oropharyngeal region).

In some embodiments, particles, containing encapsulants with antirhinoviral activity, may be used as in dental-related products such as mouthwash.

In some embodiments, particles may be dispersed in a hydrogel medium, with sticky texture (e.g. xanthan gum), to provide a coating in oropharyngeal region. The particles may contain encapsulants to be released in the oropharyngeal region. The release may be controlled to take place over an extended period of time (e.g. 1, 5, 10, 30, 90, 150 minutes).

In some embodiments, the surface of particles may be coated with various coatings to better meet the requirements of an intended application. For example, the surface of the particles may be coated with a sticky layer. Such sticky particles may be used to deliver encapsulants to the oropharyngeal region with controlled release kinetics. For example, such particles may contain ionic zinc as an encapsulant to be released in the oropharyngeal region to inhibit the normal cleavages of viral polypeptides (e.g. SARS-CoV-2).

In some embodiments, particles may be added to a cream or a lotion to provide controlled release of encapsulants (e.g. essential oils or CBD). For example, the particles may be added to a skin care formulation, where the particles may seal moisture into the skin to prevent drying and re-hydrate dried skin.

In some embodiments, particles may be added to a hand sanitizer to provide an extended release of an encapsulant with antimicrobial activities (e.g. essential oils or ethyl alcohol).

In some embodiments, particles may be used to provide controlled release and targeted delivery of pharmaceuticals in the conserved regions of influenza for effective antiviral activity.

In some embodiments, particles may be used in an antimicrobial emulsion. Such antimicrobial composition may include essential oils stabilized in a hydrogel medium.

It will be appreciated that any encapsulating, non-toxic material may be used according in some embodiments to deliver the ethanol composition for recreational purposes. However, it is preferred for the encapsulating material to be digestible, in instances where the encapsulating material is designed to be ingested along with the contents. In such instances, the encapsulating material should be comprised of gelatin or alginate or like digestible material, and the particles may be designed for breakage in the consumer stomach and upper intestine. To that end, it may be, in addition, desirable for the particles to be coated with a sugar coating or the like, such that as the particles contacts the salivary juices in the mouth, additional saliva is produced, the particles have a pleasant taste, and as the sugar dissolves, it ensures ease of swallowing the broken or unbroken particles.

It will be appreciated from this disclosure that it is preferred for the encapsulating material to be capable of sustaining various concentrations of ethanol within the internal compartment, without dissolution into the ethanol. It is also preferred for the encapsulating material to be of sufficient rigidity to sustain packaging and storage for from several minutes to several weeks or months. This goal is achievable using gelatin, if sufficient concentrations of gelatin are incorporated into the encapsulating material, or where the molecules constituting the gelatin particles are crosslinked with a cross-linking agent, such as but not limited to glutaraldehyde. Methods of achieving this goal are known in the art and therefore, are not discussed in detail here. Alternative encapsulating materials which meet these criteria include waxes, synthetics and the like, which are non-toxic and stable in the presence of ethanol compositions.

Having generally described some embodiments of this application, the following examples are provided to provide detailed written disclosure of some of the embodiments of this application. However, the scope of this application should not be construed as being limited by the specifics of these examples. Rather, the scope of this application should be determined through reference to the complete disclosure and the claims appended hereto. It should further be noted that while the following examples provide descriptions of specific compositions of matter, produced according to disclosed small-scale processes, those skilled in the art will appreciated that highly automated and mechanized, large-scale methods for producing the encapsulated products of this application come within the scope of this application.

The reader should appreciate that the present application describes several independently useful techniques. Rather than separating those techniques into multiple patent applications, applicants have grouped these techniques into a single document because their related subject matter lends itself to economies in the application process. But the distinct advantages and aspects of such techniques should not be conflated. In some cases, embodiments address all of the deficiencies noted herein, but it should be understood that the techniques are independently useful, and some embodiments address a subset of such problems or offer other, unmentioned benefits that will be apparent to those of skill in the art reviewing the present disclosure. Due to costs constraints, some techniques disclosed herein may not be presently claimed and may be claimed in later filings, such as continuation applications or by amending the present claims. Similarly, due to space constraints, neither the Abstract nor the Summary of the Invention sections of the present document should be taken as containing a comprehensive listing of all such techniques or all aspects of such techniques.

It should be understood that the description and the drawings are not intended to limit the present techniques to the particular form disclosed, but to the contrary, the intention is to cover all modifications, equivalents, and alternatives falling within the spirit and scope of the present techniques as defined by the appended claims. Further modifications and alternative embodiments of various aspects of the techniques will be apparent to those skilled in the art in view of this description. Accordingly, this description and the drawings are to be construed as illustrative and are for the purpose of teaching those skilled in the art the general manner of carrying out the present techniques. It is to be understood that the forms of the present techniques shown and described herein are to be taken as examples of embodiments. Elements and materials may be substituted for those illustrated and described herein, parts and processes may be reversed or omitted, and certain features of the present techniques may be utilized independently, all as would be apparent to one skilled in the art after having the benefit of this description of the present techniques. Changes may be made in the elements described herein without departing from the spirit and scope of the present techniques as described in the following claims. Headings used herein are for organizational purposes and are not meant to be used to limit the scope of the description.

As used throughout this application, the word "may" is used in a permissive sense (i.e., meaning having the potential to), rather than the mandatory sense (i.e., meaning must). The words "include", "including", and "includes" and the like mean including, but not limited to. As used throughout this application, the singular forms "a," "an," and "the" include plural referents unless the content explicitly indicates otherwise. Thus, for example, reference to "an element" or "a element" includes a combination of two or more elements, notwithstanding use of other terms and phrases for one or more elements, such as "one or more." The term "or" is, unless indicated otherwise, non-exclusive, i.e., encompassing both "and" and "or." Terms describing conditional relationships, e.g., "in response to X, Y," "upon X, Y,", "if X, Y," "when X, Y," and the like, encompass causal relationships in which the antecedent is a necessary causal condition, the antecedent is a sufficient causal condition, or the antecedent is a contributory causal condition of the consequent, e.g., "state X occurs upon condition Y obtaining" is generic to "X occurs solutionely upon Y" and "X occurs upon Y and Z." Such conditional relationships are not limited to consequences that instantly follow the antecedent obtaining, as some consequences may be delayed, and in conditional statements, antecedents are connected to their consequents, e.g., the antecedent is relevant to the likelihood of the consequent occurring. Statements in which a plurality of attributes or functions are mapped to a plurality of objects (e.g., one or more processors performing steps A, B, C, and D) encompasses both all such attributes or functions being mapped to all such objects and subsets of the attributes or functions being mapped to subsets of the attributes or functions (e.g., both all processors each performing steps A-D, and a case in which processor 1 performs step A, processor 2 performs step B and part of step C, and processor 3 performs part of step C and step D), unless otherwise indicated. Further, unless otherwise indicated, statements that one value or action is "based on" another condition or value encompass both instances in which the condition or value is the solution factor and instances in which the condition or value is one factor among a plurality of factors. Unless otherwise indicated, statements that "each" instance of some collection have some property should not be read to exclude cases where some otherwise identical or similar members of a larger collection do not have the property, i.e., each does not necessarily mean each and every. Limitations as to sequence of recited steps should not be read into the claims unless explicitly specified, e.g., with explicit language like "after performing X, performing Y," in contrast to statements that might be improperly argued to imply sequence limitations, like "performing X on items, performing Y on the X'ed items," used for purposes of making claims more readable rather than specifying sequence. Statements referring to "at least Z of A, B, and C," and the like (e.g., "at least Z of A, B, or C"), refer to at least Z of the listed categories (A, B, and C) and do not require at least Z units in each category. Unless specifically stated otherwise, as apparent from the discussion, it is appreciated that throughout this specification discussions utilizing terms such as "processing," "computing," "calculating," "determining" or the like refer to actions or processes of a specific apparatus, such as a special purpose computer or a similar special purpose electronic processing/computing device. Features described with reference to geometric constructs, like "parallel," "perpendicular/orthogonal," "square", "cylindrical," and the like, should be construed as encompassing items that substantially embody the properties of the geometric construct, e.g., reference to "parallel" surfaces encompasses substantially parallel surfaces. The permitted range of deviation from Platonic ideals of these geometric constructs is to be determined with reference to ranges in the specification, and where such ranges are not stated, with reference to industry norms in the field of use, and where such ranges are not defined, with reference to industry norms in the field of manufacturing of the designated feature, and where such ranges are not defined, features substantially embodying a geometric construct should be construed to include those features within 15% of the defining attributes of that geometric construct. The terms "first", "second", "third," "given" and so on, if used in the claims, are used to distinguish or otherwise identify, and not to show a sequential or numerical limitation. As is the case in ordinary usage in the field, data structures and formats described with reference to uses salient to a human need not be presented in a human-intelligible format to constitute the described data structure or format, e.g., text need not be rendered or even encoded in Unicode or ASCII to constitute text; images, maps, and data-visualizations need not be displayed or decoded to constitute images, maps, and data-visualizations, respectively; speech, music, and other audio need not be emitted through a speaker or decoded to constitute speech, music, or other audio, respectively.

The present techniques will be better understood with reference to the following groups A-G, each including enumerated embodiments:

Group A:
1. A composition including a dispersion medium including: an aqueous solution; a first active ingredient; a flavor agent; and a first type of polymer; and a dispersed phase including: a population of particles, each particle including: a core including: a second active ingredient a second type of polymer; and an aqueous solution; a shell, substantially surrounding the core, the shell including: a third type of polymer; a plurality of lipophilic carriers; and a third active ingredient; and a plurality of emulsifying agents.
2. The composition of embodiment 1, wherein: at least 50% by weight of the second active ingredient is released within 2 hours after consumption; and at least 70% by weight of the third active ingredient is released within 2 hours after consumption.
3. The composition of embodiment 1, wherein: at least 60% by weight of the second active ingredient is not released within 30 minutes after consumption; and at least 80% by weight of the third active ingredient is not released within 30 minutes after consumption.
4. The composition of embodiment 1, wherein: at least 50% by weight of the second active ingredient is released within 2 hours after consumption; and at least 60% by weight of the second active ingredient is not released within 30 minutes after consumption.
5. The composition of embodiment 1, wherein: at least 30% by weight of the second active ingredient is not released within 4 hours after consumption.
6. The composition of any one of embodiments 1-5, wherein: the first active ingredient is a source of vitamin C and a single dose to be administered includes an amount of 100 to 2000 mg; the second active ingredient is a multivalent cation and a single dose to be administered includes an amount of 5 to 40 mg; and the third active ingredient is a source of cholecalciferol and a single dose to be administered includes an amount of 5 to 30 mcg.
7. The composition of embodiment 6, wherein: the source of cholecalciferol s obtained from lichen.
8. The composition of any one of embodiments 1-7, wherein: the first active ingredient is caffeine and a single dose to be administered includes an amount of 100 to 700 mg.
9. The composition of any one of embodiments 1-8, wherein: the second active ingredient is a source of cannabinoids and a single dose to be administered includes an amount of 5 to 50 mg.
10. The composition of any one of embodiments 1-9, wherein: a single dose is administered in a 1 to 2 ounces shot.
11. The composition of any one of embodiments 1-10, wherein: the particle is part of the population of particles in the dispersion medium, and where the population has a Z-average diameter of about 0.5 to 5
12. The composition of any one of embodiments 1-11, wherein: the second polymer is a chelating agent for the second active ingredient.
13. The composition of any one of embodiments 1-12, wherein: the third polymer is selected from the group consisting of alginic acid, sodium alginate, potassium alginate, calcium alginate, agar, guar gum, and xanthan gum.
14. The composition of any one of embodiments 1-13, wherein: the second polymer is a water insoluble cellulose derivative.
15. The composition of any one of embodiments 1-14, wherein: the plurality of lipophilic carriers is selected from the group consisting of short-chain triglycerides, medium-chain triglycerides, long-chain triglycerides, medium-chain partial glycerides, polyoxyethylated fatty alcohols, polyethylene glycol, and vegetable oil.
16. The composition of any one of embodiments 1-15, the composition further including: at least one preservative agent selected from the group consisting of sodium benzoate, sodium metabisulfite, potassium sorbate, sorbic acid, acetic acid, propionic acid, sulfites, nitrites, sodium sorbate, calcium sorbate, benzoic acid, and potassium benzonate.
17. The composition of any one of embodiments 1-16, wherein: the plurality of emulsifying agents includes at least two agents selected from the group consisting of an extract of Quillaja, lecithin, monoglycerides, polysorbate 80, polysorbate 20, Polyglycerol polyricinoleate, gum acacia, Xanthan gum, sorbitol, mannitol, glycerol, and sodium alginate.
18. The composition of embodiment any one of embodiments 1-17, wherein: the core to the shell has a weight ratio in the range of 1:1.5 to 1:5.
19. The composition of any one of embodiments 1-18, wherein: each particle of the population of particles is configured to begin release of the second and the third active ingredients at a pH below about 5.
20. The composition of any one of embodiments 1-19, the shell further including: a wax selected from the group consisting of bees wax, carnauba wax, rice bran wax, camauba wax, and candelilla wax.
21. The composition of any one of embodiments 1-20, wherein: the composition is shelf stable for at least 12 months at room temperature.

Group B:
1. A method of encapsulation, the method including: providing a first mixture, the first mixture including: a first plurality of lipophilic carriers; a first plurality of active ingredients; a first polymer; and a first plurality of emulsifying agents; applying heat to the first mixture until the first mixture reaches a first temperature; providing a second mixture, the second mixture including: an aqueous solution; and a second polymer; applying heat to the second mixture until the second mixture reaches a second temperature; mixing the first mixture with the second mixture to obtain a third mixture; providing a fourth mixture, the fourth mixture including: a second plurality of lipophilic carriers; a third polymer; and a second plurality of emulsifying agents; applying heat to the fourth mixture until the fourth mixture reaches a third temperature; mixing the third mixture with the fourth mixture to obtain a fifth mixture; providing a sixth mixture, the sixth mixture including: an aqueous solution; applying heat to the sixth mixture until the sixth mixture reaches a fourth temperature; and mixing the fifth mixture with the sixth mixture to obtain a seventh mixture.

2. The method of embodiment 1, wherein: the first polymer has a first glass transition temperature; and the first temperature is above the first glass transition temperature.

3. The method of embodiment any one of embodiments 1-2, wherein: the second mixture has a third plurality of emulsifying agents.

4. The method of any one of embodiments 1-3, wherein: the fourth mixture further including: a crosslinking agent for the second polymer.

5. The method of any one of embodiments 1-4, wherein: the first polymer has a first glass transition temperature; the third polymer has a second glass transition temperature; and the first glass transition temperature is higher than the second glass transition temperature.

6. The method of any one of embodiments 1-5 further including: adding a thickening agent to the seventh mixture, wherein the thickening agent is a polysaccharide.

7. The method of any one of embodiments 1-6, wherein: the first plurality of emulsifying agents is selected from the group consisting of an extract of Quillaja, lecithin, monoglycerides, polysorbate 80, polysorbate 20, Polyglycerol polyricinoleate, gum acacia, Xanthan gum, sorbitol, mannitol, glycerol, and sodium alginate.

8. The method of any one of embodiments 1-7, wherein: the first plurality of emulsifying agents has a first hydrophilic-lipophilic balance value; the second plurality of emulsifying agents has a second hydrophilic-lipophilic balance value; and the first hydrophilic-lipophilic balance value is higher than the second hydrophilic-lipophilic balance value.

9. The method of any one of embodiments 1-8, wherein: the sixth mixture further including: a third plurality of emulsifying agents.

10. The method of any one of embodiments 1-9 further including: adding a fourth plurality of emulsifying agents to the fifth mixture before mixing the fifth mixture with the sixth mixture, wherein: the second plurality of emulsifying agents has a second hydrophilic-lipophilic balance value; the fourth plurality of emulsifying agents has a third hydrophilic-lipophilic balance value; and the third hydrophilic-lipophilic balance value is higher than the second hydrophilic-lipophilic balance value.

11. The method of any one of embodiments 1-10, wherein: the first plurality of active ingredients includes a source of cannabinoids, wherein the source of cannabinoids is selected from the group consisting of cannabigerol, cannabigerolic acid, cannabigerolic acid monomethylether, cannabigerol monomethyl ether, cannabichromene, cannabichromanon, cannabichromenic acid, cannabichromevarin, cannabichromevarinic acid, cannabidiol, tetrahydrocannabinol, iso-tetrahydrocannabinol-type, cannabinol, cannabinolic acid, cannabinol methylether, cannabicyclol-type, cannabicyclolic acid, cannabicyclovarin, cannabicitran, cannabitriol, cannabitriolvarin, cannabivarin, cannabifuran, and cannabiripsol.

12. The method of any one of embodiments 1-11, wherein: the first plurality of lipophilic carriers is selected from the group consisting of short-chain triglycerides, medium-chain triglycerides, long-chain triglycerides, medium-chain partial glycerides, polyoxyethylated fatty alcohols, polyethylene glycol, and vegetable oil.

13. The method of any one of embodiments 1-12, wherein: mixing the first mixture with the second mixture is done at a first shear rate; mixing the third mixture with the fourth mixture is done at a second shear rate; and the first shear rate is higher than the second shear rate.

14. The method of any one of embodiments 1-13, wherein: the seventh mixture includes: a dispersion medium including the sixth mixture; and a dispersed phase including droplets of the fifth mixture.

15. The method of any one of embodiments 1-14, wherein: the droplets of the fifth mixture have a mean diameter of less than 1 micron.

16. The method of any one of embodiments 1-15 further including: cooling the seventh mixture to a fifth temperature, wherein: the first polymer has a first glass transition temperature; the third polymer has a second glass transition temperature; and the fifth temperature is less than the first and the second glass transition temperatures.

17. The method of any one of embodiments 1-16, wherein: the first plurality of active ingredients is selected from the group consisting of hemp, *cannabis, Echinacea purpurea, Echinacea angustifolia, Echinacea pallida, Acmella oleracea, Helichrysum umbraculigerum, Radula marginata*, kava, black truffle, *Syzygium aromaticum, Rosmarinus officinalis*, basil, oregano, lavender, true cinnamon, malabathrum, *cananga odorata*, Riboflavin, Theanine, *Ginkgo biloba, Bacopa*, and *Rhodiola Rosea* Extract.

18. The method of any one of embodiments 1-171, wherein: at least 50% by weight of the first plurality of active ingredients is not released within 30 minutes after consumption of the seventh mixture.

19. The method of any one of embodiments 1-18, wherein: the weight ratio of the first mixture to the second mixture is from 1:1.5 to 1:5; the weight ratio of the third mixture to the fourth mixture is from 1:1.5 to 1:5; and the weight ratio of the fifth mixture to the sixth mixture is from 1:1.5 to 1:5.

20. The method of any one of embodiments 1-19, wherein: the fourth mixture further including: a second plurality of active ingredients, the second plurality of active ingredients includes: at least one source of bioavailability enhancer.

Group C:

1. A food and beverage additive having enhanced water solubility, the additive including: an aqueous solution; a first plurality of polymers; a first particle including: a first plurality of lipophilic carriers; a first active ingredient; a first plurality of emulsifying agents; and a second plurality of polymers; wherein the first particle exhibits higher hydrophilicity compared to the first active ingredient; and wherein a plurality of the first particles are uniformly dispersed in the aqueous solution.

2. The additive of embodiment 1, wherein: the aqueous solution is at least 55% by weight of the additive; the first active ingredient is at least 5% by weight of the additive; the first plurality of lipophilic carriers is at least 10% by weight of the additive; and the first active ingredient is less than 50% by weight of the first plurality of lipophilic carriers.

3. The additive of any one of embodiments 1-2, the additive further including: a second plurality of emulsifying agents selected from the group consisting of an extract of Quillaja, Tween 20, Tween 40, Tween 45, Tween 60, Tween 65, Tween 80, Tween 81 and Tween 85, polyglyceryl, gum acacia, Xanthan gum, sorbitol, mannitol, glycerol, and sodium alginate.

4. The additive of any one of embodiments 1-3, wherein: the first plurality of emulsifying agents has a hydrophilic-lipophilic balance (HLB) of higher than 8; and the first plurality of emulsifying agents is more than 25% by weight of the first plurality of lipophilic carriers.

5. The additive of any one of embodiments 1-4, the additive further including: at least one preservative agent selected from the group consisting of sodium benzoate, sodium metabisulfite, potassium sorbate, sorbic acid, acetic acid, propionic acid, sulfites, nitrites, sodium sorbate, calcium sorbate, benzoic acid, and potassium benzonate.

6. The additive of any one of embodiments 1-5, the additive further including: at least one flavoring agent.

7. The additive of any one of embodiments 1-6, wherein: the first particle has a Z-average diameter of smaller than 1 micron, when tested by Dynamic Light Scattering.

8. The additive of any one of embodiments 1-7, wherein: the first particle has a Z-average diameter of smaller than 200 nm, when tested by Dynamic Light Scattering.

9. The additive of any one of embodiments 1-7, wherein: the first particle has a Z-average diameter of smaller than 500 nm; and the additive can be stored at room temperature for at least 12 months, with less than 20% change in the Z-average diameter of the first particle.

10. The additive of any one of embodiments 1-7, wherein: the second plurality of polymers has a first glass transition temperature, wherein the first glass transition temperature is higher than 100° C.; the first particle has a Z-average diameter of smaller than 500 nm; and the additive can be stored at temperatures below 85° C. for at least 30 minutes, with less than 20% change in the Z-average diameter of the first particle.

11. The additive of embodiment any one of embodiments 1-10, wherein: the plurality of the first particles has a polydispersity of less than or equal to 0.25.

12. The additive of embodiment any one of embodiments 1-11, wherein: the aqueous solution is selected from the group consisting of: water, saline, propylene glycol, or combinations thereof.

13. The additive of embodiment any one of embodiments 1-12, wherein: the first active ingredient has a concentration of at least 40 milligram per milliliter of the additive.

14. The additive of embodiment any one of embodiments 1-13, wherein: the first active ingredient includes a source of cannabinoids, wherein the source of cannabinoids is selected from the group consisting of cannabigerol, cannabigerolic acid, cannabigerolic acid monomethylether, cannabigerol monomethyl ether, cannabichromene, cannabichromanon, cannabichromenic acid, cannabichromevarin, cannabichromevarinic acid, cannabidiol, tetrahydrocannabinol, iso-tetrahydrocannabinol-type, cannabinol, cannabinolic acid, cannabinol methylether, cannabicyclol-type, cannabicyclolic acid, cannabicyclovarin, cannabicitran, cannabitriol, cannabitriolvarin, cannabivarin, cannabifuran, and cannabiripsol.

15. The additive of embodiment any one of embodiments 1-14, wherein: at least 30% by weight of the first active ingredient is not released within 60 minutes after consumption.

16. The additive of embodiment any one of embodiments 1-15, the first particle further including: at least one source of bioavailability enhancer.

17. The additive of embodiment any one of embodiments 1-16, wherein: the second plurality of polymers includes ethylcellulose.

18. The additive of embodiment any one of embodiments 1-17, the first particle further including: at least one wax having a melting points exceeding 45° C.

19. The additive of embodiment any one of embodiments 1-18, the first particle further including: a second active ingredient, wherein the second active ingredient is selected from the group consisting of hemp, *cannabis, Echinacea purpurea, Echinacea angustifolia, Echinacea pallida, Acmella oleracea, Helichrysum umbraculigerum, Radula marginata*, kava, black truffle, *Syzygium aromaticum, Rosmarinus officinalis*, basil, oregano, lavender, true cinnamon, malabathrum, *cananga odorata*, Riboflavin, Theanine, *Ginkgo biloba, Bacopa*, and *Rhodiola Rosea* Extract.

20. The additive of embodiment any one of embodiments 1-19, wherein: the first plurality of lipophilic carriers is selected from the group consisting of short-chain triglycerides, medium-chain triglycerides, long-chain triglycerides, medium-chain partial glycerides, polyoxyethylated fatty alcohols, polyethylene glycol, and vegetable oil.

Group D:

1. A bead for use in beverage and food, the bead including: a core including: a continuous phase including: a lipophilic carrier; and a wax; a dispersed phase including: a particle including: a first active ingredient; and a first polymer; and a first shell substantially surrounding the core.

2. The bead of embodiment 1, wherein the continuous phase further including: a second polymer selected from the group consisting of shellac, methyl cellulose, hydroxy propyl cellulose, hydroxypropyl-methyl cellulose, ethyl methyl cellulose, carboxy methyl cellulose, ethyl cellulose, microcrystalline cellulose, cellulose, hypro mellose, hydroxyl propyl methyl cellulose, or combinations thereof.

3. The bead of embodiment 2, wherein the second polymer is dissolved in the lipophilic carrier.

4. The bead of embodiment any one of embodiments 1-3, wherein the continuous phase further including: an emulsifying agent, wherein the emulsifying agent has a hydrophilic-lipophilic balance less than 5.

5. The bead of embodiment any one of embodiments 1-4, wherein: the wax is selected from the group consisting of bees wax, carnauba wax, rice bran wax, camauba wax, candelilla wax, or combinations thereof.

6. The bead of embodiment any one of embodiments 1-5, wherein: at least 20% by weight of the first active ingredient is released within 60 minutes after consumption; and at least 20% by weight of the first active ingredient is not released within 4 hours after consumption.

7. The bead of embodiment any one of embodiments 1-6, the bead further including: a second shell substantially surrounding the core, wherein: the second shell is water insoluble; and the second shell retards the release of the first active ingredient after consumption.

8. The bead of embodiment any one of embodiments 1-7, wherein the particle further including: an aqueous solution selected from the group consisting of: water, saline, propylene glycol, or combinations thereof.
9. The bead of embodiment any one of embodiments 1-8, wherein: the particle has a Z-average diameter of smaller than 1 micron, when tested by Dynamic Light Scattering.
10. The bead of embodiment any one of embodiments 1-8, wherein: the bead has a Z-average diameter between 400-800 microns.
11. The bead of embodiment any one of embodiments 1-10, wherein: a plurality of the beads is administered in one capsule as a single dose.
12. The bead of any one of embodiments 1-10, wherein: a plurality of the beads is administered in a 1 to 2 ounces shot as a single dose.
13. The bead of embodiment 1, wherein: the first shell further including: a second active ingredient, wherein the second active ingredient is different from the first active ingredient.
14. The bead of embodiment 14, wherein: the first and the second ingredients are selected from the group consisting of hemp, *cannabis, Echinacea purpurea, Echinacea angustifolia, Echinacea pallida, Acmella oleracea, Helichrysum umbraculigerum, Radula marginata,* kava, black truffle, *Syzygium aromaticum, Rosmarinus officinalis,* basil, oregano, lavender, true cinnamon, malabathrum, *cananga odorata,* Riboflavin, Theanine, *Ginkgo biloba, Bacopa,* and *Rhodiola Rosea* Extract.
15. The bead of embodiment 14, wherein: the first active ingredient reduces the effect of the second active ingredient.
16. The bead of embodiment 1, wherein: the first shell includes a material or combination of materials that do not break down in an aqueous solution with a pH above 5.5.
17. The bead of any one of embodiments 1-16, wherein: the first shell includes a material or combination of materials that do not break down in an aqueous solution with a pH in the range of 2.0 to 5.0.
18. The bead of any one of embodiments 1-17, wherein: the first active ingredient is caffeine and a single dose to be administered includes an amount of 100 to 700 mg.
19. The bead of any one of embodiments 1-18, wherein: the first polymer is selected from the group consisting of alginic acid, sodium alginate, potassium alginate, calcium alginate, agar, guar gum, and xanthan gum.

Group E:
1. A method of encapsulation, the method including: providing a first mixture, the first mixture including: a first carrier; and a first active ingredient; applying heat to the first mixture until the first mixture reaches a first temperature; providing a second mixture, the second mixture including: a second carrier; and a first emulsifying agent; applying heat to the second mixture until the second mixture reaches a second temperature; mixing the first mixture with the second mixture to obtain a third mixture, wherein: the mixing is performed at a third temperature; and the third temperature is lower than the first temperature; and cooling the third mixture until the third mixture reaches a fourth temperature, wherein: the second carrier is in solid state at the fourth temperature.
2. The method of embodiment 1 further including: spray drying the third mixture to obtain a first plurality of beads, wherein: the first plurality of beads has a Z-average diameter less than 500 microns; and coating the first plurality of beads with a first layer, wherein: the first layer is water insoluble; and the first layer retards the release of the first active ingredient after consumption.
3. The method of embodiment 1 further including: grinding the third mixture to obtain a first plurality of beads, wherein: the first plurality of beads has a Z-average diameter between 400 to 800 microns; and spherinizing the first plurality of beads.
4. The method of embodiment 3 further including: coating the first plurality of beads with a first layer, wherein: the first layer is water insoluble; and the first layer retards the release of the first active ingredient after consumption.
5. The method of embodiment 4, wherein: the first layer is a cellulose-based material.
6. The method of embodiment 4, wherein: the first plurality of beads dispersed in a beverage are stable for at least 6 months.
7. The method of embodiment 4, wherein: the coating of the first layer is carried out in a fluidized bed.
8. The method of embodiment 4 further including: coating the first plurality of beads with a second layer, wherein: the second layer is water insoluble; and the second layer includes a material or combination of materials that do not break down in an aqueous solution with a pH above 5.5.
9. The method of embodiment 4, wherein: at least 20% by weight of the first active ingredient is not released within 2 hours after consumption.
10. The method of embodiment 4, wherein: the first layer has a thickness less than 50 microns.
11. The method of any one of embodiments 1-10, wherein the first mixture further including: an aqueous solution selected from the group consisting of: water, saline, propylene glycol, or combinations thereof; and a first polymer selected from the group consisting of alginic acid, sodium alginate, potassium alginate, calcium alginate, agar, guar gum, and xanthan gum.
12. The method of any one of embodiments 1-11, wherein the second carrier includes: a wax is selected from the group consisting of bees wax, carnauba wax, rice bran wax, carnauba wax, candelilla wax, or combinations thereof.
13. The method of any one of embodiments 1-12, wherein the second carrier includes: a first lipophilic carrier selected from the group consisting of short-chain triglycerides, medium-chain triglycerides, long-chain triglycerides, medium-chain partial glycerides, polyoxyethylated fatty alcohols, polyethylene glycol, and vegetable oil; and a second polymer selected from the group consisting of shellac, methyl cellulose, hydroxy propyl cellulose, hydroxypropyl-methyl cellulose, ethyl methyl cellulose, carboxy methyl cellulose, ethyl cellulose, microcrystalline cellulose, cellulose, hypro mellose, hydroxyl propyl methyl cellulose, or combinations thereof.
14. The method of any one of embodiments 1-13, wherein: the first emulsifying agent has a hydrophilic-lipophilic balance less than 5.
15. The method of any one of embodiments 1-14, wherein: the first emulsifying agent is selected from the group consisting of an extract of Quillaja, Tween 20, Tween 40, Tween 45, Tween 60, Tween 65, Tween 80, Tween 81 and Tween 85, polyglyceryl, gum acacia, Polyglycerol polyricinoleate, Span 85, Span 65, Span 83, Span 80, Span 60, Span 40, Xanthan gum, sorbitol, mannitol, glycerol, sodium alginate, or combinations thereof.
16. The method of any one of embodiments 1-15, wherein the first mixture further including: a second emulsifying agent selected from the group consisting of an extract of Quillaja, Tween 20, Tween 40, Tween 45, Tween 60, Tween 65, Tween 80, Tween 81 and Tween 85, polyglyceryl, gum acacia, Polyglycerol polyricinoleate, Span 85, Span 65, Span 83, Span 80, Span 60, Span 40, Xanthan gum, sorbitol, mannitol, glycerol, sodium alginate, or combinations thereof.

17. The method of any one of embodiments 1-16, wherein the second mixture further includes: a water insoluble material, wherein: the water insoluble material retards the release of the first active ingredient after consumption.

18. The method of any one of embodiments 1-17, wherein the second mixture further includes: a second active ingredient, wherein: the second active ingredient is different from the first active ingredient.

19. The method of embodiment 18, wherein: the first and the second ingredients are selected from the group consisting of probiotics, caffeine, hemp, *cannabis, Echinacea purpurea, Echinacea angustifolia, Echinacea pallida, Acmella oleracea, Helichrysum umbraculigerum, Radula marginata*, kava, black truffle, *Syzygium aromaticum, Rosmarinus officinalis*, basil, oregano, lavender, true cinnamon, malabathrum, *cananga odorata*, Riboflavin, Theanine, *Ginkgo biloba, Bacopa*, and *Rhodiola Rosea* Extract.

20. The method of any one of embodiments 1-19, wherein: the weight ratio of the first mixture to the second mixture is from 1:1.5 to 1:5.

Group F:
1. A multilayer particle, the particle including: a core including: a first active ingredient; and a first polymer; a first shell, substantially surrounding the core, the first shell including: a second polymer; a second shell, substantially surrounding the first shell, the second shell including: a third polymer; and a plurality of emulsifying agents.
2. The particle of embodiment 1, wherein the core further includes: an ion exchange resin equilibrated with the first active ingredient.
3. The particle of embodiment 1, wherein: at least two of the first, the second, and the third polymers are hydrophobic.
4. The particle of any one of embodiments 1-3, wherein: at least one of the second and the third polymers retards the release of the first active ingredient after consumption.
5. The particle of any one of embodiments 1-4, wherein: the second shell is sprayed on the first shell with a centrifugal atomizer.
6. The particle of any one of embodiments 1-4, wherein: the second shell is coated on the first shell with a fluidized bed.
7. The particle of any one of embodiments 1-6, wherein: the second shell is formed using compression coating.
8. The particle of any one of embodiments 1-7, wherein: the particle has a Z-average diameter between 400 to 800 microns.
9. The particle of embodiment 8, wherein: the core has a diameter between 20% to 80% of the particle's diameter; the first shell has a diameter between 5% to 20% of the particle's diameter; and the second shell has a diameter between 5% to 20% of the particle's diameter.
10. The particle of any one of embodiments 1-9, wherein: the particle has a Z-average diameter less than 1 micron.
11. The particle of any one of embodiments 1-10, wherein: the plurality of emulsifying agents is selected from the group consisting of an extract of Quillaja, Tween 20, Tween 40, Tween 45, Tween 60, Tween 65, Tween 80, Tween 81 and Tween 85, polyglyceryl, gum acacia, Polyglycerol polyricinoleate, Span 85, Span 65, Span 83, Span 80, Span 60, Span 40, Xanthan gum, sorbitol, mannitol, glycerol, sodium alginate, or combinations thereof 12. The particle of any one of embodiments 1-11, wherein: at least a portion of the plurality of emulsifying agents is in the core; and at least a portion of the plurality of emulsifying agents is in the first shell.
13. The particle of any one of embodiments 1-12, wherein: at least a portion of the plurality of emulsifying agents is in the core; at least a portion of the plurality of emulsifying agents is in the first shell, and at least a portion of the plurality of emulsifying agents is in the second shell.
14. The particle of embodiment any one of embodiments 1-13, wherein the first shell further including: a second active ingredient.
15. The particle of embodiment 14, wherein: the first and the second active ingredients are selected from the group consisting of probiotics, caffeine, hemp, *cannabis, Echinacea purpurea, Echinacea angustifolia, Echinacea pallida, Acmella oleracea, Helichrysum umbraculigerum, Radula marginata*, kava, black truffle, *Syzygium aromaticum, Rosmarinus officinalis*, basil, oregano, lavender, true cinnamon, malabathrum, *cananga odorata*, Riboflavin, Theanine, *Ginkgo biloba, Bacopa*, and *Rhodiola Rosea* Extract.
16. The particle of embodiment 14, wherein: at least one of the first and the second active ingredients includes a source of cannabinoids, wherein the source of cannabinoids is selected from the group consisting of cannabigerol, cannabigerolic acid, cannabigerolic acid monomethylether, cannabigerol monomethyl ether, cannabichromene, cannabichromanon, cannabichromenic acid, cannabichromevarin, cannabichromevarinic acid, cannabidiol, tetrahydrocannabinol, iso-tetrahydrocannabinol-type, cannabinol, cannabinolic acid, cannabinol methylether, cannabicyclol-type, cannabicyclolic acid, cannabicyclovarin, cannabicitran, cannabitriol, cannabitriolvarin, cannabivarin, cannabifuran, and cannabiripsol.
17. The particle of embodiment any one of embodiments 1-16, wherein: at least one of the first, second, and the third polymers has a glass transition temperature above 120° C.
18. The particle of embodiment any one of embodiments 1-17, wherein: the first, second, and the third polymers selected from the group consisting of alginic acid, sodium alginate, potassium alginate, calcium alginate, agar, guar gum, xanthan gum; shellac, methyl cellulose, hydroxy propyl cellulose, hydroxypropyl-methyl cellulose, ethyl methyl cellulose, carboxy methyl cellulose, ethyl cellulose, microcrystalline cellulose, cellulose, hypro mellose, hydroxyl propyl methyl cellulose, or combinations thereof.
19. The particle of any one of embodiments 1-18, wherein: the particle is shelf stable for at least 12 months at room temperature.
20. The particle of any one of embodiments 1-19, wherein the first shell further includes: a wax selected from the group consisting of bees wax, carnauba wax, rice bran wax, camauba wax, and candelilla wax.

Group G:
1. A food and beverage additive, the additive including: a first phase including: a first filler; a second phase, the second phase including: a second filler; and a third phase, the third phase including: a third filler; and a fourth phase, the fourth phase including: a fifth filler; and a first active ingredient.
2. The additive of embodiment 1, wherein the third phase further includes: the first active ingredient.
3. The additive of any one of embodiments 1-2 further including: a plurality of emulsifying agents selected from the group consisting of an extract of Quillaja, Tween 20, Tween 40, Tween 45, Tween 60, Tween 65, Tween 80, Tween 81 and Tween 85, polyglyceryl, gum acacia, Polyglycerol polyricinoleate, Span 85, Span 65, Span 83, Span 80, Span 60, Span 40, Xanthan gum, sorbitol, mannitol, glycerol, sodium alginate, or combinations thereof
4. The additive of embodiment 3, wherein: every one of the first, the second, the third, the fourth, and the fifth phases has at least a portion of plurality of emulsifying agents.
5. The additive of any one of embodiments 1-4, wherein: the first and third phases are water insoluble; and the second and fourth phases are aqueous phases.
6. The additive of any one of embodiments 1-5, wherein: the second and fourth phases are water insoluble; and the first and third phases are aqueous phases.
7. The additive of any one of embodiments 1-6, wherein: the second filler is selected from selected from the group consisting of short-chain triglycerides, medium-chain triglycerides, long-chain triglycerides, medium-chain partial glycerides, polyoxyethylated fatty alcohols, polyethylene glycol, and vegetable oil, shellac, methyl cellulose, hydroxy propyl cellulose, hydroxypropyl-methyl cellulose, ethyl methyl cellulose, carboxy methyl cellulose, ethyl cellulose, microcrystalline cellulose, cellulose, hypro mellose, hydroxyl propyl methyl cellulose, or combinations thereof
8. The additive of any one of embodiments 1-7, wherein: the fifth filler is selected from is selected from the group consisting of alginic acid, sodium alginate, potassium alginate, calcium alginate, agar, guar gum, and xanthan gum.
9. The additive of any one of embodiments 1-81, wherein the fourth phase further includes: the second active ingredient, wherein: if the first active ingredient is water soluble, the second active ingredient is a hydrophobic compound; and if the first active ingredient is oil soluble, the second active ingredient is a hydrophilic compound.
10. The additive of any one of embodiments 1-9, wherein: the weight ratio of the second phase to the first phase is from 1:1.5 to 1:5; the weight ratio of the third phase to the second phase is from 1:1.5 to 1:5; the weight ratio of the fourth phase to the third phase is from 1:1.5 to 1:5; and the weight ratio of the fifth phase to the fourth phase is from 1:1.5 to 1:5.
11. The additive of any one of embodiments 1-10, wherein: the first filler has a melting point; the additive is chilled by contact with a surface at a temperature less than the melting point of the first filler to form flakes.
12. The additive of any one of embodiments 1-11, wherein: at least three of the first, the second, the third, the fourth, and the fifth fillers retard the release of the first active ingredient after consumption.
13. The additive of any one of embodiments 1-12, wherein: the first active ingredient is uniformly distributed in the fifth filler.
14. The additive of any one of embodiments 1-13, wherein: the additive is spray dried to obtain a population of beads, wherein: the population of beads has a Z-average diameter less than 500 microns.
15. The additive of any one of embodiments 1-14, wherein: the additive has a Z-average diameter of smaller than one micron; and the additive can be stored at room temperature for at least 12 months, with less than 50% change in the Z-average diameter of the additive.
16. The additive of any one of embodiments 1-15, wherein: the additive has a Z-average diameter of smaller than 500 nm; and the additive can be stored at temperatures below 85° C. for at least 30 seconds, with less than 20% change in the Z-average diameter of the additive.
17. The additive of embodiment 1, wherein: at least 10% by weight of the first active ingredient is not released within 2 hours after consumption.
18. The additive of any one of embodiments 1-17, wherein: the first filler do not break down in an aqueous solution with a pH above 5.5.
19. The additive of any one of embodiments 1-18, wherein the first filler comprises: a wax is selected from the group consisting of bees wax, carnauba wax, rice bran wax, camauba wax, candelilla wax, or combinations thereof.
20. The additive of any one of embodiments 1-19, wherein: the first active ingredient is selected from the group consisting of probiotics, caffeine, Dynamine, hemp, *cannabis, Echinacea purpurea, Echinacea angustifolia, Echinacea pallida, Acmella oleracea, Helichrysum umbraculigerum, Radula marginata*, kava, black truffle, *Syzygium aromaticum, Rosmarinus officinalis*, basil, oregano, lavender, true cinnamon, malabathrum, *cananga odorata*, Riboflavin, Theanine, *Ginkgo biloba, Bacopa*, and *Rhodiola Rosea* Extract.

What is claimed is:
1. A composition for oral administration, the composition comprising:
   a dispersion medium comprising:
      an aqueous solution; and
   a dispersed phase comprising:
      a population of particles, each particle comprising:
         a first active ingredient selected from the group consisting of *Echinacea Purpurea, Echinacea Angustifolia, Echinacea Pallida, Acmella Oleracea, Helichrysum umbraculigerum, Radula marginata*, Kava, Kanna, black truffle, *Syzygium aromaticum, Rosmarinus* Oficinalis, *Sceletium tortuosum*, Holy basil, Oregano, Lavender, Cinnamon, Malabathrum, *Cananga odorata, Ginkgo biloba, Bacopa*, and *Rhodiola rosea*, Ashwagandha, *Astragalus, Chaga, Cordyceps, Corydalis*, Curcumin, Damiana, Eleuthero, Ginger root, Ginseng, Gotu Kola, Lion's Mane, Maca, Passionflower, Saffron, Schisandra, St. John's Wort, Turmeric, Turkey Tail, Valerian root, and Yohimbe; and
         a lipophilic carrier selected from the group consisting of short-chain triglycerides, medium-chain triglycerides, long-chain triglycerides, medium-chain partial glycerides, polyoxyethylated fatty alcohols, polyethylene glycol, lemon oil, orange oil, peppermint oil, spearmint oil, Ylang Ylang oil, Lemon Grass oil, Tea Tree oil, Rosemary oil, Australian Sandalwood oil, Grape fruit oil, frankincense oil, cedarwood oil, patchouli oil, cinnamon bark oil, bergamot oil, chamomile oil, Lemon *Eucalyptus* oil, ginger oil, key lime oil, vanilla oil, vegetable oil, and combinations thereof; and
         a plurality of emulsifying agents selected from the group consisting of an extract of Quillaj a, Tween 20, Tween 40, Tween 45, Tween 60, Tween 65, Tween 80, Tween 81 and Tween 85, polyglyceryl, gum acacia, Polyglycerol polyricinoleate, Span 85, Span 65, Span 83, Span 80, Span 60, Span 40, Xanthan gum, sorbitol, mannitol, glycerol, sodium alginate, D-α-tocopheryl polyethylene glycol succinate, polyglycerols of oleic acid, and combinations thereof;

wherein the particle retards the release of the first active ingredient after consumption.

2. The composition of claim 1, wherein each particle further comprising:
a second active ingredient selected from the group consisting of cannabidiol, cannabichromene, cannabigerol, cannabicyclol, cannabinol, cannabigerolic acid, cannabigerolic acid monomethylether, cannabigerol monomethyl ether, cannabichromanon, cannabichromenic acid, cannabichromevarin, cannabichromevarinic acid, tetrahydrocannabinol, iso-tetrahydrocannabinol, cannabinol methylether, cannabinol-C4, cannabinol-C2, cannabiorcol, cannabinodiol, cannabielsoin, cannabielsoic acid A, cannabielsoic acid B, cannabicyclol, cannabicyclolic acid, cannabicyclovarin, cannabicitran, cannabitriol, cannabitriolvarin, ethoxy-cannabitiolvarin, cannabivarin, cannabinodivarin, tetrahydrocannabivarin, cannabidivarin, cannabigerovarin, cannabigerovarinic acid, cannabifuran, dehydrocannabifuran, and cannabiripsol cannabinoids.

3. The composition of claim 1, wherein the composition is a beverage, a gum, or a food snack.

4. The composition of claim 1, wherein the aqueous solution further comprising:
a first polymer selected from the group consisting of alginic acid, gum Arabic, locust bean gum, sodium alginate, potassium alginate, calcium alginate, agar, guar gum, and xanthan gum.

5. The composition of claim 1, wherein each particle further comprising:
a second polymer, wherein the second polymer is water insoluble and is selected from the group consisting of methyl cellulose, hydroxypropyl cellulose, hydroxypropyl methylcellulose, shellac, ethyl methyl cellulose, carboxymethyl cellulose, ethyl cellulose, microcrystalline cellulose, cellulose, 12-hydroxystearic acid, and combinations thereof.

6. The composition of claim 5, wherein:
the second polymer has a glass transition temperature above 120° C.

7. The composition of claim 1, wherein:
at least 10% by weight of the first active ingredient is not released within 3 hours after consumption.

8. The composition of claim 1, wherein each particle further comprises:
a wax is selected from the group consisting of bees wax, carnauba wax, rice bran wax, camauba wax, candelilla wax, or combinations thereof.

9. The composition of claim 1, wherein the composition further comprises:
at least one source of bioavailibity enhancer selected from the group consisting of naringin, naringenin, piperine, capsaicin, curcumin, demethoxycurcumin, bis-demethoxycurcumin, quercetin, allicin, lysergol, genistein, sinomenine, gallic acid, glycodeoxycholic acid, docosahexaenoic acid, eicosapentaenoic acid, epicatechin, cyclosporine, diosmin, emodin, fulvic acid genistein, lycopene, trans-resveratrol, cis-resveratrol, capric acid, cholic acid, deoxycholic acid, tamarixetin, glycocholic acid, taurocholic acid, limonene carvone, tangeretin, nobiletin, bergamottin, 6',7'-dihydroxybergamottin, L-palmitoylcarnitine, and quinidine.

10. The composition of claim 1, wherein the composition further comprises:
a second active ingredient selected from the group consisting of methylphenidate, dextroamphetamine, amphetamine, Caffeine, nicotine, Methamphetamine, 3,4-Methylenedioxymethamphetamine, Methylenedioxypyrovalerone, Mephedrone, Phenylpropanolamine, Propylhexedrine, Pseudoephedrine, Catha *edulis*, Modafinil, xanthines, theophylline, and theobromine.

11. The composition of claim 1, wherein the population of particles has a net negative charge that is −15 mV or lower.

12. The composition of claim 11, wherein the net negative charge of the population of particles causes the one or more nanoparticles to repel each other with a force of repulsion that leads to stable dispersion of the one or more nanoparticles when the first composition is diluted at least up to 10 fold with an aqueous fluid.

13. The composition of claim 1, wherein:
the population of particles have a Z-average diameter between 50 to 950 nanometers;
the Z-average diameter of the population of particles changes less than 20% when the composition is incubated at 40° C. for four weeks; and
the Z-average diameter of the population of particles changes less than 20% when the composition is incubated at 90° C. for 30 minutes.

14. The composition of claim 1, wherein:
the population of particles do not break down in an aqueous solution with a pH in the range of 2.0 to 5.0.

15. The composition of claim 1, wherein the population of particles are 0.01 wt % to 70 wt % of the composition.

16. The composition of claim 1, wherein:
the composition is spray dried to obtain a population of beads, wherein:
the population of beads has a Z-average diameter between 100 and 900 microns.

17. A composition for oral administration, the composition comprising:
a dispersion medium comprising:
an aqueous solution; and
a first polymer selected from the group consisting of alginic acid, gum Arabic, locust bean gum, sodium alginate, potassium alginate, calcium alginate, agar, guar gum, and xanthan gum; and
a dispersed phase comprising:
a population of particles, each particle comprising:
a first active ingredient selected from the group consisting of *Echinacea Purpurea, Echinacea Angustifolia, Echinacea Pallida, Acmella Oleracea, Helichrysum umbraculigerum, Radula marginata*, Kava, Kanna, black truffle, *Syzygium aromaticum, Rosmarinus* Oficinalis, *Sceletium tortuosum*, Holy basil, Oregano, Lavender, Cinnamon, Malabathrum, *Cananga odorata, Ginkgo biloba, Bacopa*, and *Rhodiola rosea*, Ashwagandha, *Astragalus, Chaga, Cordyceps, Corydalis*, Curcumin, Damiana, Eleuthero, Ginger root, *Ginseng*, Gotu Kola, Lion's Mane, Maca, Passionflower, Saffron, Schisandra, St. John's Wort, Turmeric, Turkey Tail, Valerian root, and Yohimbe; and
a lipophilic carrier selected from the group consisting of short-chain triglycerides, medium-chain triglycerides, long-chain triglycerides, medium-chain partial glycerides, polyoxyethylated fatty alcohols, polyethylene glycol, lemon oil, orange oil, peppermint oil, spearmint oil, Ylang Ylang oil, Lemon Grass oil, Tea Tree oil, Rosemary oil, Australian Sandalwood oil, Grape fruit oil, frankincense oil, cedarwood oil, patchouli oil, cinnamon bark oil, bergamot oil, chamomile oil, Lemon

*Eucalyptus* oil, ginger oil, key lime oil, vanilla oil, vegetable oil, and combinations thereof;

a second polymer, wherein the second polymer is water insoluble and is selected from the group consisting of methyl cellulose, hydroxypropyl cellulose, hydroxypropyl methylcellulose, shellac, ethyl methyl cellulose, carboxymethyl cellulose, ethyl cellulose, microcrystalline cellulose, cellulose, 12-hydroxystearic acid, and combinations thereof; and a plurality of emulsifying agents selected from the group consisting of an extract of Quillaj a, Tween 20, Tween 40, Tween 45, Tween 60, Tween 65, Tween 80, Tween 81 and Tween 85, polyglyceryl, gum acacia, Polyglycerol polyricinoleate, Span 85, Span 65, Span 83, Span 80, Span 60, Span 40, Xanthan gum, sorbitol, mannitol, glycerol, sodium alginate, D-α-tocopheryl polyethylene glycol succinate, polyglycerols of oleic acid, and combinations thereof, wherein the particle retards the release of the first active ingredient after consumption;

the population of particles have a Z-average diameter between 50 to 950 nanometers;

the Z-average diameter of the population of particles changes less than 20% when the composition is incubated at 40° C. for four weeks; and the Z-average diameter of the population of particles changes less than 20% when the composition is incubated at 90° C. for 30 minutes.

\* \* \* \* \*